United States Patent
Babb et al.

(10) Patent No.: US 12,331,127 B2
(45) Date of Patent: Jun. 17, 2025

(54) THERAPEUTIC USES OF ANTI-GITR ANTIBODIES

(71) Applicant: Regeneron Pharmaceuticals, Inc., Tarrytown, NY (US)

(72) Inventors: Robert Babb, River Edge, NJ (US); Drew Dudgeon, Montvale, NJ (US); Yu Huang, Ossining, NY (US); Rosalynn Molden, Shoreline, WA (US); William Olson, Yorktown Heights, NY (US); Matthew Sleeman, Yorktown Heights, NY (US); Dimitris Skokos, New York, NY (US); Bei Wang, Hastings-on-Hudson, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 0 days.

(21) Appl. No.: 18/461,760

(22) Filed: Sep. 6, 2023

(65) Prior Publication Data
US 2024/0076396 A1 Mar. 7, 2024

Related U.S. Application Data

(62) Division of application No. 17/193,586, filed on Mar. 5, 2021, now Pat. No. 11,787,867.
(Continued)

(51) Int. Cl.
*A61K 39/395* (2006.01)
*A61P 35/00* (2006.01)
(Continued)

(52) U.S. Cl.
CPC ...... *C07K 16/2878* (2013.01); *A61K 39/3955* (2013.01); *A61P 35/00* (2018.01);
(Continued)

(58) Field of Classification Search
None
See application file for complete search history.

(56) References Cited

U.S. PATENT DOCUMENTS

| | | |
|---|---|---|
| 5,500,362 A | 3/1996 | Robinson et al. |
| 5,821,337 A | 10/1998 | Carter et al. |

(Continued)

FOREIGN PATENT DOCUMENTS

| | | |
|---|---|---|
| EP | 1462114 | 9/2004 |
| WO | WO 1998/06842 A1 | 2/1998 |

(Continued)

OTHER PUBLICATIONS

Sanmamed et al., Agonists of Co-stimulation in Cancer Immunotherapy Directed Against CD137, OX40, GITR, CD27, CD28, and ICOS, Sem. Oncol. 42(4):640-655, Aug. 2015.*
(Continued)

*Primary Examiner* — Claire Kaufman
(74) *Attorney, Agent, or Firm* — FisherBroyles, LLP; Cara L. Crowley-Weber; Lisa Dornbach Flanagan

(57) ABSTRACT

Provided herein are antibodies, and antigen-binding fragments thereof that specifically bind glucocorticoid-induced tumor necrosis factor receptor (GITR), compositions comprising the antibodies or antigen-binding fragments thereof, and methods of using the same, including, e.g., methods of treatment using the same.

55 Claims, 21 Drawing Sheets

Specification includes a Sequence Listing.

Related U.S. Application Data

(60) Provisional application No. 62/986,494, filed on Mar. 6, 2020.

(51) Int. Cl.
 *C07K 16/28* (2006.01)
 *A61K 39/00* (2006.01)

(52) U.S. Cl.
 CPC .. *A61K 2039/505* (2013.01); *C07K 2317/565* (2013.01); *C07K 2317/732* (2013.01); *C07K 2317/76* (2013.01)

(56) References Cited

U.S. PATENT DOCUMENTS

| | | |
|---|---|---|
| 6,503,184 B1 | 1/2003 | Ni et al. |
| 6,689,607 B2 | 2/2004 | Ni et al. |
| 7,025,962 B1 | 4/2006 | Gorman et al. |
| 7,618,632 B2 | 11/2009 | Collins et al. |
| 7,812,135 B2 | 10/2010 | Smith et al. |
| 8,388,967 B2 | 3/2013 | Smith et al. |
| 8,709,424 B2 | 4/2014 | Schebye et al. |
| 9,028,823 B2 | 5/2015 | Smith et al. |
| 9,175,308 B2 | 11/2015 | Shiku et al. |
| 9,228,016 B2 | 1/2016 | Wang et al. |
| 9,309,321 B2 | 4/2016 | Kwon |
| 9,464,139 B2 | 10/2016 | Beers et al. |
| 9,493,572 B2 | 11/2016 | Smith et al. |
| 9,701,751 B2 | 7/2017 | Schebye et al. |
| 9,745,379 B2 | 8/2017 | Wang et al. |
| 9,987,500 B2 | 6/2018 | Papadopoulos et al. |
| 10,738,126 B2 | 8/2020 | Delfino et al. |
| 11,274,342 B2 | 3/2022 | Zhang et al. |
| 11,414,494 B2 | 8/2022 | Delfino et al. |
| 11,787,867 B2 | 10/2023 | Babb et al. |
| 2006/0099171 A1 | 3/2006 | Tone et al. |
| 2007/0098719 A1 | 5/2007 | Smith et al. |
| 2007/0280945 A1 | 12/2007 | Stevens et al. |
| 2009/0136494 A1 | 5/2009 | Ponath et al. |
| 2010/0061984 A1 | 3/2010 | Greene et al. |
| 2011/0059109 A1 | 3/2011 | Smith et al. |
| 2011/0212086 A1 | 9/2011 | Shankara et al. |
| 2012/0189639 A1 | 7/2012 | Schebye et al. |
| 2013/0108641 A1 | 5/2013 | Baurin et al. |
| 2013/0183321 A1 | 7/2013 | Smith et al. |
| 2014/0072565 A1 | 3/2014 | Kwon |
| 2014/0072566 A1 | 3/2014 | Kwon |
| 2014/0348841 A1 | 11/2014 | Schebye et al. |
| 2015/0064204 A1 | 3/2015 | Beers et al. |
| 2015/0203579 A1 | 7/2015 | Papadopoulos et al. |
| 2015/0353637 A1 | 12/2015 | Wang et al. |
| 2015/0368349 A1 | 12/2015 | Seibert et al. |
| 2017/0355774 A1 | 12/2017 | Delfino et al. |
| 2021/0340267 A1 | 11/2021 | Babb et al. |
| 2023/0042324 A1 | 2/2023 | Delfino et al. |

FOREIGN PATENT DOCUMENTS

| | | |
|---|---|---|
| WO | WO 1999/25834 | 5/1999 |
| WO | WO 2004/107618 | 12/2004 |
| WO | WO 2006/105021 A2 | 10/2006 |
| WO | WO 2011/028683 A1 | 3/2011 |
| WO | WO 2015/026684 A1 | 2/2015 |
| WO | WO 2015/031667 | 3/2015 |
| WO | WO 2015/184099 A1 | 3/2015 |
| WO | WO 2015/187835 A2 | 12/2015 |
| WO | WO 2016/054638 | 4/2016 |
| WO | WO 2016/057846 | 4/2016 |
| WO | WO 2016/070051 A2 | 5/2016 |
| WO | WO2017/030823 A2 | 2/2017 |
| WO | WO 2017/214548 A1 | 12/2017 |
| WO | WO2018/025178 A1 | 2/2018 |

OTHER PUBLICATIONS

Accession No. NP_004186.1 To: Protein [Internet]. Bethesda (MD): National Library of Medicine (US), National Center for Biotechnology Information; [2021]—Accession No. NP_004186.1, "Tumor Necrosis Factor Receptor Superfamily Member 18 Isoform 1 Precursor [*Homo sapiens*]", cited on May 24, 2021, [online], [retrieved on May 25, 2021]. Retrieved from: https://www.ncbi.nlm.nih.gov/protein/NP_004186.1, 3 pages.
Altschul et al. (1990) "Basic Local Alignment Search Tool," J. Mol. Biol., 215: 403-410.
Altschul et al. (1997) "Gapped Blast and PSI-Blast: A New Generation of Protein Database Search Programs," Nucleic Acids Res., 25(17): 3389-3402.
Angal et al. (1993) "A Single Amino Acid Substitution Abolishes the Heterogeneity of Chimeric Mouse/Human (IgG4) Antibody," Molecular Immunology, 30(1): 105-108.
Barbee, et al. (2016) "Novel Tetravalent Anti-GITR Antibody is a Potent Anti-tumor Agent In Vivo", Annual Meeting in National Harbor, Maryland. Poster #175, Nov. 11, 2016, 1 page.
Clouthier et al. (2014) "Cell-specific and Context-dependent Effects of GITR in Cancer, Autoimmunity, and Infection," Cytokine & Growth Factor Reviews, 25(2): 91-106.
Clynes et al. (1998) "Fc Receptors are Required in Passive and Active Immunity to Melanoma," The National Academy of Sciences, 95: 652-656.
Dondelinger et al. (2018) "Understanding the Significance and Implications of Antibody Numbering and Antigen-Binding Surface/Residue Definition," Frontiers in Immunology, 9: 1-15.
Ehring (1999) "Hydrogen Exchange/Electrospray Ionization Mass Spectrometry Studies of Structural Features of Proteins and Protein/Protein Interactions," Analytical Biochemistry, 267(2): 252-259.
Engen and Smith (2001) "The Basics of Ion Chromatography, Metrohm 792 Basic IC," Anal. Chem., 73: 256A-265A.
Gershoni et al. (2007) "Epitope Mapping, The First Step in Developing Epitope-Based Vaccines," BioDrugs, 21(3): 145-156.
Gonnet et al. (1992) "Exhaustive Matching of the Entire Protein Sequence Database," Science 256: 1443-1445.
Harlow and Lane (2014) "Antibodies," A Laboratory Manual, Second Edition, Cold Spring Harbor Press, Cold Spring Harbor, NY.
International Search Report and Written Opinion received in PCT/US2017/036818 on Nov. 6, 2017 (30 pages).
International Search Report and Written Opinion received in PCT/US2021/021109 on Jun. 21, 2021 (15 pages).
Junghans et al. (1990) "Anti-Tac-H, a Humanized Antibody to the Interleukin 2 Receptor with New Features for Immunotherapy in Malignant and Immune Disorders," Cancer Res., 50: 1495-1502.
Kanamaru et al. (2004) "Costimulation via Glucocorticoid-Induced TNF Receptor in Both Conventional and CD25+ Regulatory CD4+ T Cells," J. Immunol., 172: 7306-7314 (10 pages) http://www.jimmunol.org/content/172/12/7306.
Kazane et al. (2012) "Synthesis of Bispecific Antibodies using Genetically Encoded Unnatural Amino Acids," J. Am. Chem. Soc., [Epub: Dec. 4, 2012].
Kazane et al. (2013) "Self-Assembled Antibody Multimers Through Peptide Nucleic Acid Conjugation," J Am Chem Soc., 135(1): 340-346.
Klein et al. (2012) "Progress in Overcoming the Chain Association Issue in Bispecific Heterodimeric IgG Antibodies," mAbs, 4(6): 1-11.
Knee et al. (2016) "Rationale for Anti-GITR Cancer Immunotherapy," European Journal of Cancer, 67: 1-10.
Krausz et al. (2007) "GITR-GITRL System, a Novel Player in Shock and Inflammation," The Scientific World Journal, 7: 533-566.
Kufer et al. (2004) "A Revival of Bispecific Antibodies," Trends Biotechnol., 22(5): 238-244.
Langer (1990) "New Methods of Drug Delivery," Science, 249: 1527-1533.
Langer and Wise (eds.) (1984) "Medical Applications of Controlled Release vol. II," CRC Pres., Boca Raton, Florida, pp. 115-138.
Li et al. (2014) "Framework Selection Can Influence Pharmacokinetics of a Humanized Therapeutic Antibody Through Differences in Molecule Charge," mABS, Landes Bioscience, US, 6(5): 1255-1264.

(56) References Cited

OTHER PUBLICATIONS

Lu et al. (2014) "Combined PD-1 Blockade and GITR Triggering Induce a Potent Antitumor Immunity in Murine Cancer Models and Synergizes with Chemotherapeutic Drugs," Journal of Translational Medicine 12: 36 (11 pages).
Mordenti et al. (1991) "Interspecies Scaling of Clearance and Volume of Distribution Data for Five Therapeutic Proteins," Pharmaceut. Res., 8: 1351-1359.
Nocentini et al. (2015) "Modulation of Tumour Immunity: A Patent Evaluation of WO 2015/026684A1," Expert Opinion on Therapeutic Patents, 32 pages.
Padlan et al. (1995) "Identification of Specificity-Determining Residues in Antibodies," FASEB J., 9: 133-139.
Pearson (1994) "Using the FASTA Program to Search Protein and DNA Sequence Database," Methods Mol. Biol., 24: 307-331.
Pearson (2000) "Flexible Sequence Similarity Searching with the FASTA3 Program Package," Methods in Molecular Biology, 132: 185-219.
Perez De La Lastra (1999) "Epitope Mapping 10 Monoclonal Antibodies Against the Pig Analogue of Human Membrane Cofactor Protein (MCP)," Immunology, 96: 663-670.
Powell et al. (1998) "Compendium of Excipients for Parenteral Formulations," PDA, J Pharm Sci Technol, 52: 238-311.
Reddy et al. (2000) "Elimination of Fc Receptor-Dependent Effector Functions of a Modified IgG4 Monoclonal Antibody to Human CD4," J. Immunol., 164: 1925-1933.
Reineke, (2004) "Antibody Epitope Mapping Using Arrays of Synthetic Peptides," Methods Mol Biol., 248: 443-463.
Rudikoff et al. (1982) "Single Amino Acid Substitution Altering Antigen-binding Specificity," Proc. Natl. Acad. Sci., 79: 1979-1983 (5 pages).
Schaer et al. (2012) "Modulation of GITR for Cancer Immunotherapy," Curr. Opin. Immunol., 24: 217-224.
Sefton (1987) "Implantable Pumps," CRC Crit. Ref. Biomed. Eng., 14(3): 201-240.
Shevach and Stephens (2006) "The GITR-GITRL interaction: Co-stimulation or Contrasuppression of Regulatory Activity?" Nat. Rev. Immunol., 6: 613-618.
Shields et al. (2002) "Lack of Fucose on Human IgG1 N-Linked Oligosaccharide Improves Binding to Human FcγRIII and Antibody-dependent Cellular Toxicity," JBC, 277(30): 26733-26740.
Shimizu et al. (2002) "Stimulation of CD25(+)CD4(+) Regulatory T Cells Through GITR Breaks Immunological Self-Tolerance," Nature Immunology, 3(2): 135-142.
Taylor et al. (1992) "A Transgenic Mouse that Expresses a Diversity of Human Sequence Heavy and Light Chain Immunoglobulins," Nucl. Acids Res., 20(23): 6287-6295.
Tomer et al. (2000) "Characterization of a Discontinuous Epitope of the Human Immunodeficiency Virus (HIV) Core Protein p24 by Epitope Excision and Differential Chemical Modification Followed by Mass Spectrometric Peptide Mapping Analysis," Protein Science, 9: 487-496.
Tutt et al. (1991)"Trispecific F(ab')3 Derivatives That Use Cooperative Signaling via the TCR/CD3 Complex and CD2 to Activate and Redirect Resting Cytotoxic T Cells," J. Immunol., 147: 60-69.
Vajdos et al. (2002) "Comprehensive Functional Maps of the Antigen-binding Site of an Anti-ErbB2 Antibody Obtained with Shotgun Scanning Mutagenesis," J Mol Biol., 320: 415-428.
Wu et al. (1987) "Receptor-Mediated in Vitro Gene Transformation by a Soluble DNA Carrier System," J. Biol. Chem., 262: 4429-4432.
Yang et al. (2015) "TCRklass: A New K-String-Based Algorithm Characterization for Human and Mouse TCR Repertoire," The Journal of Immunology, 194: 446-454.
Zhao et al. (2015) "Expression of GITR Enhances Multiple Myeloma Cell Sensitivity to Bortezomib," PLoS ONE, pp. 1-12.

\* cited by examiner

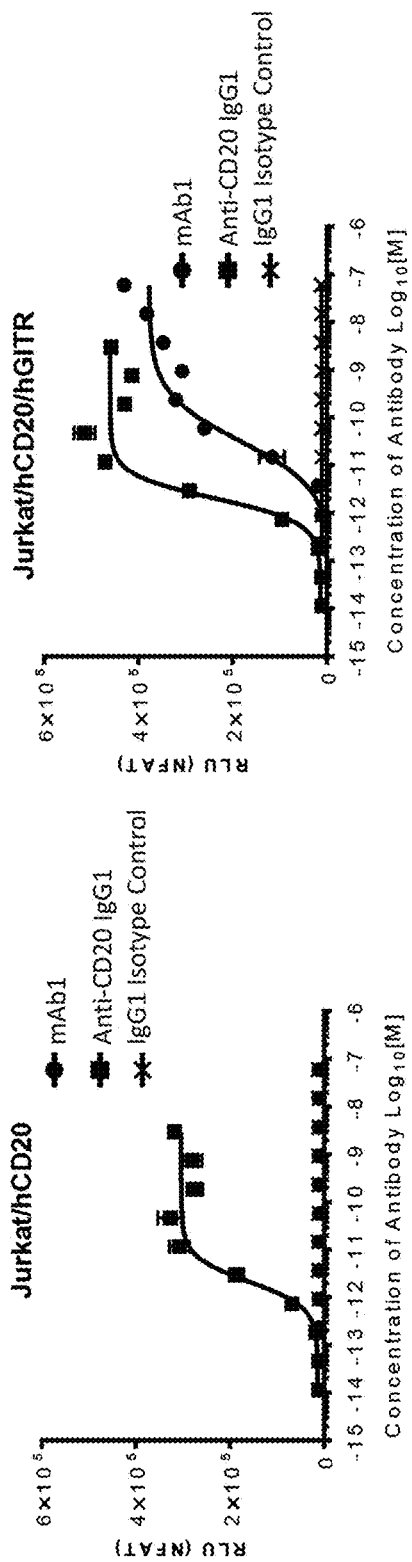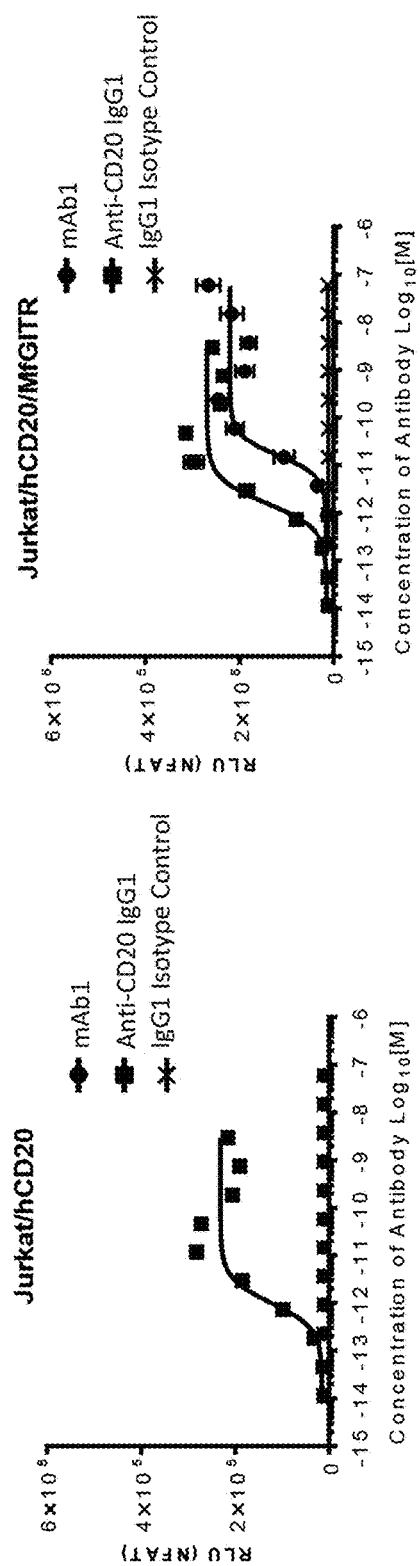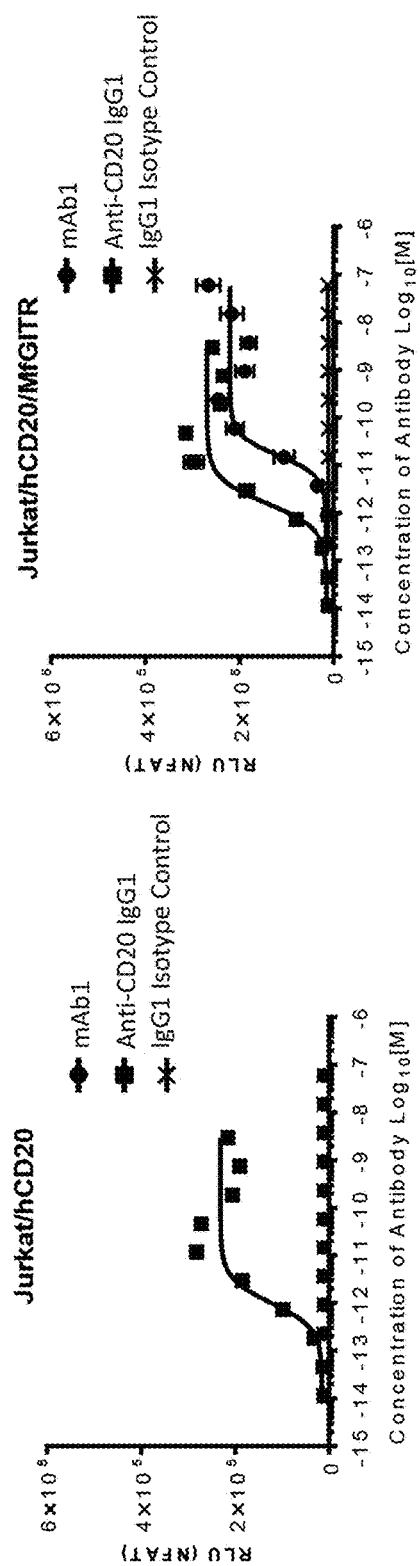

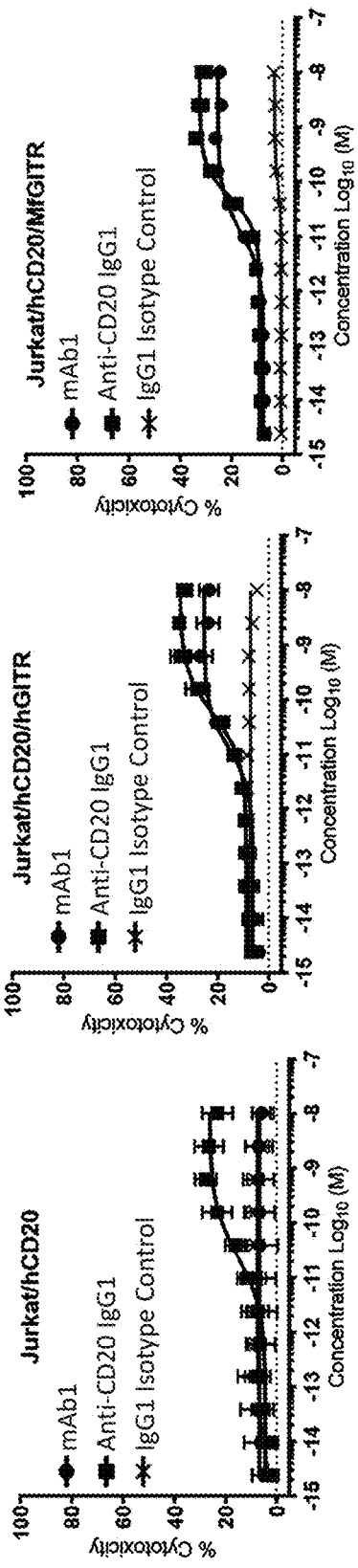
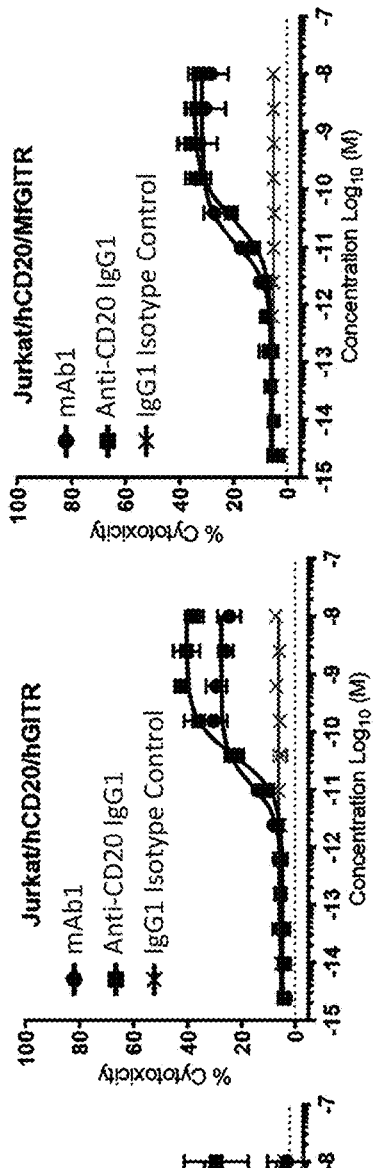
Antibody Mediation of ADCC Against Jurkat T Cells Engineered to Express Human or Cynomolgus Monkey GITR
Fig. 9A — Jurkat/hCD20
Fig. 9B — Donor 6700R Human Primary NK Cells in the Presence of Jurkat/hCD20/hGITR
Fig. 9C — Jurkat/hCD20/MfGITR
Fig. 9D — Jurkat/hCD20
Fig. 9E — Donor 6500V Human Primary NK Cells in the Presence of Jurkat/hCD20/hGITR
Fig. 9F — Jurkat/hCD20/MfGITR

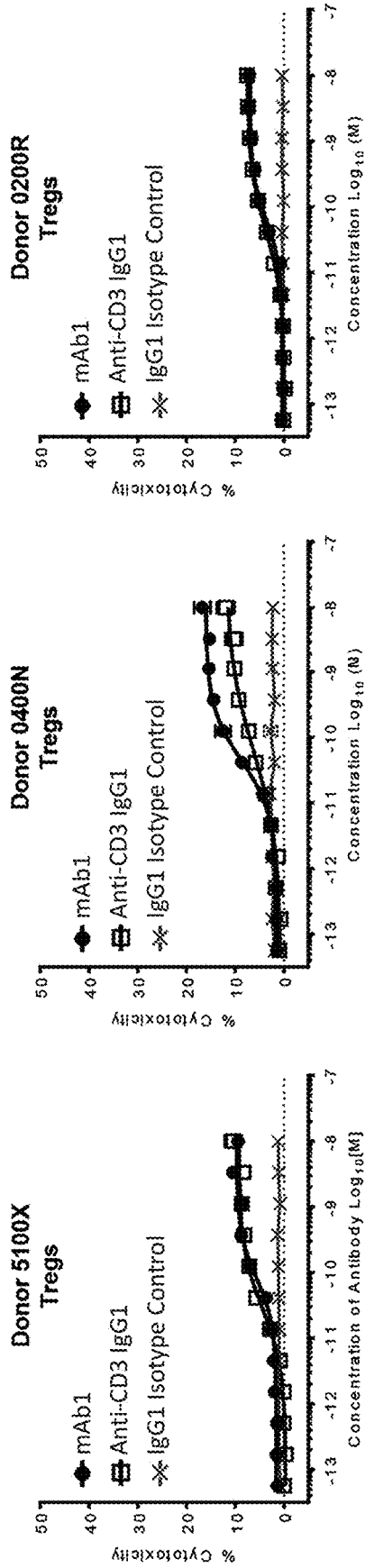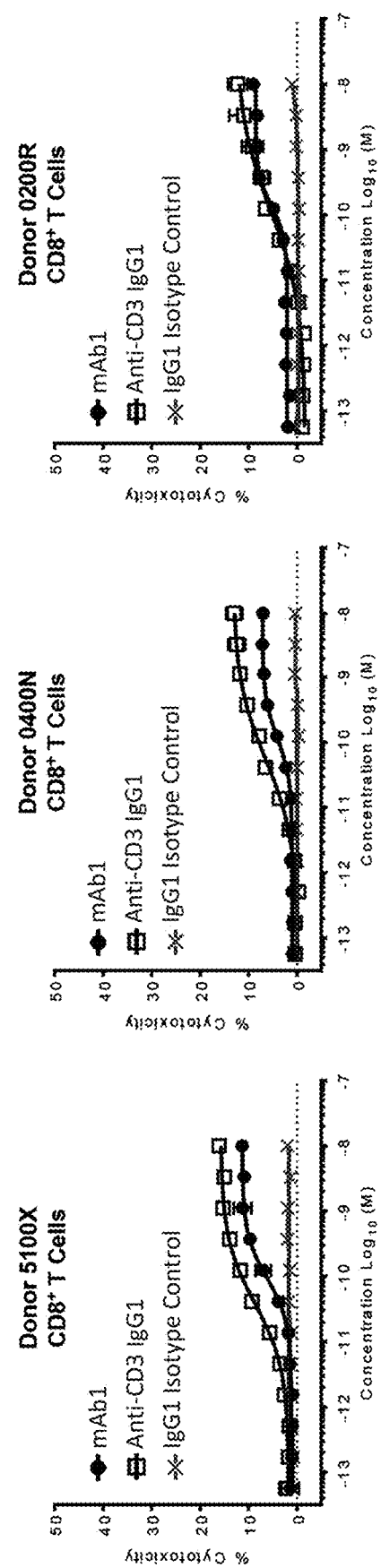
Fig. 10C
Fig. 10D

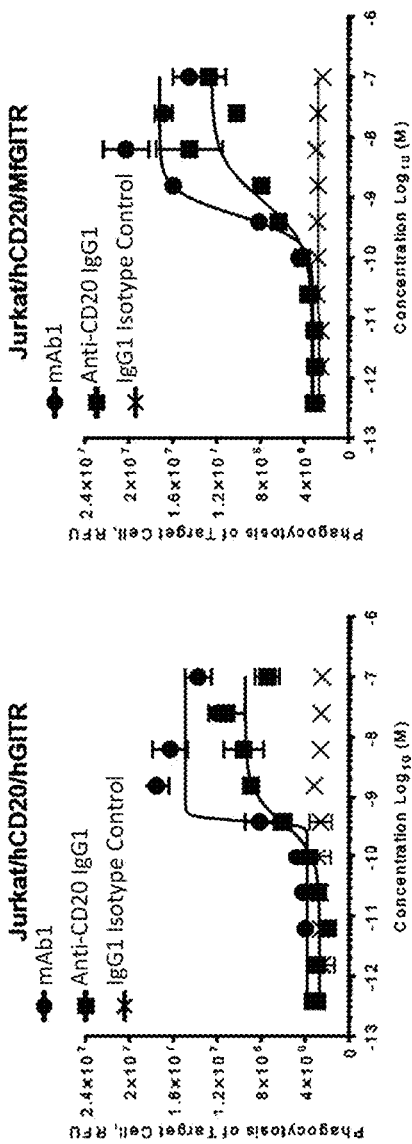
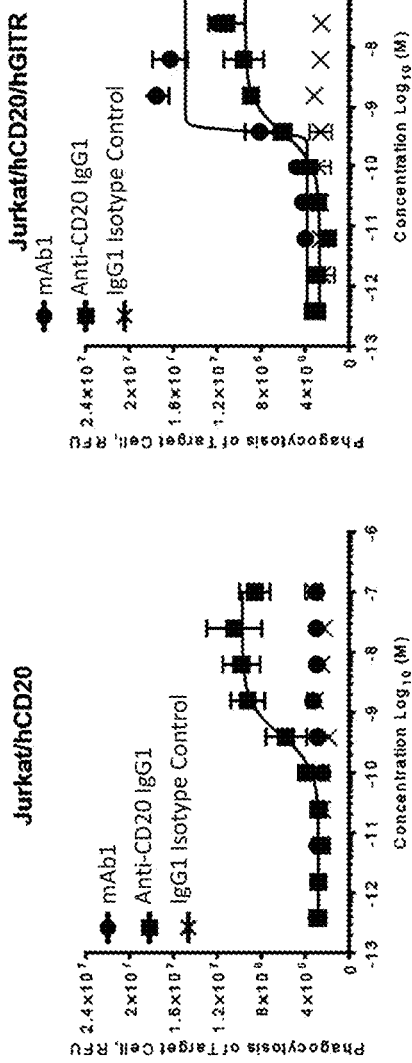
Fig. 11A  Fig. 11B  Fig. 11C
Antibody Mediation of ADCP of Jurkat T Cells Engineered to Express Human or Cynomolgus Monkey GITR

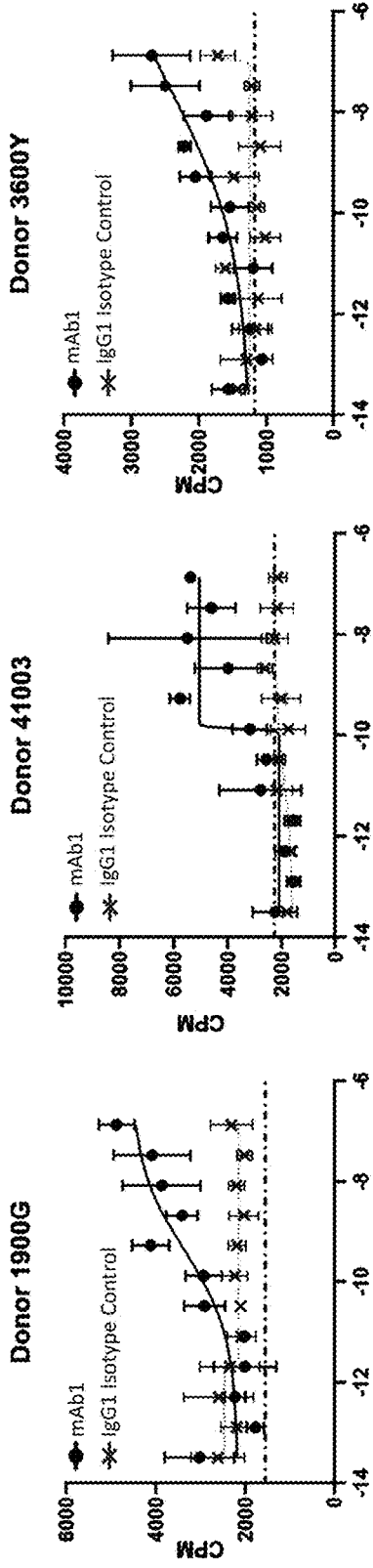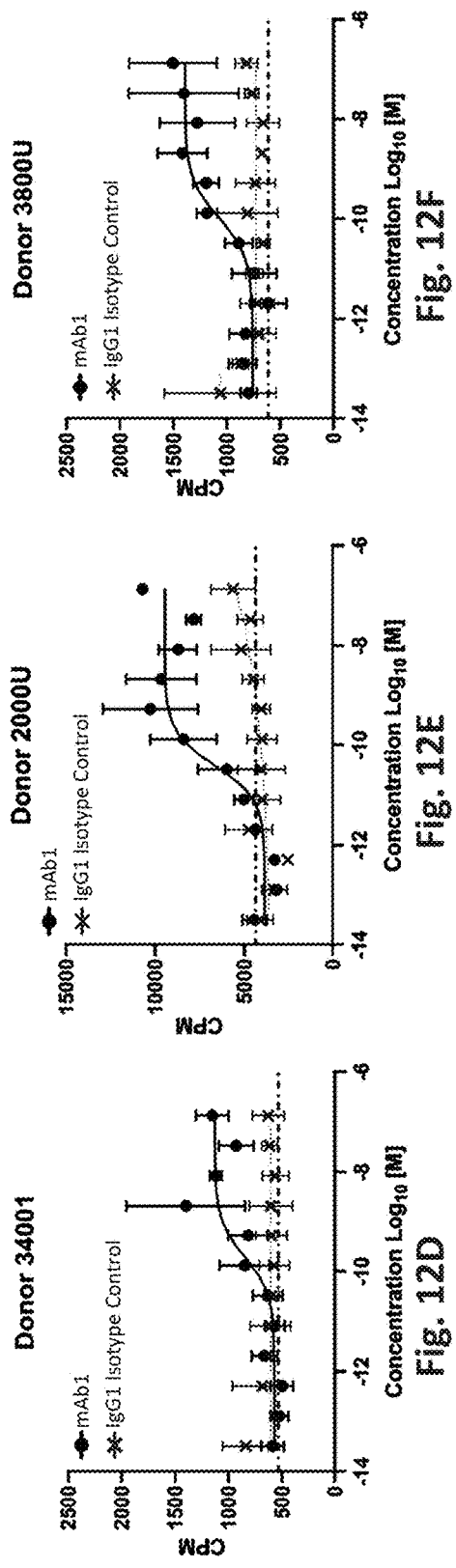

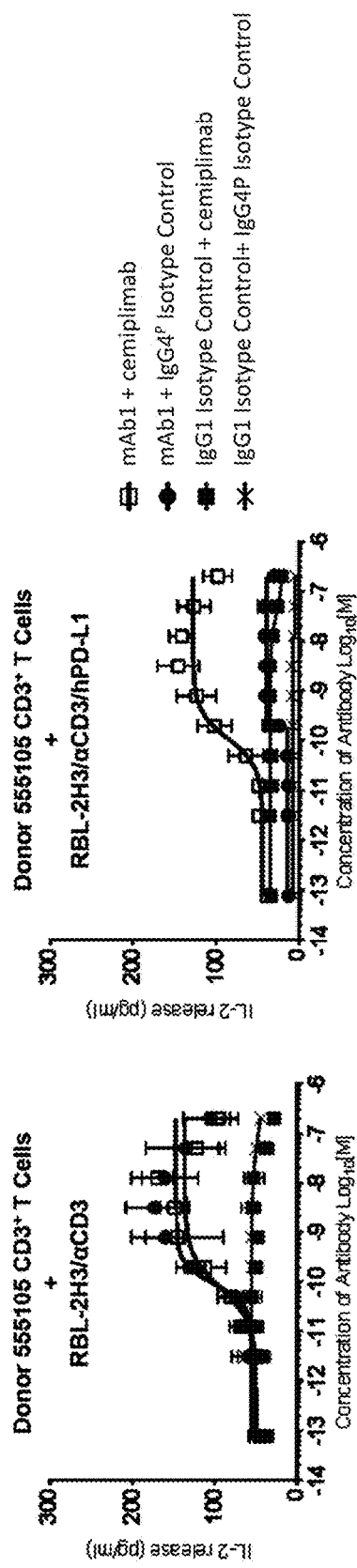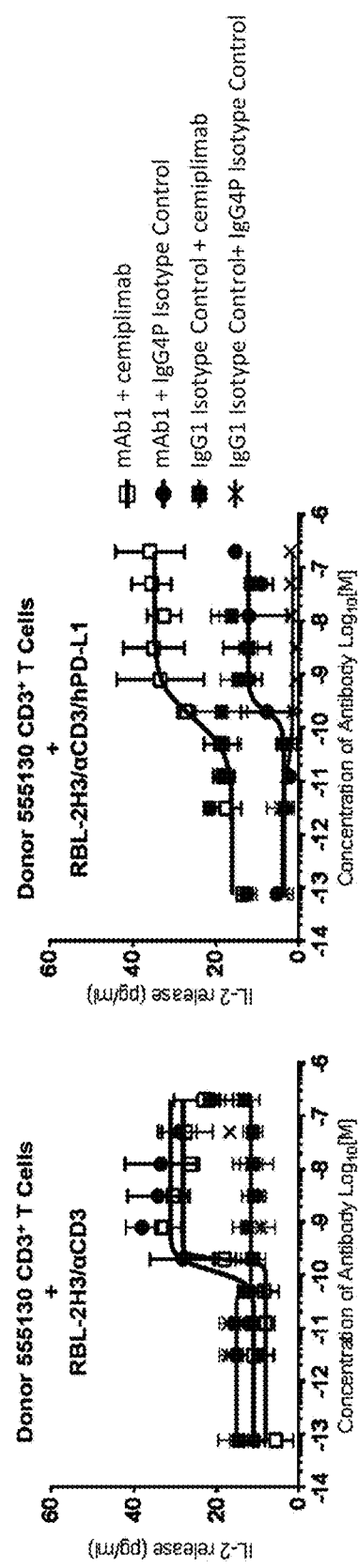
Fig. 16A
Fig. 16B

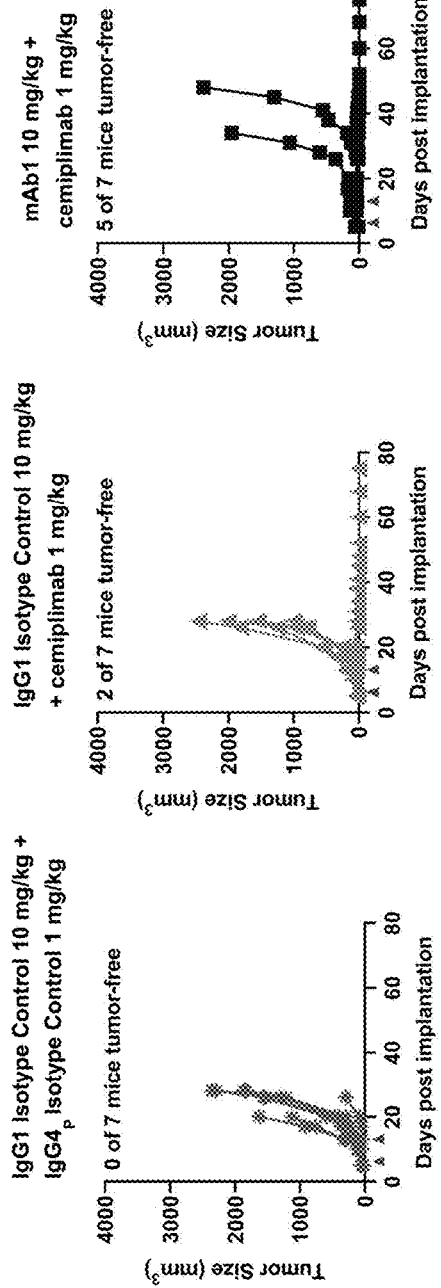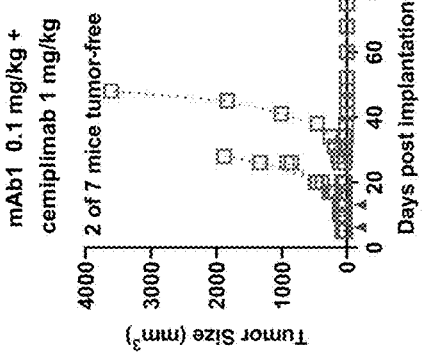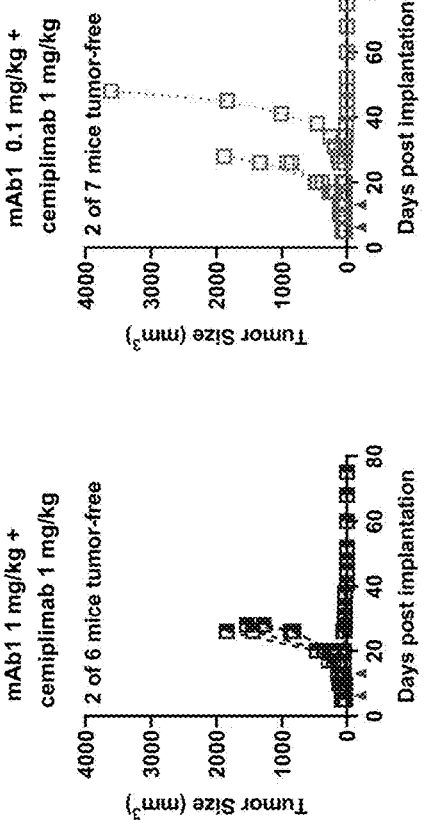

THERAPEUTIC USES OF ANTI-GITR ANTIBODIES

RELATED APPLICATIONS

This application is a divisional application of U.S. patent application Ser. No. 17/193,586, filed on Mar. 5, 2021, which claims priority under 35 U.S.C. § 119(e) of U.S. Provisional Application No. 62/986,494 filed Mar. 6, 2020, the disclosure of which is herein incorporated by reference in its entirety.

FIELD

The present disclosure relates to antibodies and antigen-binding fragments thereof that specifically bind glucocorticoid-induced tumor necrosis factor receptor (GITR) and methods of use thereof.

SEQUENCE LISTING

An official copy of the sequence listing is submitted concurrently with the specification electronically via Patent Center. The contents of electronic sequence listing (10671US02_Sequence_Listing_ST26.xml; Size: 73,838 bytes; and Date of Creation: Sep. 6, 2023) is part of the specification and is herein incorporated by reference in its entirety.

BACKGROUND

Glucocorticoid-induced tumor necrosis factor receptor (GITR) is a member of the tumor necrosis factor receptor superfamily (TNFRSF). GITR expression is constitutively high on regulatory T-cells, low/intermediate on naïve T-cells, NK cells and granulocytes, and inducible upon activation. GITR interacts with its ligand GITRL, which is mainly expressed on antigen-presenting cells. GITR receptor activation can both augment effector T-cell proliferation and function as well as attenuate the suppression induced by regulatory T-cells. Consequently, the modulation of GITR activity can serve as a basis for cancer immunotherapy and immune disorders. Thus, there is a need for agents, e.g., antibodies, that modulate the activity of GITR.

BRIEF SUMMARY

The present disclosure provides antibodies and antigen-binding fragments thereof that bind glucocorticoid-induced tumor necrosis factor receptor (GITR). The antibodies provided herein are useful, inter alia, for targeting immune cells, e.g., effector T-cells, regulatory T-cells, and natural killer (NK) cells that express GITR. The antibodies are particularly useful in that in vivo truncation of the antibody is minimized.

The antibodies provided herein can be full-length (for example, an IgG1 or IgG4 antibody) or may comprise only an antigen-binding portion (for example, a Fab, F(ab')$_2$ or scFv fragment), and may be modified to affect functionality, e.g., to eliminate residual effector functions (Reddy et al., 2000, J. Immunol. 164:1925-1933).

Exemplary anti-GITR antibodies provided herein are listed in Tables 7, 8, and 9. Table 7 sets forth the amino acid sequence identifiers of the heavy chain variable regions (HCVRs), light chain variable regions (LCVRs), heavy chain complementarity determining regions (HCDR1, HCDR2 and HCDR3), and light chain complementarity determining regions (LCDR1, LCDR2 and LCDR3) of the exemplary anti-GITR antibodies. Table 8 sets forth the nucleic acid sequence identifiers of the HCVRs, LCVRs, HCDR1, HCDR2 HCDR3, LCDR1, LCDR2 and LCDR3 of the exemplary anti-GITR antibodies. Table 9 provides the sequence identifiers for the full length heavy and light chain sequences of the exemplary anti-GITR antibodies.

The present disclosure provides antibodies or antigen-binding fragments thereof that specifically bind GITR, wherein the antibody or antigen-binding fragment thereof comprises three heavy chain complementarity determining regions (HCDR1, HCDR2, and HCDR3) within a heavy chain variable region (HCVR) amino acid sequence selected from the group consisting of SEQ ID NOs: 22, 28, 34, and 40; and three light chain complementarity determining regions (LCDR1, LCDR2, and LCDR3) within a light chain variable region (LCVR) amino acid sequence of SEQ ID NO: 10.

The present disclosure provides antibodies or antigen-binding fragments thereof that specifically bind GITR, wherein the antibody or antigen-binding fragment thereof comprises an HCVR amino acid sequence selected from the group consisting of SEQ ID NOs: 22, 28, 34, and 40; and an LCVR amino acid sequence of SEQ ID NO: 10.

The present disclosure provides antibodies or antigen-binding fragments thereof that specifically bind GITR, wherein the antibody comprises a heavy chain amino acid sequence selected from the group consisting of SEQ ID NOs: 26, 32, 38, and 44; and a light chain amino acid sequence of SEQ ID NO: 20.

The present disclosure provides antibodies or antigen-binding fragments thereof that specifically bind GITR, wherein the antibody or antigen-binding fragment thereof comprises three heavy chain CDRs within an HCVR amino acid sequence of SEQ ID NO: 2 modified with N101D, N101E, N101S, or N101T mutation; and three light chain CDRs within an LCVR amino acid sequence of SEQ ID NO: 10.

The present disclosure provides antibodies or antigen-binding fragments thereof that specifically bind GITR, wherein the antibody or antigen-binding fragment thereof comprises three heavy chain CDRs within an HCVR amino acid sequence of SEQ ID NO: 2 modified with N101A, N101F, N101G, N101H, N101I, N101K, N101L, N101M, N101P, N101Q, N101R, N101V, N101W, or N101Y mutation; and three light chain CDRs within an LCVR amino acid sequence of SEQ ID NO: 10.

The present disclosure provides antibodies or antigen-binding fragments thereof that specifically bind GITR, wherein the antibody or antigen-binding fragment thereof comprises three heavy chain CDRs within an HCVR amino acid sequence of SEQ ID NO: 2 modified with S103A, S103D, S103E, S103F, S103G, S103H, S1031, S103K, S103L, S103M, S103N, S103P, S103Q, S103R, S103T, S103V, S103W, or S103Y mutation; and three light chain CDRs within an LCVR amino acid sequence of SEQ ID NO: 10.

Explicitly excluded is the antibody provided in Table 1 herein and disclosed in U.S. 2017/0355774A1, wherein the antibody lacks an N101 or S103 modification or mutation in the HCVR.

The present disclosure provides antibodies or antigen-binding fragments thereof that specifically bind GITR, comprising an HCVR and an LCVR, wherein the HCVR comprises an HCDR3 amino acid sequence selected from any of the HCDR3 amino acid sequences listed in Table 7. The HCVR can further comprise an amino acid sequence selected from any of the HCVR amino acid sequences listed in Table 7, or a substantially similar sequence thereof having at least 90%, at least 95%, at least 98% or at least 99% sequence identity thereto. The LCVR can comprise an LCVR amino acid sequence listed in Table 7, or a substantially similar sequence thereof having at least 90%, at least 95%, at least 98% or at least 99% sequence identity thereto.

The present disclosure also provides antibodies or antigen-binding fragments thereof that specifically bind GITR, comprising an HCVR and an LCVR amino acid sequence pair (HCVR/LCVR) comprising the HCVR amino acid sequences listed in Table 7 paired with the LCVR amino acid sequence listed in Table 7. According to certain embodiments, the present disclosure provides antibodies, or antigen-binding fragments thereof, comprising an HCVR/LCVR amino acid sequence pair contained within any of the exemplary anti-GITR antibodies listed in Table 7. In certain embodiments, the HCVR/LCVR amino acid sequence pair is selected from the group consisting of SEQ ID NOs: 22/10, 28/10, 34/10, and 40/10.

The present disclosure also provides antibodies or antigen-binding fragments thereof that specifically bind GITR, comprising a heavy chain CDR3 (HCDR3) comprising an amino acid sequence selected from any of the HCDR3 amino acid sequences listed in Table 7.

The present disclosure also provides antibodies or antigen-binding fragments thereof that specifically bind GITR, comprising an HCDR3 and an LCDR3 amino acid sequence pair (HCDR3/LCDR3) comprising any of the HCDR3 amino acid sequences listed in Table 7 paired with the LCDR3 amino acid sequence provided in Table 7. According to certain embodiments, the present disclosure provides antibodies, or antigen-binding fragments thereof, comprising an HCDR3/LCDR3 amino acid sequence pair contained within any of the exemplary anti-GITR antibodies listed in Table 7. In certain embodiments, the HCDR3/LCDR3 amino acid sequence pair is selected from the group consisting of SEQ ID NOs: 24/16, 30/16, 36/16, and 42/16.

The present disclosure also provides antibodies or antigen-binding fragments thereof that specifically bind GITR, comprising a set of six CDRs (i.e., HCDR1-HCDR2-HCDR3-LCDR1-LCDR2-LCDR3) contained within any of the exemplary anti-GITR antibodies listed in Table 7. In certain embodiments, the HCDR1-HCDR2-HCDR3-LCDR1-LCDR2-LCDR3 amino acid sequences set is selected from the group consisting of SEQ ID NOs: 4-6-24-12-14-16, 4-6-30-12-14-16, 4-6-36-12-14-16, and 4-6-42-12-14-16.

In a related embodiment, the present disclosure provides antibodies, or antigen-binding fragments thereof that specifically bind GITR, comprising a set of six CDRs (i.e., HCDR1-HCDR2-HCDR3-LCDR1-LCDR2-LCDR3) contained within an HCVR/LCVR amino acid sequence pair as defined by any of the exemplary anti-GITR antibodies listed in Table 7. For example, the present disclosure includes antibodies or antigen-binding fragments thereof that specifically bind GITR, comprising the HCDR1-HCDR2-HCDR3-LCDR1-LCDR2-LCDR3 amino acid sequences set contained within an HCVR/LCVR amino acid sequence pair selected from the group consisting of SEQ ID NOs: 24/16, 30/16, 36/16, and 42/16.

The present disclosure also provides nucleic acid molecules encoding anti-GITR antibodies or portions thereof. For example, the present disclosure provides nucleic acid molecules encoding any of the HCVR amino acid sequences listed in Table 7; in certain embodiments the nucleic acid molecule comprises a polynucleotide sequence selected from any of the HCVR nucleic acid sequences listed in Table 8, or a substantially similar sequence thereof having at least 90%, at least 95%, at least 98% or at least 99% sequence identity thereto.

The present disclosure also provides nucleic acid molecules encoding the LCVR amino acid sequence listed in Table 7; in certain embodiments the nucleic acid molecule comprises a polynucleotide sequence of the LCVR nucleic acid sequence listed in Table 8, or a substantially similar sequence thereof having at least 90%, at least 95%, at least 98% or at least 99% sequence identity thereto.

The present disclosure also provides nucleic acid molecules encoding any of the HCDR3 amino acid sequences listed in Table 7; in certain embodiments the nucleic acid molecule comprises a polynucleotide sequence selected from any of the HCDR3 nucleic acid sequences listed in Table 8, or a substantially similar sequence thereof having at least 90%, at least 95%, at least 98% or at least 99% sequence identity thereto.

The present disclosure also provides nucleic acid molecules encoding an HCVR, wherein the HCVR comprises a set of three CDRs (i.e., HCDR1-HCDR2-HCDR3), wherein the HCDR1-HCDR2-HCDR3 amino acid sequence set is as defined by any of the exemplary anti-GITR antibodies listed in Table 7.

The present disclosure also provides nucleic acid molecules encoding both an HCVR and an LCVR, wherein the HCVR comprises an amino acid sequence of any of the HCVR amino acid sequences listed in Table 7, and wherein the LCVR comprises an amino acid sequence of any of the LCVR amino acid sequences listed in Table 7. In certain embodiments, the nucleic acid molecule comprises a polynucleotide sequence selected from any of the HCVR nucleic acid sequences listed in Table 8, or a substantially similar sequence thereof having at least 90%, at least 95%, at least 98% or at least 99% sequence identity thereto, and a polynucleotide sequence selected from any of the LCVR nucleic acid sequences listed in Table 8, or a substantially similar sequence thereof having at least 90%, at least 95%, at least 98% or at least 99% sequence identity thereto. In certain embodiments according to this aspect provided herein, the nucleic acid molecule encodes an HCVR and LCVR, wherein the HCVR and LCVR are both derived from the same anti-GITR antibody listed in Table 7.

The present disclosure also provides recombinant expression vectors capable of expressing a polypeptide comprising a heavy or light chain variable region of an anti-GITR antibody. For example, the present disclosure includes recombinant expression vectors comprising any of the nucleic acid molecules mentioned above, i.e., nucleic acid molecules encoding any of the HCVR, LCVR, and/or CDR sequences as set forth in Table 7. Also included within the scope of the present disclosure are host cells, for example, eukaryotic host cells, such as mammalian host cells, into which such vectors have been introduced. Exemplary eukaryotic host cells include yeast and mammalian cells, for example vertebrate cells such as a mouse, rat, monkey or human cell line, for example, HKB11 cells, PER.C6 cells, HEK cells or CHO cells. Also provided herein are methods of producing the antibodies or portions thereof by culturing the host cells under conditions permitting production of the antibodies or antibody fragments, and recovering the antibodies and antibody fragments so produced.

The present disclosure includes anti-GITR antibodies having a modified glycosylation pattern. In some embodiments, modification to remove undesirable glycosylation sites may be useful, or an antibody lacking a fucose moiety present on the oligosaccharide chain, for example, to increase antibody dependent cellular cytotoxicity (ADCC) function (see Shield et al. (2002) JBC 277:26733). In other applications, modification of galactosylation can be made in order to modify complement dependent cytotoxicity (CDC).

In another aspect, the disclosure provides a pharmaceutical composition comprising a recombinant human antibody or fragment thereof which specifically binds GITR and a pharmaceutically acceptable carrier. In a related aspect, the disclosure features a composition which is a combination of an anti-GITR antibody and a second therapeutic agent. In one embodiment, the second therapeutic agent is any agent that is advantageously combined with an anti-GITR antibody. The present disclosure also provides antibody-drug conjugates (ADCs) comprising an anti-GITR antibody conjugated to a cytotoxic agent. Exemplary combination therapies, co-formulations, and ADCs involving the anti-GITR antibodies of the present disclosure are disclosed elsewhere herein.

In yet another aspect, the disclosure provides pharmaceutical compositions comprising a recombinant human antibody or fragment thereof which specifically binds GITR for use in the manufacture of a medicament for killing tumor cells or for inhibiting or attenuating tumor cell growth, or otherwise treating a patient afflicted with cancer. In some aspects, the pharmaceutical compositions are therapeutically combined with a second therapeutic agent. In some aspects, the second therapeutic agent is a PD-1 inhibitor. In some aspects, the PD-1 inhibitor is cemiplimab.

In yet another aspect, the disclosure provides therapeutic methods for killing tumor cells or for inhibiting or attenuating tumor cell growth, or otherwise treating a patient afflicted with cancer, using an anti-GITR antibody or antigen-binding portion of an antibody provided herein. The therapeutic methods according to this aspect provided herein comprise administering a therapeutically effective amount of a pharmaceutical composition comprising an antibody or antigen-binding fragment of an antibody provided herein to a subject in need thereof. The disorder treated is any disease or condition which is improved, ameliorated, inhibited, or prevented by targeting GITR and/or by increasing T-cell proliferation or function and/or inhibiting suppression activity induced by regulatory T-cells. In some aspects, the methods further comprise administering a second therapeutic agent to the patient, or subject in need thereof. In some aspects, the second therapeutic agent is a PD-1 inhibitor. In some aspects, the PD-1 inhibitor is cemiplimab.

In yet another aspect, the disclosure provides the use of a recombinant human antibody or fragment thereof which specifically binds GITR, or a pharmaceutical composition comprising the antibody or antigen-binding fragment thereof, for use in the manufacture of a medicament for killing tumor cells or for inhibiting or attenuating tumor cell growth, or otherwise treating a patient afflicted with cancer.

In yet another aspect, the disclosure provides therapeutic methods for killing tumor cells or for inhibiting or attenuating tumor cell growth, or otherwise treating a patient afflicted with cancer, using a combination of an anti-GITR antibody or antigen-binding portion of an anti-GITR antibody and an anti-PD1 antibody or antigen-binding portion of an anti-PD1 antibody. In some aspects, the anti-PD1 antibody is cemiplimab. The therapeutic methods according to this aspect provided herein comprise administering a therapeutically effective amount of a pharmaceutical composition comprising a combination of an anti-GITR and anti-PD1 antibody or antigen-binding fragment composition to a subject in need thereof. The disorder treated is any disease or condition which is improved, ameliorated, inhibited or prevented by targeting both GITR and PD1.

In yet another aspect, the disclosure provides methods for treating cancer comprising administering, to a subject in need thereof, (i) an anti-GITR antibody or antigen-binding fragment thereof comprising a HCDR1 comprising an amino acid sequence of SEQ ID NO: 4, HCDR2 comprising an amino acid sequence of SEQ ID NO: 6, HCDR3 comprising an amino acid sequence of SEQ ID NO: 24, LCDR1 comprising an amino acid sequence of SEQ ID NO: 12, LCDR2 comprising an amino acid sequence of SEQ ID NO: 14, and LCDR3 comprising an amino acid sequence of SEQ ID NO: 16; and (ii) cemiplimab. In some aspects, the cancer is selected from the group consisting of squamous cell skin cancer, cutaneous squamous cell carcinoma (CSCC), myeloma, lung cancer, melanoma, head and neck squamous cell carcinoma (SCCHN), small cell lung cancer, non-small cell lung cancer (NSCLC), cervical cancer, e.g. cervical squamous cell carcinoma (cervical SCC), breast cancer, and renal cell carcinoma (RCC), adenocarcinoma, colorectal cancer (CRC), pancreatic carcinoma, head and neck cancer, prostate cancer, glioblastoma multiforme, malignant gliomas, osteosarcoma, colorectal cancer, gastric cancer (e.g., gastric cancer with MET amplification), malignant mesothelioma, multiple myeloma, ovarian cancer, synovial sarcoma, thyroid cancer, breast cancer, including triple negative breast cancer, testicular cancer, esophageal cancer, uterine cancer, endometrial cancer, liver cancer, immune checkpoint blockade (ICB) naïve cancer, and ICB experienced cancer.

In yet another aspect, the disclosure provides methods for the use of an anti-GITR antibody or antigen-binding fragment thereof comprising an HCDR1 comprising an amino acid sequence of SEQ ID NO: 4, an HCDR2 comprising an amino acid sequence of SEQ ID NO: 6, an HCDR3 comprising an amino acid sequence of SEQ ID NO: 24, an LCDR1 comprising an amino acid sequence of SEQ ID NO: 12, an LCDR2 comprising an amino acid sequence of SEQ ID NO: 14, and an LCDR3 comprising an amino acid sequence of SEQ ID NO: 16, in the manufacture of a medicament for use in a method of treating cancer in a subject in need thereof. The methods comprise administering to the subject the anti-GITR antibody or antigen-binding fragment thereof and cemiplimab. In some aspects, the cancer is selected from the group consisting of squamous cell skin cancer, cutaneous squamous cell carcinoma (CSCC), myeloma, lung cancer, melanoma, head and neck squamous cell carcinoma (SCCHN), small cell lung cancer, non-small cell lung cancer (NSCLC), cervical cancer, e.g. cervical squamous cell carcinoma (cervical SCC), breast cancer, and renal cell carcinoma (RCC), adenocarcinoma, colorectal cancer (CRC), pancreatic carcinoma, head and neck cancer, prostate cancer, glioblastoma multiforme, malignant gliomas, osteosarcoma, colorectal cancer, gastric cancer (e.g., gastric cancer with MET amplification), malignant mesothelioma, multiple myeloma, ovarian cancer, synovial sarcoma, thyroid cancer, breast cancer, including triple negative breast cancer, testicular cancer, esophageal cancer, uterine cancer, endometrial cancer, liver cancer, immune checkpoint blockade (ICB) naïve cancer, and ICB experienced cancer.

In yet another embodiment, the disclosure provides an anti-GITR antibody or antigen-binding fragment thereof for use in a method of treating cancer in a subject in need thereof, the method comprising administering to the subject: (i) the anti-GITR antibody or antigen-binding fragment thereof comprising an HCDR1 comprising an amino acid sequence of SEQ ID NO: 4, an HCDR2 comprising an amino acid sequence of SEQ ID NO: 6, an HCDR3 comprising an amino acid sequence of SEQ ID NO: 24, an LCDR1 comprising an amino acid sequence of SEQ ID NO: 12, an LCDR2 comprising an amino acid sequence of SEQ ID NO: 14, and an LCDR3 comprising an amino acid sequence of SEQ ID NO: 16; and (ii) cemiplimab. In some aspects, the cancer is selected from the group consisting of squamous cell skin cancer, cutaneous squamous cell carcinoma (CSCC), myeloma, lung cancer, melanoma, head and neck squamous cell carcinoma (SCCHN), small cell lung cancer, non-small cell lung cancer (NSCLC), cervical cancer, e.g. cervical squamous cell carcinoma (cervical SCC), breast cancer, and renal cell carcinoma (RCC), adenocarcinoma, colorectal cancer (CRC), pancreatic carcinoma, head and neck cancer, prostate cancer, glioblastoma multiforme, malignant gliomas, osteosarcoma, colorectal cancer, gastric cancer (e.g., gastric cancer with MET amplification), malignant mesothelioma, multiple myeloma, ovarian cancer, synovial sarcoma, thyroid cancer, breast cancer, including triple negative breast cancer, testicular cancer, esophageal cancer, uterine cancer, endometrial cancer, liver cancer, immune checkpoint blockade (ICB) naïve cancer, and ICB experienced cancer.

Other embodiments will become apparent from a review of the ensuing detailed description.

BRIEF DESCRIPTION OF THE DRAWINGS

FIG. 8A, FIG. 8B, FIG. 8C, and FIG. 8D depict Fc-mediated NFAT activity in Jurkat/NFAT-Luc/hFcγR3a and Jurkat/NFAT-Luc/MfFcγR3a effector cells. Jurkat/NFAT-Luc/hFcγR3a and Jurkat/NFAT-Luc/MfFcγR3a were incubated with mAb1 or an IgG1 isotype control at 916fM to 60 nM or an anti-CD20 IgG1 at 45.8fM to 3 nM, including a no antibody control, and Jurkat/hCD20 (FIGS. 8A, 8C) or Jurkat/hCD20/hGITR (FIG. 8B) or Jurkat/hCD20/MfGITR (FIG. 8D) cells (1:2 ratio of effector to target cells). Signaling in Jurkat/NFAT-Luc/hFcγR3a and Jurkat/NFAT-Luc/MfFcγR3a cells was detected as luciferase activity and measured by the quantification of luminescence signal, reported as relative light units (RLU). Data are from an assay performed in duplicate wells and are plotted as mean±SD.

FIG. 9A, FIG. 9B, FIG. 9C, FIG. 9D, FIG. 9E, and FIG. 9F depict antibody mediation of ADCC against Jurkat T-cells engineered to express human or cynomolgus monkey GITR. Jurkat/hCD20 (FIGS. 9A, 9D), Jurkat/hCD20/hGITR (FIGS. 9B, 9E), or Jurkat/hCD20/MfGITR (FIGS. 9C, 9F) target cells were incubated with human NK cells (5:1 ratio of effector to target cells) and mAb1, an IgG1 isotype control, and an anti-CD20 IgG1 at concentrations ranging from 9.5fM to 10 nM for 3.5 hours. Cytotoxicity was determined using the commercially available CYTOTOX-GLO™ assay, which is a luminescent cytotoxicity assay that measures the relative number of dead cells in cell populations using a luminescence-readout. The dotted line in each graph denotes the level of nonspecific cytotoxicity observed upon addition of NK cells in the absence of antibody. Data from an assay performed in triplicate wells are plotted as mean±SD.

FIG. 10A, FIG. 10B, FIG. 10C, and FIG. 10D depict antibody mediation of ADCC against human primary T-cells. Human primary Tregs (FIGS. 10A, 10C) and CD8$^+$ T-cells (FIGS. 10B, 10D) (target cells) were isolated from PBMC (3 donors), stimulated and expanded in culture, and incubated with human primary NK cells (effector cells) isolated from whole blood (2 donors) (5:1 ratio of effector to target cells). mAb1, an IgG1 isotype control, or an anti-CD3 IgG1 at concentrations ranging from 169fM to 10 nM were incubated with effector and target cells for 3.5 hours. Cytotoxicity was determined using the commercially available CYTOTOX-GLO™ assay, which is a luminescent cytotoxicity assay that measures the relative number of dead cells in cell populations. The dotted line in each graph denotes the level of nonspecific cytotoxicity observed upon addition of NK cells in the absence of antibody. Data from an assay performed in triplicate wells are plotted as mean±SD.

FIG. 11A, FIG. 11B, and FIG. 11C depict antibody mediation of ADCP of Jurkat T-cells engineered to express human or cynomolgus monkey GITR. Jurkat/hCD20 (FIG. 11A), Jurkat/hCD20/hGITR (FIG. 11B), or Jurkat/hCD20/MfGITR (FIG. 11C) target cells labeled with CELL-TRACE® CFSE dye were incubated with human primary monocyte-derived phagocytes labeled with CELLTRACE® Far Red dye and mAb1, an IgG1 isotype control, or an anti-CD20 IgG1 at concentrations ranging from 381fM to 100 nM, including a no antibody control, for 1 to 2 hours. Phagocytosis was analyzed by fluorescence imaging on an OPERA PHOENIX® High-Content Screening System and was measured as the green fluorescence intensity (target cells labelled with CFSE, detected in the 488 nm emission channel) within far red-labeled population of cells (phagocytes labeled with Far Red dye, detected in the 647 nm emission channel), reported in relative fluorescence units (RFU). Data from an assay performed in duplicate wells are plotted as mean±SD.

FIG. 12A, FIG. 12B, FIG. 12C, FIG. 12D, FIG. 12E, and FIG. 12F depict anti-GITR antibody effect on anti-CD3-mediated primary CD4+ T-cell proliferation. Enriched human primary T-cells (6 donors) were incubated with serial dilutions of mAb1 or IgG1 isotype control at a range of concentrations (32fM to 133 nM), including a no antibody control, in the presence of a fixed concentration (2 nM) of stimulatory anti-CD3 and HEK293/FcγR2b accessory cells. Data are from an assay performed in triplicate wells and are plotted as mean±SD. T-cell proliferation was measured via detection of tritium decay (from tritiated thymidine incorporated into dividing cells) and reported as CPM. The dotted line in each graph denotes the level of proliferation observed upon addition of stimulatory anti-CD3 in the absence of titrated antibody.

FIG. 16A and FIG. 16B depict enhanced IL-2 release from anti-CD3-stimulated primary CD3+T cells, from Donor 555105 (FIG. 16A) and Donor 555130 (FIG. 16B), treated with Cemiplimab in the presence of human PD-L1. Enriched human primary T cells were incubated with serial dilutions of mAb1 or IgG1 isotype control in the presence of a fixed concentration (20 nM) cemiplimab or an IgG4$^P$ isotype control at a range of concentrations (76fM to 200 nM) in the presence RBL-2H3/aCD3 or RBL-2H3/aCD3/hPD-L1 at an antigen-presenting cell to T-cell ratio of 1:2. Data are from an assay performed in triplicate wells and are plotted as mean±SD. IL-2 release was measured using the Human IL-2 Kit from PERKINELMER® according to the manufacturer's protocol.

FIG. 19A, FIG. 19B, FIG. 19C, FIG. 19D, and FIG. 19E demonstrate higher frequency of MC38 tumor clearance in mice treated with 1 mg/kg cemiplimab in combination with 0.1 mg/kg (FIG. 19E), 1.0 mg/kg (FIG. 19D), and 10 mg/kg mAb1 (FIG. 19C) relative to cemiplimab alone (FIG. 19B). Treatment with isotype controls is shown in FIG. 19A.

DETAILED DESCRIPTION

Figure 1:
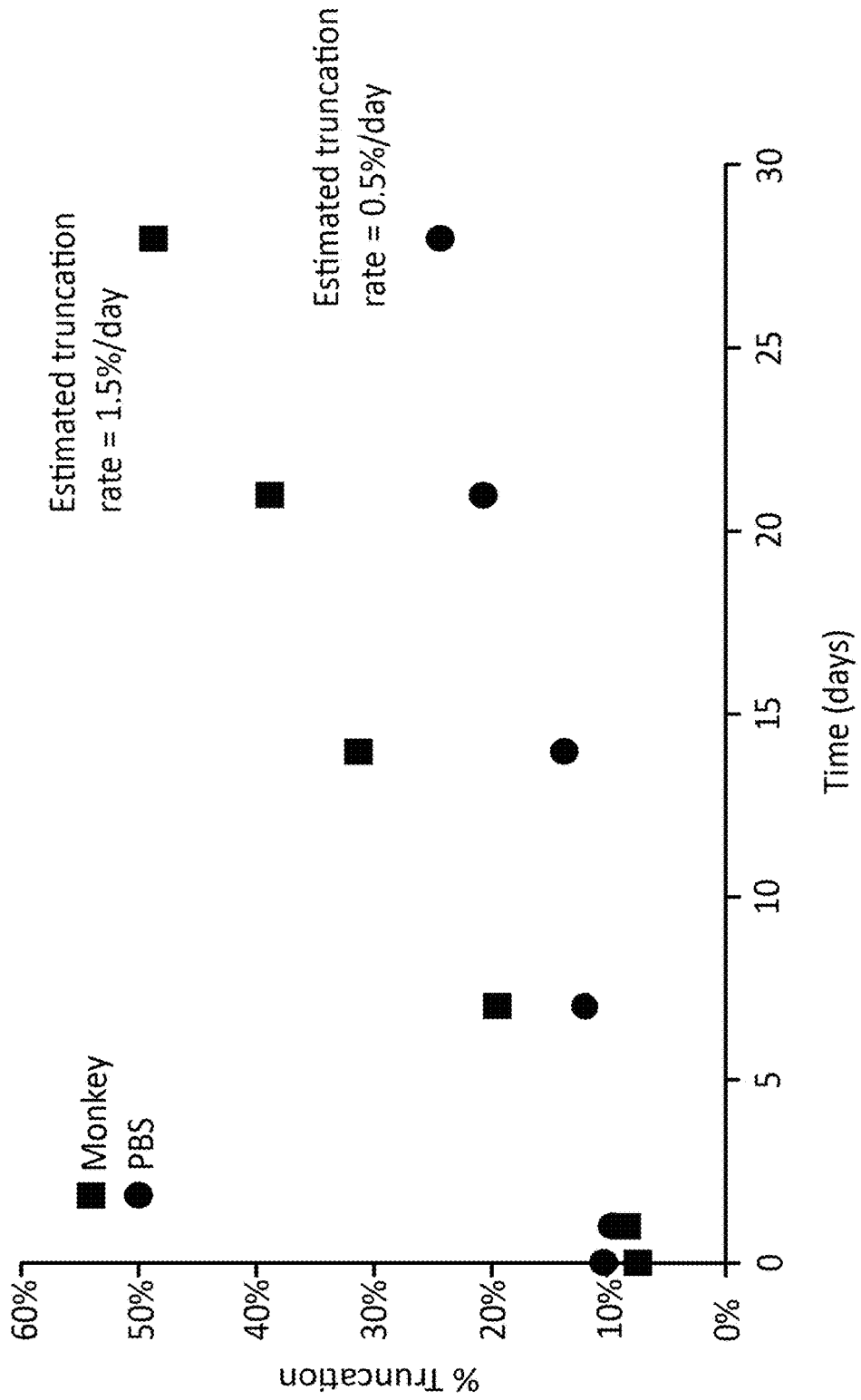
FIG. 1 depicts increase in truncation observed in CompAb1 when incubated in monkey serum or PBS. Estimated truncation rate in monkey serum was approximately 1.5%/day and in PBS was approximately 0.5%/day.

Modulation of the tumor microenvironment by targeting intratumoral immune cells is a therapeutic approach for cancer treatment. Specifically, targeting costimulatory and coinhibitory immune checkpoint receptors expressed on the cell surface of intratumoral T-cells can boost endogenous anti-tumor responses by enhancing cytotoxicity against tumor cells and down regulating local immune suppression.

Tumor necrosis factor receptor superfamily member 18 (TNFRSF18), also known as glucocorticoid-induced tumor necrosis factor receptor-related protein (GITR), is a costimulatory receptor that is expressed on regulatory T-cells (Tregs) and non-Tregs, referred to as conventional T-cells, as well as other cells of the immune system. GITR is expressed at low levels on resting T-cells and upregulated following T-cell activation, with higher expression on activated Tregs than activated conventional T-cells (Shimizu et al., Nature Immunology, 23(2): 135-142, 2002) (Krausz et al., The Scientific World Journal, 7: 533-66, 2007) (Knee et al., European Journal of Cancer, 67: 1-10, 2016). The differential expression profile of GITR on activated Tregs makes it an attractive target for preferential depletion of activated intratumoral Tregs to promote anti-tumor immunity.

mAb1 and mAb2 are human IgG1 GITR agonist antibodies that preferentially deplete activated Tregs. GITR agonist antibodies can induce anti-tumor immunity by preferentially depleting intratumoral Tregs in an FcγR-dependent manner (e.g., antibody-dependent cellular cytotoxicity/phagocytosis [ADCC/ADCP]), which correlates with GITR cell-surface expression. These GITR antibodies can synergize with programmed cell death-1 (PD-1) checkpoint blockade, leading to long-term anti-tumor responses in preclinical models. In some aspects, an anti-GITR antibody is combined with a PD-1 inhibitor, for example, cemiplimab. While not wishing to be held to theory, the PD-1 inhibitor may restore the ability of the anti-GITR antibody to enhance anti-CD3-stimulated T-cell activation. In some aspects, therapeutically combining an anti-GITR antibody disclosed herein with a PD-1 inhibitor results in greater reduction in tumor growth compared to the PD-1 inhibitor alone. In some aspects, therapeutically combining an anti-GITR antibody disclosed herein with a PD-1 inhibitor results in higher frequency of tumor clearance relative to the PD-1 inhibitor alone. In some aspects, therapeutically combining an anti-GITR antibody disclosed herein with a PD-1 inhibitor results in greater survival in a tumor bearing subject compared to the PD-1 inhibitor alone.

Before the present disclosure is described, it is to be understood that this disclosure is not limited to particular methods and experimental conditions described, as such methods and conditions may vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present disclosure, the preferred methods and materials are now described. All patents, applications and non-patent publications mentioned in this specification are incorporated herein by reference in their entireties.

Glucocorticoid-Induced Tumor Necrosis Factor Receptor

The expression glucocorticoid-induced tumor necrosis factor receptor, "GITR," and the like, as used herein, refers to the human glucocorticoid-induced tumor necrosis factor receptor, comprising the amino acid sequence as set forth in SEQ ID NO: 49 (NCBI Accession #NP_004186.1). The expression "GITR" includes both monomeric and multimeric GITR molecules. As used herein, the expression "monomeric human GITR" means a GITR protein or portion thereof that does not contain or possess any multimerizing domains and that exists under normal conditions as a single GITR molecule without a direct physical connection to another GITR molecule. An exemplary monomeric GITR molecule is the molecule referred to herein as "hGITR.mmh" comprising the amino acid sequence of SEQ ID NO: 45 (see, e.g., Example 3, herein). As used herein, the expression "dimeric human GITR" means a construct comprising two GITR molecules connected to one another through a linker, covalent bond, non-covalent bond, or through a multimerizing domain such as an antibody Fc domain. Exemplary dimeric GITR molecules include those molecules referred to herein as "hGITR.mFc" and "hGITR.hFc", comprising the amino acid sequence of SEQ ID NO: 46 and SEQ ID NO: 47 respectively.

All references to proteins, polypeptides and protein fragments herein are intended to refer to the human version of the respective protein, polypeptide or protein fragment unless explicitly specified as being from a non-human species. Thus, the expression "GITR" means human GITR unless specified as being from a non-human species, e.g., "mouse GITR," "monkey GITR," etc.

As used herein, the expression "cell surface-expressed GITR" means one or more GITR protein(s), or the extracellular domain thereof, that is/are expressed on the surface of a cell in vitro or in vivo, such that at least a portion of a GITR protein is exposed to the extracellular side of the cell membrane and is accessible to an antigen-binding portion of an antibody. A "cell surface-expressed GITR" can comprise or consist of a GITR protein expressed on the surface of a cell which normally expresses GITR protein. Alternatively, "cell surface-expressed GITR" can comprise or consist of GITR protein expressed on the surface of a cell that normally does not express human GITR on its surface but has been artificially engineered to express GITR on its surface.

Antibodies and Antigen-Binding Fragments of Antibodies

The term "antibody", as used herein, means any antigen-binding molecule or molecular complex comprising at least one complementarity determining region (CDR) that specifically binds to or interacts with a particular antigen (e.g., GITR). The term "antibody" includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments provided herein, the FRs of the anti-GITR antibody (or antigen-binding portion thereof) may be identical to the human germline sequences, or may be naturally or artificially modified. An amino acid consensus sequence may be defined based on a side-by-side analysis of two or more CDRs.

In certain embodiments provided herein, the anti-GITR antibodies provided herein are human antibodies. The term "human antibody", as used herein, is intended to include antibodies having variable and constant regions derived from human germline immunoglobulin sequences. The human antibodies provided herein may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences. The term "human antibody" does not include naturally occurring molecules that normally exist without modification or human intervention/manipulation, in a naturally occurring, unmodified living organism.

As used herein, the expression "anti-GITR antibody" includes both monovalent and monospecific bivalent antibodies with a single specificity, as well as bispecific antibodies comprising a first arm that binds GITR and a second arm that binds a second (target) antigen, wherein the anti- GITR arm comprises any of the HCVR/LCVR or CDR sequences as set forth in Table 7 herein. The expression "anti-GITR antibody" also includes antibody-drug conjugates (ADCs) comprising an anti-GITR antibody or antigen-binding portion thereof conjugated to a drug or toxin (i.e., cytotoxic agent). The expression "anti-GITR antibody" also includes antibody-radionuclide conjugates (ARCs) comprising an anti-GITR antibody or antigen-binding portion thereof conjugated to a radionuclide.

The antibodies provided herein may, in some embodiments, be recombinant human antibodies. The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

The term "specifically binds," or "binds specifically to", or the like, means that an antibody or antigen-binding fragment thereof forms a complex with an antigen that is relatively stable under physiologic conditions. Specific binding can be characterized by an equilibrium dissociation constant of at least about $1 \times 10^{-8}$ M or less (e.g., a smaller $K_D$ denotes a tighter binding). Methods for determining whether two molecules specifically bind are well known in the art and include, for example, equilibrium dialysis, surface plasmon resonance, and the like. As described herein, antibodies have been identified by real-time, label free bio-layer interferometry assay on an Octet® HTX biosensor, which bind specifically to GITR. Moreover, multi-specific antibodies that bind to one domain in GITR and one or more additional antigens or a bi-specific that binds to two different regions of GITR are nonetheless considered antibodies that "specifically bind", as used herein.

The term "high affinity" antibody refers to those monoclonal antibodies having a binding affinity to hGITR, expressed as $K_D$, of at least $10^{-8}$ M; at least about $10^{-9}$ M; at least about $10^{-10}$ M; or at least about $10^{-10}$ M, as measured by real-time, label free bio-layer interferometry assay, e.g., an Octet® HTX biosensor, or by surface plasmon resonance, e.g., BIACORE®, or by solution-affinity ELISA®.

By the term "slow off rate", "Koff" or "kd" is meant an antibody that dissociates from GITR, with a rate constant of $1 \times 10^{-3}$ s$^{-1}$ or less, or $1 \times 10^{-4}$ s$^{-1}$ or less, as determined by real-time, label free bio-layer interferometry assay, e.g., an Octet® HTX biosensor, or by surface plasmon resonance, e.g., BIACORE®.

The term "$K_D$", as used herein, is intended to refer to the equilibrium dissociation constant of a particular antibody-antigen interaction.

The antibodies provided herein may be isolated antibodies. An "isolated antibody," as used herein, means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody" for purposes of the present disclosure. An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals.

The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The terms "antigen-binding fragment" of an antibody, or "antibody fragment", as used herein, refers to one or more fragments of an antibody that retain the ability to bind to The term "antibody", as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present disclosure include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$-$C_L$; (viii) $V_L$-$C_H1$; (ix) $V_L$-$C_H2$; (X) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present disclosure may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present disclosure using routine techniques available in the art.

Human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification.

The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al. (1993) Molecular Immunology 30:105) to levels typically observed using a human IgG1 hinge. The instant invention encompasses antibodies having one or more mutations in the hinge, $C_H2$ or $C_H3$ region which may be desirable, for example, in production, to improve the yield of the desired antibody form.

Modifications to Antibodies and Antigen-Binding Fragments Thereof

The anti-GITR antibodies disclosed herein may comprise one or more amino acid substitutions, insertions and/or deletions in the framework and/or CDR regions of the heavy and light chain variable domains as compared to the sequences of the antibodies provided herein, or may be naturally or artificially modified. In certain embodiments, the framework regions of the antibody (or antigen binding fragment thereof) may be identical to the human germline sequences, for example, identical to the sequences of the antibodies provided herein, or may be naturally or artificially modified. One or more amino acids in a given framework region (or one or more framework regions) can be substituted, and the substitution(s) can be conservative or non-conservative substitutions. Substitution of one or more CDR residues or omission of one or more CDRs is also possible. Antibodies have been described in the scientific literature in which one or two CDRs can be dispensed with for binding. Padlan et al. (1995 FASEB J. 9:133-139) analyzed the contact regions between antibodies and their antigens, based on published crystal structures, and concluded that only about one fifth to one third of CDR residues actually contact the antigen. Padlan also found many antibodies in which one or two CDRs had no amino acids in contact with an antigen (see also, Vajdos et al. 2002 J Mol Biol 320:415-428). Thus, the antibodies provided herein can be effectively modified in the CDR regions and/or the framework regions, as long as the modified antibody maintains one or more desirable characteristics, e.g. the antibody or antigen-binding fragment thereof binds to hGITR an $EC_{50}$ of less than about $10^{-9}$ M; and/or demonstrates a decrease in truncation rate, as compared to an antibody lacking the N101 or S103 modification.

Modifications to a given CDR can be made relative to a CDR sequence from an antibody provided herein, and the modifications can include conservative or non-conservative substitutions. Desirable substitutions can be determined by molecular modeling and/or empirically. For example, one or more CDR residues can be substituted with an amino acid occupying the corresponding position in another human antibody sequence or a consensus of such sequences.

Furthermore, an antigen-binding fragment thereof can be an antibody disclosed herein but modified to omit one or more CDRs and/or one or more framework regions, as long as the modified antibody (a.k.a., antigen-binding fragment) maintains binding to hGITR.

CDR residues not contacting antigen can be identified based on previous studies (for example, residues H60-H65 in HCDR2 are often not required), from regions of Kabat CDRs lying outside Chothia CDRs, by molecular modeling, and/or empirically. An antibody or antigen-binding fragment thereof provided herein can be modified to remove or replace a given CDR, particularly one that does not contact antigen. Light chain CDRs can be replaced with, for example, universal light chain CDRs.

The fully human anti-GITR monoclonal antibodies provided herein may comprise one or more amino acid substitutions, insertions and/or deletions in the framework and/or CDR regions of the heavy and light chain variable domains as compared to the corresponding germline sequences, or as compared to the sequences provided herein. Such modifications or mutations can be readily ascertained by comparing the amino acid sequences disclosed herein to germline sequences available from, for example, public antibody sequence databases, or by comparing the amino acid sequences to those of the antibodies provided herein, for example, any one of the antibody sequences provided in Table 7.

The present disclosure includes antibodies, and antigen-binding fragments thereof, which are derived from any of the amino acid sequences disclosed herein, wherein one or more amino acids within one or more framework regions and/or CDRs are modified, as long as the modified antibody maintains one or more desirable characteristics, e.g. the antibody or antigen-binding fragment thereof binds to hGITR with an $EC_{50}$ of less than about $10^{-9}$ M; and/or demonstrates a decrease in truncation rate in vivo or in vitro. Once obtained, antibodies and antigen-binding fragments that contain one or more modifications to a framework region and/or CDR can be easily tested for one or more desired properties such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present disclosure.

The present disclosure includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present disclosure may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present disclosure.

The present disclosure also includes anti-GITR antibodies comprising variants of any of the HCVR, LCVR, and/or CDR amino acid sequences disclosed herein having one or more conservative substitutions. For example, the present disclosure includes anti-GITR antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences set forth in Table 7 herein.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 95%, and more preferably at least about 96%, 97%, 98% or 99% of the nucleotide bases, as measured by any well-known algorithm of sequence identity, such as FASTA, BLAST or Gap, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% sequence identity. In some aspects, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331, herein incorporated by reference. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443-1445, herein incorporated by reference. A "moderately conservative" replacement is any change having a nonnegative value in the PAM250 log-likelihood matrix.

Sequence identity and/or similarity for polypeptides is typically measured using sequence analysis software. Protein analysis software matches similar sequences using measures of similarity assigned to various substitutions, deletions and other modifications, including conservative amino acid substitutions. For instance, GCG software contains programs such as Gap and Bestfit which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Sequences also can be compared using the Smith-Waterman homology search algorithm using an affine gap search with a gap open penalty of 12 and a gap extension penalty of 2, BLOSUM matrix of 62. Another preferred algorithm when comparing a sequence provided herein to a database containing a large number of sequences from different organisms is the computer program BLAST, especially BLASTP or TBLASTN, using default parameters. See, e.g., Altschul et al. (1990) J. Mol. Biol. 215:403-410 and Altschul et al. (1997) Nucleic Acids Res. 25:3389-402, each herein incorporated by reference.

Anti-GITR Antibodies Comprising N101 or S103 Modifications

According to certain embodiments of the present disclosure, anti-GITR antibodies or antigen-binding fragments thereof are provided which have an N101 or S103 modification in the HCVR. Such a modification provides the disclosed antibodies with desirable characteristics in stability in vitro and in vivo.

Explicitly excluded is the antibody provided in Table 1 herein and disclosed in U.S. 2017/0355774, which lacks an N101 or S103 modification or mutation in the HCVR.

In some aspects, provided herein are isolated antibodies or antigen-binding fragment thereof of having an N101 or S103 modification in the HCVR. An anti-GITR antibody or antigen-binding fragment thereof having such modification can further exhibit one or more properties selected from the group consisting of:

(a) has a truncation rate in human, monkey, or mouse serum of less than 0.5% per day; and (b) has an in vivo truncation rate in mouse of about 0%.

Truncation rates can be determined by, for example, assays described in Examples 2, 5, and 6.

In some aspects, the anti-GITR antibody or antigen-binding fragment thereof can comprise three heavy chain complementarity determining regions (HCDR1, HCDR2, and HCDR3) within a heavy chain variable region (HCVR) amino acid sequence selected from the group consisting of SEQ ID NOs: 22, 28, 34, and 40; and three light chain complementarity determining regions (LCDR1, LCDR2, and LCDR3) within a light chain variable region (LCVR) amino acid sequence of SEQ ID NO: 10.

In some aspects, the anti-GITR antibody or antigen-binding fragment thereof can comprise an HCVR amino acid sequence selected from the group consisting of SEQ ID NOs: 22, 28, 34, and 40; and an LCVR amino acid sequence of SEQ ID NO: 10.

In some aspects, the anti-GITR antibody can comprise a heavy chain amino acid sequence selected from the group consisting of SEQ ID NOs: 26, 32, 38, and 44; and a light chain amino acid sequence of SEQ ID NO: 20.

In some aspects, the anti-GITR antibody or antigen-binding fragment thereof can comprise three heavy chain CDRs within an HCVR amino acid sequence of SEQ ID NO: 2 modified with N101A, N101F, N101G, N101H, N101I, N101K, N101L, N101M, N101P, N101Q, N101R, N101V, N101W, or N101Y mutation; and three light chain CDRs within an LCVR amino acid sequence of SEQ ID NO: 10. For example, the anti-GITR antibody or antigen-binding fragment thereof can comprise three heavy chain CDRs within an HCVR amino acid sequence of SEQ ID NO: 2 modified with N101D, N101E, N101S, or N101T mutation; and three light chain CDRs within an LCVR amino acid sequence of SEQ ID NO: 10.

In some aspects, the anti-GITR antibody or antigen-binding fragment thereof can comprise three heavy chain CDRs within an HCVR amino acid sequence of SEQ ID NO: 2 modified with S103A, S103D, S103E, S103F, S103G, S103H, S1031, S103K, S103L, S103M, S103N, S103P, S103Q, S103R, S103T, S103V, S103W, or S103Y mutation; and three light chain CDRs within an LCVR amino acid sequence of SEQ ID NO: 10.

Explicitly excluded is the antibody provided in Table 1 herein and disclosed in U.S. 2017/0355774. This antibody lacks an N101 or S103 modification or mutation in the HCVR.

Anti-GITR Antibodies Comprising Fc Variants

According to certain embodiments of the present disclosure, anti-GITR antibodies are provided comprising an Fc domain comprising one or more mutations which enhance or diminish antibody binding to the FcRn receptor, e.g., at acidic pH as compared to neutral pH. For example, the present disclosure includes anti-GITR antibodies comprising a mutation in the $C_H2$ or a $C_H3$ region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antibody when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., H/F or Y); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 2591 (e.g., V2591), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P).

For example, the present disclosure includes anti-GITR antibodies comprising an Fc domain comprising one or more pairs or groups of mutations selected from the group consisting of: 250Q and 248L (e.g., T250Q and M248L); 252Y, 254T and 256E (e.g., M252Y, S254T and T256E); 428L and 434S (e.g., M428L and N434S); and 433K and 434F (e.g., H433K and N434F). All possible combinations of the foregoing Fc domain mutations, and other mutations within the antibody variable domains disclosed herein, are contemplated within the scope of the present disclosure.

Biological Characteristics of the Anti-GITR Antibodies

The present disclosure includes antibodies and antigen-binding fragments thereof that bind monomeric human GITR with high affinity. For example, the present disclosure includes anti-GITR antibodies that bind monomeric human GITR (e.g., hGITR.mmh) with a $K_D$ of less than about 12.0 nM as measured by surface plasmon resonance at 25° C., e.g., using an assay format as defined in Example 3 herein using purified antibodies, or a substantially similar assay. In some embodiments, anti-GITR antibodies are provided that bind monomeric human GITR at 25° C. with a $K_D$ of less than about 12 nM, less than about 10 nM, less than about 5 nM, or less than about 2.0 nM as measured by surface plasmon resonance, e.g., using an assay format as defined in Example 3 herein, or a substantially similar assay. The present disclosure also includes anti-GITR antibodies that bind monomeric human GITR with a $K_D$ of less than about 110 nM, less than about 90 nM, less than about 70 nm, less than about 50 nM, less than about 25 nM, or less than about 15 nM, as measured by surface plasmon resonance at 25° C. using an assay format as provided in Example 3 herein, where the antibodies are secreted in conditioned culture.

The present disclosure also includes antibodies and antigen-binding fragments thereof that bind monomeric human GITR (e.g., hGITR.mmh) with a dissociative half-life (t ½) of greater than about 2 minutes as measured by surface plasmon resonance at 25° C., e.g., using an assay format as defined in Example 3 herein, or a substantially similar assay. According to certain embodiments, anti-GITR antibodies are provided that bind monomeric human GITR at 25° C. with a t½ of greater than about 2 minutes, greater than about 4 minutes, greater than about 6 minutes, greater than about 7 minutes, or longer, as measured by surface plasmon resonance, e.g., using an assay format as defined in Example 3 herein, or a substantially similar assay.

The present disclosure also includes antibodies and antigen-binding fragments thereof that bind dimeric human GITR (e.g., hGITR.mFc) with high affinity. For example, the present disclosure includes anti-GITR antibodies that bind dimeric human GITR with a $K_D$ of less than about 1 nM as measured by surface plasmon resonance at 25° C., e.g., using an assay format as defined in Example 3 herein using purified antibodies, or a substantially similar assay. According to certain embodiments, anti-GITR antibodies are provided that bind dimeric human GITR at 25° C. with a $K_D$ of less than about 1 nM, less than about 900 pM, less than about 800 pM, less than about 700 pM, less than about 600 pM, less than about 500 pM, less than about 400 pM, less than about 300 pM, less than about 200 pM, less than about 100 pM as measured by surface plasmon resonance, e.g., using an assay format as defined in Example 3 herein, or a substantially similar assay. The present disclosure also includes anti-GITR antibodies that bind dimeric human GITR with a $K_D$ of less than about 5 nM, less than about 1 nM, less than about 300 pM, or less than about 100 pM, as measured by surface plasmon resonance at 25° C. using an assay format as provided in Example 3 herein, where the antibodies are secreted in conditioned culture.

The present disclosure also includes antibodies and antigen-binding fragments thereof that bind dimeric human GITR (e.g., hGITR.mFc) with a dissociative half-life (t ½) of greater than about 4 minutes as measured by surface plasmon resonance at 25° C., e.g., using an assay format as defined in Example 3 herein, or a substantially similar assay. According to certain embodiments, anti-GITR antibodies are provided that bind dimeric human GITR at 25° C. with a t½ of greater than about 4 minutes, greater than about 9 minutes, greater than about 10 minutes, greater than about 35 minutes, or greater than about 70 minutes, or longer, as measured by surface plasmon resonance, e.g., using an assay format as defined in Example 3 herein, or a substantially similar assay.

The present disclosure also includes antibodies and antigen-binding fragments thereof that bind Jurkat/hCD20 target cells expressing human or monkey GITR. For example, antibodies that bind to human GITR or monkey GITR expressing Jurkat/hCD20 cells with high affinity are provided herein. For example, the instant disclosure includes anti-GITR antibodies that bind human GITR expressing Jurkat/hCD20 target cells with an $EC_{50}$ of less than about 4 nM as measured by mean fluorescent intensity (MFI), e.g., using an assay format as defined in Example 7 herein, or a substantially similar assay. In certain embodiments, anti-GITR antibodies are provided that bind Jurkat/hCD20 target cells expressing human or monkey GITR with an $EC_{50}$ of less than about 4 nM, less than about 3 nM, less than about 2 nM as measured by MFI, e.g., using an assay format as defined in Example 7 herein, or a substantially similar assay.

The present disclosure also includes antibodies and antigen-binding fragments thereof that bind anti-CD3/anti-CD28-stimulated human and cynomolgus monkey primary T-cells. CD25 and CD69 are surrogate markers for human and cynomolgus monkey primary T-cell activation, respectively. For example, antibodies that bind to anti-CD3/anti-CD28-stimulated human and cynomolgus monkey primary T-cells with high affinity are provided herein, using an assay format as defined in Example 8 herein, or a substantially similar assay. In some aspects, the anti-GITR antibody or antigen-binding fragment thereof can be combined with a PD-1 inhibitor such as cemiplimab. While not wishing to be held to theory, in the presence of inhibitory PD-L1/PD1 signaling, cemiplimab may restore the ability of the anti-GITR antibody to enhance anti-CD3-stimulated T-cell activation.

The present disclosure also includes antibodies and antigen-binding fragments thereof that mediate NFAT activation via human or cynomolgus monkey FcγR3a (an Fc-receptor that mediates ADCC and is predominantly expressed on NK cells). For example, antibodies that mediate NFAT activation via human or cynomolgus monkey FcγR3a as evaluated in an ADCC reporter bioassay are provided herein. For example, the instant disclosure includes anti-GITR antibodies that mediate NFAT activation via human or cynomolgus monkey FcγR3a in an ADCC reporter bioassay with an $EC_{50}$ of less than about 32 pM as measured by luminescence, e.g., using an assay format as defined in Example 9 herein, or a substantially similar assay. In certain embodiments, anti-GITR antibodies are provided that mediate NFAT activation via human or cynomolgus monkey FcγR3a with an $EC_{50}$ of less than about 32 pM, or less than about 16 pM, as measured by luminescence, e.g., using an assay format as defined in Example 9 herein, or a substantially similar assay.

The antibodies of the present disclosure may function through complement-dependent cytotoxicity (CDC) or antibody-dependent cell-mediated cytotoxicity (ADCC). "Complement-dependent cytotoxicity" (CDC) refers to lysis of antigen-expressing cells by an antibody provided herein in the presence of complement. "Antibody-dependent cell-mediated cytotoxicity" (ADCC) refers to a cell-mediated reaction in which nonspecific cytotoxic cells that express Fc receptors (FcRs) (e.g., Natural Killer (NK) cells, neutrophils, and macrophages) recognize bound antibody on a target cell and thereby lead to lysis of the target cell. CDC and ADCC can be measured using assays that are well known and available in the art. (See, e.g., U.S. Pat. Nos. 5,500,362 and 5,821,337, and Clynes et al. (1998) Proc. Natl. Acad. Sci. (USA) 95:652-656). The constant region of an antibody is important in the ability of an antibody to fix complement and mediate cell-dependent cytotoxicity. Thus, the isotype of an antibody may be selected on the basis of whether it is desirable for the antibody to mediate cytotoxicity.

The present disclosure also includes antibodies and antigen-binding fragments thereof that mediate ADCC. For example, antibodies that mediate ADCC against Jurkat/hCD20/hGITR and Jurkat/hCD20/MfGITR (target cells) in the presence of human primary NK cells (effector cells) are provided herein. For example, the instant disclosure includes anti-GITR antibodies that mediate ADCC against Jurkat/hCD20/hGITR and Jurkat/hCD20/MfGITR in the presence of human primary NK cells with an $EC_{50}$ of less than about 14 pM as measured by luminescence, e.g., using an assay format as defined in Example 10 herein, or a substantially similar assay. In certain embodiments, mediate ADCC against Jurkat/hCD20/hGITR and Jurkat/hCD20/MfGITR in the presence of human primary NK cells with an $EC_{50}$ of less than about 14 pM, or less than about 13 pM, or less than about 12 pM, or less than about 11 pM, or less than about 10 pM, as measured by luminescence, e.g., using an assay format as defined in Example 10 herein, or a substantially similar assay.

In further example, antibodies that mediate ADCC against human primary T-cells (target cells) in the presence of human primary NK cells (effector cells) are provided herein. For example, the instant disclosure includes anti-GITR antibodies that mediate ADCC against human primary T-cells in the presence of human primary NK cells with a subnanomolar $EC_{50}$ as measured by luminescence, e.g., using an assay format as defined in Example 11 herein, or a substantially similar assay.

The present disclosure also includes antibodies and antigen-binding fragments thereof that mediate ADCP. For example, antibodies that mediate concentration-dependent ADCP of Jurkat/hCD20/hGITR and Jurkat/hCD20/MfGITR (target cells) in the presence of human primary monocyte-derived phagocytes (effector cells) are provided herein. For example, the instant disclosure includes anti-GITR antibodies that mediate concentration-dependent ADCP of Jurkat/hCD20/hGITR and Jurkat/hCD20/MfGITR in the presence of human primary monocyte-derived phagocytes with a subnanomolar $EC_{50}$ as measured by green fluorescence intensity, e.g., using an assay format as defined in Example 12 herein, or a substantially similar assay.

The present disclosure also includes antibodies and antigen-binding fragments thereof that enhance anti-CD3-mediated T-cell proliferation. For example, antibodies that enhance primary $CD4^+$ T-cell proliferation mediated by a stimulatory CD3 antibody in the presence of HEK293/FcγR2b accessory cells are provided herein. For example, the instant disclosure includes anti-GITR antibodies that enhance primary CD4W T-cell proliferation mediated by a stimulatory CD3 antibody in the presence of HEK293/FcγR2b accessory cells with subnanomolar $EC_{50}$ values and with 2.3 to 3.1-fold increases in maximum T-cell proliferation (measured as CPM from tritium decay) above background., e.g., using an assay format as defined in Example 13 herein, or a substantially similar assay.

In some aspects, provided herein are isolated antibodies or antigen-binding fragments thereof of having an N101 or S103 modification in the HCVR amino acid sequence. An anti-GITR antibody or antigen-binding fragment thereof having such modification can further exhibit one or more properties selected from the group consisting of:
(a) binds monomeric human GITR at 25° C. with a $K_D$ of less than about 12 nM as measured by surface plasmon resonance;
(b) binds monomeric human GITR at 25° C. with a t½ of greater than about 2 minutes;
(c) binds dimeric human GITR at 25° C. with a $K_D$ of less than about 1 nM as measured by surface plasmon resonance; and
(d) binds dimeric human GITR at 25° C. with a t½ of greater than about 5 minutes.

In some aspects, provided herein are isolated antibodies or antigen-binding fragments thereof of having an N101 or S103 modification in the HCVR amino acid sequence. An anti-GITR antibody or antigen-binding fragment thereof having such modification can further exhibit one or more properties selected from the group consisting of:
(a) binds cell-surface human and cynomolgus monkey GITR with an $EC_{50}$ of less than about 4 nM;
(b) enhances Fc-mediated NFAT activity in Jurkat/NFAT-Luc/hFcγR3a and/or Jurkat/NFAT-Luc/MfFcγR3a Effector Cells with an $EC_{50}$ of less than about 40 pM;
(c) mediates ADCC against human primary T-cells in the presence of human primary NK cells with an $EC_{50}$ of less than about 20 pM;
(d) mediates ADCP by at least about 5-fold in Jurkat T-cells engineered to express human or cynomolgus monkey GITR relative to non-GITR expressing Jurkat T-cells;
(e) enhances anti-CD3-mediated primary CD4+ T-cell proliferation;
(f) induces anti-tumor immunity by preferentially depleting intratumoral $T_{regs}$ in an FcγR-dependent manner; and
(g) blocks human monomeric GITR binding to human GITR ligand with an $IC_{50}$ of less than about 7 nM.

The antibodies of the present disclosure may possess one or more of the aforementioned biological characteristics, or any combination thereof. The foregoing list of biological characteristics of the antibodies provided herein is not intended to be exhaustive. Other biological characteristics of the antibodies of the present disclosure will be evident to a person of ordinary skill in the art from a review of the present disclosure including the working Examples herein.

Antibodies that Block GITR Binding to GITR Ligand

The present disclosure includes antibodies that block human GITR ligand (hGITRL)-binding to human GITR, e.g., as determined in the assay format described in Example 14 herein.

In some embodiments, the antibodies provided herein block human GITR ligand (hGITRL). In some embodiments, the antibody or antibody-binding fragment thereof blocks human GITR ligand with a blocking percentage greater than about 90% at an $IC_{50}$ less than about 7.0 nM, as described in Example 14 or substantially similar assay format. In some embodiments, the antibody or antibody-binding fragment thereof blocks human GITR ligand with a blocking percentage greater than about 90%, greater than about 95%, or greater than about 98%, at an $IC_{50}$ less than about 10 nM, less than about 7.0 nM, less than about 5.0 nM, or less than about 3.0 nM, as described in Example 14 or substantially similar assay format.

Epitope Mapping and Related Technologies

The term "epitope" refers to an antigenic determinant that interacts with a specific antigen-binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

The epitope to which the antibodies of the present disclosure bind may consist of a single contiguous sequence of 3 or more (e.g., 3, 4, 5, 6, 7, 8, 9, 10, 11, 12, 13, 14, 15, 16, 17, 18, 19, 20 or more) amino acids of a GITR protein. Alternatively, the epitope may consist of a plurality of non-contiguous amino acids (or amino acid sequences) of GITR. In some embodiments, the epitope is located on or near the GITRL-binding domain of GITR. In other embodiments, the epitope is located outside of the GITRL-binding domain of GITR, e.g., at a location on the surface of GITR at which an antibody, when bound to such an epitope, does not interfere with GITRL binding to GITR.

Various techniques known to persons of ordinary skill in the art can be used to determine whether an antibody "interacts with one or more amino acids" within a polypeptide or protein. Exemplary techniques include, e.g., routine cross-blocking assay such as that described Antibodies, Harlow and Lane (Cold Spring Harbor Press, Cold Spring Harb., NY), alanine scanning mutational analysis, peptide blots analysis (Reineke, 2004, Methods Mol Biol 248:443-463), and peptide cleavage analysis. In addition, methods such as epitope excision, epitope extraction and chemical modification of antigens can be employed (Tomer, 2000, Protein Science 9:487-496). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water to allow hydrogen-deuterium exchange to occur at all residues except for the residues protected by the antibody (which remain deuterium-labeled). After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) *Analytical Biochemistry* 267(2):252-259; Engen and Smith (2001) Anal. Chem. 73:256A-265A.

The present disclosure further includes anti-GITR antibodies that bind to the same epitope as any of the specific exemplary antibodies described herein (e.g. antibodies comprising any of the amino acid sequences as set forth in Table 7 herein). Likewise, the present disclosure also includes anti-GITR antibodies that compete for binding to GITR with any of the specific exemplary antibodies described herein (e.g. antibodies comprising any of the amino acid sequences as set forth in Table 7 herein).

One can easily determine whether an antibody binds to the same epitope as, or competes for binding with, a reference anti-GITR antibody by using routine methods known in the art and exemplified herein. For example, to determine if a test antibody binds to the same epitope as a reference anti-GITR antibody provided herein, the reference antibody is allowed to bind to a GITR protein. Next, the ability of a test antibody to bind to the GITR molecule is assessed. If the test antibody is able to bind to GITR following saturation binding with the reference anti-GITR antibody, it can be concluded that the test antibody binds to a different epitope than the reference anti-GITR antibody. On the other hand, if the test antibody is not able to bind to the GITR molecule following saturation binding with the reference anti-GITR antibody, then the test antibody may bind to the same epitope as the epitope bound by the reference anti-GITR antibody provided herein. Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA®, RIA, BIACORE®, flow cytometry or any other quantitative or qualitative antibody-binding assay available in the art. In accordance with certain embodiments of the present disclosure, two antibodies bind to the same (or overlapping) epitope if, e.g., a 1-, 5-, 10-, 20- or 100-fold excess of one antibody inhibits binding of the other by at least 50% but preferably 75%, 90% or even 99% as measured in a competitive binding assay (see, e.g., Junghans et al., Cancer Res. 1990:50:1495-1502). Alternatively, two antibodies are deemed to bind to the same epitope if essentially all amino acid mutations in the antigen that reduce or eliminate binding of one antibody reduce or eliminate binding of the other. Two antibodies are deemed to have "overlapping epitopes" if only a subset of the amino acid mutations that reduce or eliminate binding of one antibody reduce or eliminate binding of the other.

To determine if an antibody competes for binding (or cross-competes for binding) with a reference anti-GITR antibody, the above-described binding methodology is performed in two orientations: In a first orientation, the reference antibody is allowed to bind to a GITR protein under saturating conditions followed by assessment of binding of the test antibody to the GITR molecule. In a second orientation, the test antibody is allowed to bind to a GITR molecule under saturating conditions followed by assessment of binding of the reference antibody to the GITR molecule. If, in both orientations, only the first (saturating) antibody is capable of binding to the GITR molecule, then it is concluded that the test antibody and the reference antibody compete for binding to GITR. As will be appreciated by a person of ordinary skill in the art, an antibody that competes for binding with a reference antibody may not necessarily bind to the same epitope as the reference antibody, but may sterically block binding of the reference antibody by binding an overlapping or adjacent epitope.

Preparation of Human Antibodies

The anti-GITR antibodies of the present disclosure can be fully human antibodies. Methods for generating monoclonal antibodies, including fully human monoclonal antibodies are known in the art. Any such known methods can be used in the context of the present disclosure to make human antibodies that specifically bind to human GITR.

Using VELOCIMMUNE™ technology, for example, or any other similar known method for generating fully human monoclonal antibodies, high affinity chimeric antibodies to GITR are initially isolated having a human variable region and a mouse constant region. As in the experimental section below, the antibodies are characterized and selected for desirable characteristics, including affinity, ligand blocking activity, selectivity, epitope, etc. If necessary, mouse constant regions are replaced with a desired human constant region, for example wild-type or modified IgG1 or IgG4, to generate a fully human anti-GITR antibody. While the constant region selected may vary according to specific use, high affinity antigen-binding and target specificity characteristics reside in the variable region. In certain instances, fully human anti-GITR antibodies are isolated directly from antigen-positive B cells.

Bioequivalents

The anti-GITR antibodies and antibody fragments of the present disclosure encompass proteins having amino acid sequences that vary from those of the described antibodies but that retain the ability to bind human GITR. Such variant antibodies and antibody fragments comprise one or more additions, deletions, or substitutions of amino acids when compared to parent sequence, but exhibit biological activity that is essentially equivalent to that of the described antibodies. Likewise, the anti-GITR antibody-encoding DNA sequences of the present disclosure encompass sequences that comprise one or more additions, deletions, or substitutions of nucleotides when compared to the disclosed sequence, but that encode an anti-GITR antibody or antibody fragment that is essentially bioequivalent to an anti-GITR antibody or antibody fragment provided herein. Examples of such variant amino acid and DNA sequences are discussed above.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single dose or multiple dose. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, and potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of anti-GITR antibodies provided herein may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antibodies may include anti-GITR antibody variants comprising amino acid changes which modify the glycosylation characteristics of the antibodies, e.g., mutations which eliminate or remove glycosylation.

Species Selectivity and Species Cross-Reactivity

The present disclosure, according to certain embodiments, provides anti-GITR antibodies that bind to human GITR but not to GITR from other species. The present disclosure also includes anti-GITR antibodies that bind to human GITR and to GITR from one or more non-human species. For example, the anti-GITR antibodies provided herein may bind to human GITR and may bind or not bind, as the case may be, to one or more of mouse, rat, guinea pig, hamster, gerbil, pig, cat, dog, rabbit, goat, sheep, cow, horse, camel, cynomolgus, marmoset, rhesus or chimpanzee GITR. According to certain exemplary embodiments of the present disclosure, anti-GITR antibodies are provided which specifically bind human GITR and cynomolgus monkey (e.g., *Macaca fascicularis*) GITR. Other anti-GITR antibodies provided herein bind human GITR but do not bind, or bind only weakly, to cynomolgus monkey GITR.

Multispecific Antibodies

The antibodies of the present disclosure may be monospecific or multispecific (e.g., bispecific). Multispecific antibodies may be specific for different epitopes of one target polypeptide or may contain antigen-binding domains specific for more than one target polypeptide. See, e.g., Tutt et al., 1991, J. Immunol. 147:60-69; Kufer et al., 2004, Trends Biotechnol. 22:238-244. The anti-GITR antibodies of the present disclosure can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce a bispecific or a multispecific antibody with a second binding specificity.

The present disclosure includes bispecific antibodies wherein one arm of an immunoglobulin binds human GITR, and the other arm of the immunoglobulin is specific for a second antigen. The GITR-binding arm can comprise any of the HCVR/LCVR or CDR amino acid sequences as set forth in Table 7 herein. In certain embodiments, the GITR-binding arm binds human GITR and blocks GITRL binding to GITR. In other embodiments, the GITR-binding arm binds human GITR but does not block GITRL binding to GITR. In some embodiments, the GITR binding arm binds human GITR and activates GITR signaling. In other embodiments, the GITR binding arm blocks GITRL mediated receptor stimulation. The present disclosure also includes bispecific antibodies wherein one arm of an antibody binds a first epitope of human GITR, and the other arm of said antibody binds a second distinct epitope of human GITR.

An exemplary bispecific antibody format that can be used in the context of the present disclosure involves the use of a first immunoglobulin (Ig) $C_H3$ domain and a second Ig $C_H3$ domain, wherein the first and second Ig $C_H3$ domains differ from one another by at least one amino acid, and wherein at least one amino acid difference reduces binding of the bispecific antibody to Protein A as compared to a bispecific antibody lacking the amino acid difference. In one embodiment, the first Ig $C_H3$ domain binds Protein A and the second Ig $C_H3$ domain contains a mutation that reduces or abolishes Protein A binding such as an H95R modification (by IMGT exon numbering; H435R by EU numbering). The second $C_H3$ may further comprise a Y96F modification (by IMGT; Y436F by EU). Further modifications that may be found within the second $C_H3$ include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies. Variations on the bispecific antibody format described above are contemplated within the scope of the present disclosure.

Other exemplary bispecific formats that can be used in the context of the present disclosure include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED) body, leucine zipper, DUOBODY®, IgG1/IgG2, dual acting Fab (DAF)-IgG, and Mab² bispecific formats (see, e.g., Klein et al. 2012, mAbs 4:6, 1-11, and references cited therein, for a review of the foregoing formats). Bispecific antibodies can also be constructed using peptide/nucleic acid conjugation, e.g., wherein unnatural amino acids with orthogonal chemical reactivity are used to generate site-specific antibody-oligonucleotide conjugates which then self-assemble into multimeric complexes with defined composition, valency and geometry. (See, e.g., Kazane et al., *J. Am. Chem. Soc.* [Epub: Dec. 4, 2012]).

Therapeutic Formulation and Administration

The disclosure provides pharmaceutical compositions comprising the anti-GITR antibodies or antigen-binding fragments thereof of the present disclosure. The pharmaceutical compositions provided herein are formulated with suitable carriers, excipients, and other agents that provide improved transfer, delivery, tolerance, and the like. A multitude of appropriate formulations can be found in the formulary known to all pharmaceutical chemists: Remington's Pharmaceutical Sciences, Mack Publishing Company, Easton, PA. These formulations include, for example, powders, pastes, ointments, jellies, waxes, oils, lipids, lipid (cationic or anionic) containing vesicles (such as LIPOFECTIN™, Life Technologies, Carlsbad, CA), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antibody administered to a patient may vary depending upon the age and the size of the patient, target disease, conditions, route of administration, and the like. The preferred dose is typically calculated according to body weight or body surface area. In an adult patient, it may be advantageous to intravenously administer the antibody of the present disclosure normally at a single dose of about 0.01 to about 20 mg/kg body weight, more preferably about 0.02 to about 7, about 0.03 to about 5, or about 0.05 to about 3 mg/kg body weight. Depending on the severity of the condition, the frequency and the duration of the treatment can be adjusted. Effective dosages and schedules for administering anti-GITR antibodies may be determined empirically; for example, patient progress can be monitored by periodic assessment, and the dose adjusted accordingly. Moreover, interspecies scaling of dosages can be performed using well-known methods in the art (e.g., Mordenti et al., 1991, *Pharmaceut. Res.* 8:1351).

Various delivery systems are known and can be used to administer the pharmaceutical composition provided herein, e.g., encapsulation in liposomes, microparticles, microcapsules, recombinant cells capable of expressing the mutant viruses, receptor mediated endocytosis (see, e.g., Wu et al., 1987, J. Biol. Chem. 262:4429-4432). Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

A pharmaceutical composition of the present disclosure can be delivered subcutaneously or intravenously with a standard needle and syringe. In addition, with respect to subcutaneous delivery, a pen delivery device readily has applications in delivering a pharmaceutical composition of the present disclosure. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present disclosure. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, IN), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, NJ), OPTIPEN™, OPTIPEN PRO™, OPTIPEN STARLET™, and OPTICLIK™ (sanofi-aventis, Frankfurt, Germany), to name only a few. Examples of disposable pen delivery devices having applications in subcutaneous delivery of a pharmaceutical composition of the present disclosure include, but are not limited to the SOLOSTAR™ pen (sanofi-aventis), the FLEXPEN™ (Novo Nordisk), and the KWIKPEN™ (Eli Lilly), the SURECLICK™ Autoinjector (Amgen, Thousand Oaks, CA), the PENLET™ (Haselmeier, Stuttgart, Germany), the EPIPEN® (Dey, L.P.), and the HUMIRA™ Pen (Abbott Labs, Abbott Park IL), to name only a few.

In certain situations, the pharmaceutical composition can be delivered in a controlled release system. In one embodiment, a pump may be used (see Langer, supra; Sefton, 1987, CRC Crit. Ref. Biomed. Eng. 14:201). In another embodiment, polymeric materials can be used; see, Medical Applications of Controlled Release, Langer and Wise (eds.), 1974, CRC Pres., Boca Raton, Florida. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to about 500 mg per dosage form in a unit dose; especially in the form of injection, it is preferred that the aforesaid antibody is contained in about 5 to about 100 mg and in about 10 to about 250 mg for the other dosage forms.

Therapeutic Uses of the Antibodies

The present disclosure includes methods comprising administering to a subject in need thereof a therapeutic composition comprising an anti-GITR antibody (e.g., an anti-GITR antibody comprising any of the HCVR/LCVR or CDR sequences as set forth in Table 7 herein). The therapeutic composition can comprise any of the anti-GITR antibodies, antigen-binding fragments thereof, or ADCs disclosed herein, and a pharmaceutically acceptable carrier or diluent.

The antibodies provided herein are useful, inter alia, for the treatment, prevention and/or amelioration of any disease or disorder associated with or mediated by GITR expression or activity, or treatable by blocking the interaction between GITR and GITRL, and/or stimulating GITR activity and/or signaling. For example, the antibodies and antigen-binding fragments of the present disclosure can be used to treat immune and proliferative diseases or disorders, e.g., cancer, by modulating the immune response, i.e. the anti-tumor response, though, e.g., GITR activation.

In some embodiments, the antibodies described herein deplete cells expressing high levels of GITR independent of their ligand blocking ability, e.g., via ADCC. The antibodies and antigen-binding fragments of the instant disclosure can be used to treat a disease or disorder by enhancing an immune response. The instant disclosure includes methods of modulating anti-tumor immune response in a subject comprising administering to the subject an anti-GITR antibody or antigen-binding fragment described herein. In some embodiments, the antibody or antigen-binding fragment of the instant disclosure enhances intra-tumoral T effector/T regulatory cell ratio conducive for therapeutic benefit. In some embodiments, the antibody or antigen-binding fragment thereof of the instant disclosure enhances intratumoral T regulatory cell depletion conducive for therapeutic benefit. In some embodiments, the antibody or antigen-binding fragment thereof of the instant disclosure increases CD8+ T-cell/T regulatory cell ratio conducive for therapeutic benefit. In some embodiments, the antibody or antigen-binding fragment of the instant disclosure promotes T-cell survival.

Exemplary diseases or disorders that can be treated by the antibodies and antigen-binding fragments include immune and proliferative diseases or disorders, e.g., cancer. The antibodies and antigen-binding fragments of the present disclosure can be used to treat primary and/or metastatic tumors arising in the brain and meninges, oropharynx, lung and bronchial tree, gastrointestinal tract, male and female reproductive tract, muscle, bone, skin and appendages, connective tissue, spleen, immune system, blood forming cells and bone marrow, liver and urinary tract, and special sensory organs such as the eye. In some embodiments, the antibodies and antigen-binding fragments of the instant disclosure are used to treat solid or blood-borne tumors. In certain embodiments, the antibodies provided herein are used to treat one or more of squamous cell skin cancer, cutaneous squamous cell carcinoma (CSCC), myeloma, lung cancer, melanoma, head and neck squamous cell carcinoma (SCCHN), small cell lung cancer, non-small cell lung cancer (NSCLC), cervical cancer, e.g. cervical squamous cell carcinoma (cervical SCC), breast cancer, and renal cell carcinoma (RCC), adenocarcinoma, colorectal cancer (CRC), pancreatic carcinoma, head and neck cancer, prostate cancer, malignant gliomas, osteosarcoma, colorectal cancer, gastric cancer (e.g., gastric cancer with MET amplification), malignant mesothelioma, multiple myeloma, ovarian cancer, synovial sarcoma, thyroid cancer, breast cancer, including triple negative breast cancer, testicular cancer, esophageal cancer, uterine cancer, endometrial cancer, or liver cancer. In some aspects, the antibodies of the instant disclosure are used to treat an immune checkpoint blockade (ICB) naïve cancer. In some aspects, the antibodies of the instant disclosure are used to treat an ICB experienced cancer.

In some aspects, the antibodies of the instant disclosure are used to treat colorectal cancer. In some aspects, the antibodies of the instant disclosure are used to treat head and neck squamous cell carcinoma (HNSCC or SCCHN). In some aspects, antibodies of the instant disclosure are used to treat cutaneous squamous cell carcinoma (CSCC). In some aspects, the antibodies of the instant disclosure are used to treat gastric cancer. In some aspects, antibodies of the instant disclosure are used to treat non-small cell lung cancer (NSCLC). In some aspects, antibodies of the instant disclosure are used to treat cervical cancer. In some aspects, antibodies of the instant disclosure are used to treat esophageal cancer. In some aspects, antibodies of the instant disclosure are used to treat melanoma. In some aspects, antibodies of the instant disclosure are used to treat triple negative breast cancer. In some aspects, antibodies of the instant disclosure are used to treat renal cell carcinoma. In some aspects, antibodies of the instant disclosure are used to treat breast cancer.

In certain embodiments, the antibodies provided herein are useful for treating an autoimmune disease, including but not limited to, alopecia areata, autoimmune hepatitis, celiac disease, Graves' disease, Guillain-Barre syndrome, Hashimoto's disease, hemolytic anemia, inflammatory bowel disease, inflammatory myopathies, multiple sclerosis, primary biliary cirrhosis, psoriasis, rheumatoid arthritis, scleroderma, Sjögren's syndrome, systemic lupus erthyematosus, vitiligo, autoimmune pancreatitis, autoimmune urticaria, autoimmune thrombocytopenic purpura, Crohn's disease, diabetes type I, eosinophilic fasciitis, eosinophilic enterogastritis, Goodpasture's syndrome, myasthenia gravis, psoriatic arthritis, rheumatic fever, ulcerative colitis, vasculitis and Wegener's granulomatosis.

In the context of the methods of treatment described herein, the anti-GITR antibody may be administered as a monotherapy (i.e., as the only therapeutic agent) or in combination with one or more additional therapeutic agents (examples of which are described elsewhere herein).

Combination Therapies and Formulations

Provided herein are also combination therapies utilizing an anti-GITR antibody of the present disclosure and any additional therapeutic agent that may be advantageously combined with an antibody of the instant disclosure or antigen-binding fragment thereof.

The present disclosure includes compositions and therapeutic formulations comprising any of the anti-GITR antibodies described herein in combination with one or more additional therapeutically active components, and methods of treatment comprising administering such combinations to subjects in need thereof.

The antibodies of the present disclosure may be combined synergistically with one or more anti-cancer drugs or therapy used to treat cancer, including, for example, In certain embodiments, the antibodies provided herein are used to treat one or more of squamous cell skin cancer, cutaneous squamous cell carcinoma (CSCC), myeloma, lung cancer, melanoma, head and neck squamous cell carcinoma (SCCHN), small cell lung cancer, non-small cell lung cancer (NSCLC), cervical cancer, e.g. cervical squamous cell carcinoma (cervical SCC), breast cancer, and renal cell carcinoma (RCC), adenocarcinoma, colorectal cancer (CRC), pancreatic carcinoma, head and neck cancer, prostate cancer, glioblastoma multiforme, malignant gliomas, osteosarcoma, colorectal cancer, gastric cancer (e.g., gastric cancer with MET amplification), malignant mesothelioma, multiple myeloma, ovarian cancer, synovial sarcoma, thyroid cancer, breast cancer, including triple negative breast cancer, testicular cancer, esophageal cancer, uterine cancer, endometrial cancer, or liver cancer. In some aspects, the antibodies of the instant disclosure are used to treat an immune checkpoint blockade (ICB) naïve cancer. In some aspects, the antibodies of the instant disclosure are used to treat an ICB experienced cancer.

In some aspects, the antibodies of the instant disclosure are used to treat colorectal cancer. In some aspects, the antibodies of the instant disclosure are used to treat head and neck squamous cell carcinoma (HNSCC or SCCHN). In some aspects, antibodies of the instant disclosure are used to treat cutaneous squamous cell carcinoma (CSCC). In some aspects, the antibodies of the instant disclosure are used to treat gastric cancer. In some aspects, antibodies of the instant disclosure are used to treat non-small cell lung cancer (NSCLC). In some aspects, antibodies of the instant disclosure are used to treat cervical cancer. In some aspects, antibodies of the instant disclosure are used to treat esophageal cancer. In some aspects, antibodies of the instant disclosure are used to treat melanoma. In some aspects, antibodies of the instant disclosure are used to treat triple negative breast cancer. In some aspects, antibodies of the instant disclosure are used to treat renal cell carcinoma. In some aspects, antibodies of the instant disclosure are used to treat breast cancer.

It is contemplated herein to use anti-GITR antibodies provided herein in combination with immunostimulatory and/or immunosupportive therapies to inhibit tumor growth, and/or enhance survival of cancer patients. The immunostimulatory therapies include direct immunostimulatory therapies to augment immune cell activity by either "releasing the brake" on suppressed immune cells or "stepping on the gas" to activate an immune response. Examples include targeting other checkpoint receptors, vaccination and adjuvants. The immunosupportive modalities may increase antigenicity of the tumor by promoting immunogenic cell death, inflammation or have other indirect effects that promote an anti-tumor immune response. Examples include radiation, chemotherapy, anti-angiogenic agents, and surgery.

The instant disclosure includes methods of modulating anti-tumor immune response in a subject comprising administering to the subject an anti-GITR antibody in combination with one or more agonistic antibodies against activating receptors and one or more blocking antibodies against inhibitory receptors that enhance T-cell stimulation to promote tumor destruction.

The instant disclosure includes methods of modulating anti-tumor immune response in a subject comprising administering to the subject an anti-GITR antibody or antigen-binding fragment described herein in combination with one or more isolated antibody or antigen-binding fragment thereof that binds to a second T-cell activating receptor (i.e., other than GITR). In some embodiments, the second T-cell activating receptor is CD28, OX40, CD137, CD27, or VEM. The instant disclosure also includes formulations comprising an anti-GITR antibody or antigen binding fragment thereof provided herein and an antibody or antigen-binding fragment that binds said second T-cell activating receptor.

In various embodiments, one or more antibodies of the present disclosure may be used in combination with an antibody to PD-L1, an antibody to PD-1 (e.g., nivolumab, cemiplimab), a LAG-3 inhibitor, a CTLA-4 inhibitor (e.g., ipilimumab), a TIM3 inhibitor, a BTLA inhibitor, a TIGIT inhibitor, a CD47 inhibitor, an antagonist of another T-cell co-inhibitor or ligand (e.g., an antibody to CD-28, 2B4, LY108, LAIR1, ICOS, CD160 or VISTA), an indoleamine-2,3-dioxygenase (IDO) inhibitor, a vascular endothelial growth factor (VEGF) antagonist [e.g., a "VEGF-Trap" such as aflibercept or other VEGF-inhibiting fusion protein as set forth in U.S. Pat. No. 7,087,411, or an anti-VEGF antibody or antigen binding fragment thereof (e.g., bevacizumab, or ranibizumab) or a small molecule kinase inhibitor of VEGF receptor (e.g., sunitinib, sorafenib, or pazopanib)], an Ang2 inhibitor (e.g., nesvacumab), a transforming growth factor beta (TGFβ) inhibitor, an epidermal growth factor receptor (EGFR) inhibitor (e.g., erlotinib, cetuximab), an agonist to a co-stimulatory receptor (e.g., an agonist to glucocorticoid-induced TNFR-related protein), an antibody to a tumor-specific antigen (e.g., CA9, CA125, melanoma-associated antigen 3 (MAGE3), carcinoembryonic antigen (CEA), vimentin, tumor-M2-PK, prostate-specific antigen (PSA), mucin-1, MART-1, and CA19-9), a vaccine (e.g., Bacillus Calmette-Guerin, a cancer vaccine), an adjuvant to increase antigen presentation (e.g., granulocyte-macrophage colony-stimulating factor), a bispecific antibody (e.g., CD3×CD20 bispecific antibody, PSMA×CD3 bispecific antibody), a cytotoxin, a chemotherapeutic agent (e.g., dacarbazine, temozolomide, cyclophosphamide, docetaxel, doxorubicin, daunorubicin, cisplatin, carboplatin, gemcitabine, methotrexate, mitoxantrone, oxaliplatin, paclitaxel, and vincristine), cyclophosphamide, radiotherapy, an IL-6R inhibitor (e.g., sarilumab), an IL-4R inhibitor (e.g., dupilumab), an IL-10 inhibitor, a cytokine such as IL-2, IL-7, IL-21, and IL-15, an antibody-drug conjugate (ADC) (e.g., anti-CD19-DM4 ADC, and anti-DS6-DM4 ADC), an anti-inflammatory drug (e.g., corticosteroids, and non-steroidal anti-inflammatory drugs), a dietary supplement such as anti-oxidants or any palliative care to treat cancer. In certain embodiments, the anti-GITR antibodies of the present disclosure may be used in combination with cancer vaccines including dendritic cell vaccines, oncolytic viruses, tumor cell vaccines, etc. to augment the anti-tumor response. Examples of cancer vaccines that can be used in combination with anti-GITR antibodies of the present disclosure include MAGE3 vaccine for melanoma and bladder cancer, MUC1 vaccine for breast cancer, EGFRv3 (e.g., Rindopepimut) for brain cancer (including glioblastoma multiforme), or ALVAC-CEA (for CEA+ cancers).

In some embodiments, one or more anti-GITR antibodies described herein are administered in combination with one or more anti-PD1 antibodies, including but not limited to those described in U.S. Patent Publication No. 2015/0203579 and U.S. Pat. No. 9,987,500, each of which is incorporated herein by reference in its entirety. In some embodiments, the anti-GITR antibody is an antibody from U.S. 2017/0355774A1, modified as described herein. In some embodiments, the anti-PD1 antibody is cemiplimab, pembrolizumab, or nivolumab.

In certain embodiments, the anti-GITR antibodies provided herein may be administered in combination with radiation therapy in methods to generate long-term durable anti-tumor responses and/or enhance survival of patients with cancer. In some embodiments, the anti-GITR antibodies provided herein may be administered prior to, concomitantly or after administering radiation therapy to a cancer patient. For example, radiation therapy may be administered in one or more doses to tumor lesions followed by administration of one or more doses of anti-GITR antibodies provided herein. In some embodiments, radiation therapy may be administered locally to a tumor lesion to enhance the local immunogenicity of a patient's tumor (adjuvinating radiation) and/or to kill tumor cells (ablative radiation) followed by systemic administration of an anti-GITR antibody provided herein. For example, intracranial radiation may be administered to a patient with brain cancer (e.g., glioblastoma multiforme) in combination with systemic administration of an anti-GITR antibody provided herein. In certain embodiments, the anti-GITR antibodies provided herein may be administered in combination with radiation therapy and a chemotherapeutic agent (e.g., temozolomide) or a VEGF antagonist (e.g., aflibercept).

In certain embodiments, the anti-GITR antibodies provided herein may be administered in combination with one or more anti-viral drugs to treat chronic viral infection caused by LCMV, HIV, HPV, HBV or HCV. Examples of anti-viral drugs include, but are not limited to, zidovudine, lamivudine, abacavir, ribavirin, lopinavir, efavirenz, cobicistat, tenofovir, rilpivirine and corticosteroids. In some embodiments, the anti-GITR antibodies provided herein may be administered in combination with a LAG3 inhibitor, a CTLA-4 inhibitor or any antagonist of another T-cell co-inhibitor to treat chronic viral infection.

In certain embodiments, the anti-GITR antibodies provided herein may be combined with an antibody to a Fc receptor on immune cells for the treatment of an autoimmune disease. In one embodiment, an antibody or fragment thereof provided herein is administered in combination with an antibody or antigen-binding protein targeted to an antigen specific to autoimmune tissue. In certain embodiments, an antibody or antigen-binding fragment thereof provided herein is administered in combination with an antibody or antigen-binding protein targeted to a T-cell receptor or a B-cell receptor, including but not limited to, Fcα (e.g., CD89), Fc gamma (e.g., CD64, CD32, CD16a, and CD16b), CD19, etc. The antibodies of fragments thereof provided herein may be used in combination with any drug or therapy known in the art (e.g., corticosteroids and other immunosuppressants) to treat an autoimmune disease or disorder including, but not limited to alopecia areata, autoimmune hepatitis, celiac disease, Graves' disease, Guillain-Barre syndrome, Hashimoto's disease, hemolytic anemia, inflammatory bowel disease, inflammatory myopathies, multiple sclerosis, primary biliary cirrhosis, psoriasis, rheumatoid arthritis, scleroderma, Sjögren's syndrome, systemic lupus erthyematosus, vitiligo, autoimmune pancreatitis, autoimmune urticaria, autoimmune thrombocytopenic purpura, Crohn's disease, diabetes type I, eosinophilic fasciitis, eosinophilic enterogastritis, Goodpasture's syndrome, myasthenia gravis, psoriatic arthritis, rheumatic fever, ulcerative colitis, vasculitis and Wegener's granulomatosis.

The instant disclosure also includes methods of modulating anti-tumor immune response in a subject comprising administering to the subject an anti-GITR antibody or antigen-binding fragment described herein in combination with one or more isolated antibody or antigen-binding fragment thereof that binds to a T-cell inhibitory receptor. In some embodiments, the T-cell inhibitory receptor is CTLA-4, PD-1, TIM-3, BTLA, VISTA, or LAG-3. The instant disclosure also includes formulations comprising an anti-GITR antibody or antigen-binding fragment thereof provided herein and an antibody or antigen-binding fragment that binds said T-cell inhibitory receptor. In some aspects, for example, in the presence of PD1 signaling, cemiplimab restored the ability of the anti-GITR antibodies to enhance anti-CD3-stimulated T-cell activation.

The instant disclosure also includes methods of treating cancer by administering an antibody or antigen-binding fragment thereof or formulation described herein to a subject in conjunction with radiation or chemotherapy.

In some embodiments, the anti-GITR antibodies of the present disclosure are co-formulated with and/or administered in combination with one or more additional therapeutically active component(s) selected from the group consisting of: an EGFR antagonist (e.g., an anti-EGFR antibody [e.g., cetuximab or panitumumab] or small molecule inhibitor of EGFR [e.g., gefitinib or erlotinib]), an antagonist of another EGFR family member such as Her2/ErbB2, ErbB3 or ErbB4 (e.g., anti-ErbB2 [e.g., trastuzumab or T-DM1 {KADCYLA®}], anti-ErbB3 or anti-ErbB4 antibody or small molecule inhibitor of ErbB2, ErbB3 or ErbB4 activity), an antagonist of EGFRvIII (e.g., an antibody that specifically binds EGFRvIII), a cMET anagonist (e.g., an anti-cMET antibody), an IGF1R antagonist (e.g., an anti-IGF1R antibody), a B-raf inhibitor (e.g., vemurafenib, sorafenib, GDC-0879, PLX-4720), a PDGFR-α inhibitor (e.g., an anti-PDGFR-α antibody), a PDGFR-β inhibitor (e.g., an anti-PDGFR-0 antibody or small molecule kinase inhibitor such as, e.g., imatinib mesylate or sunitinib malate), a PDGF ligand inhibitor (e.g., anti-PDGF-A, -B, -C, or -D antibody, aptamer, siRNA, etc.), a VEGF antagonist (e.g., a VEGF-Trap such as aflibercept, see, e.g., U.S. Pat. No. 7,087,411 (also referred to herein as a "VEGF-inhibiting fusion protein"), anti-VEGF antibody (e.g., bevacizumab), a small molecule kinase inhibitor of VEGF receptor (e.g., sunitinib, sorafenib or pazopanib)), a DLL4 antagonist (e.g., an anti-DLL4 antibody disclosed in US 2009/0142354 such as REGN421), an Ang2 antagonist (e.g., an anti-Ang2 antibody disclosed in US 2011/0027286 such as H1H685P), a FOLH1 antagonist (e.g., an anti-FOLH1 antibody), a STEAP1 or STEAP2 antagonist (e.g., an anti-STEAP1 antibody or an anti-STEAP2 antibody), a TMPRSS2 antagonist (e.g., an anti-TMPRSS2 antibody), a MSLN antagonist (e.g., an anti-MSLN antibody), a CA9 antagonist (e.g., an anti-CA9 antibody), a uroplakin antagonist (e.g., an anti-uroplakin [e.g., anti-UPK3A] antibody), a MUC16 antagonist (e.g., an anti-MUC16 antibody), a Tn antigen antagonist (e.g., an anti-Tn antibody), a CLEC12A antagonist (e.g., an anti-CLEC12A antibody), a TNFRSF17 antagonist (e.g., an anti-TNFRSF17 antibody), a LGR5 antagonist (e.g., an anti-LGR5 antibody), a monovalent CD20 antagonist (e.g., a monovalent anti-CD20 antibody such as rituximab), etc. Other agents that may be beneficially administered in combination with antibodies provided herein include, e.g., tamoxifen, aromatase inhibitors, and cytokine inhibitors, including small-molecule cytokine inhibitors and antibodies that bind to cytokines such as IL-1, IL-2, IL-3, IL-4, IL-5, IL-6, IL-8, IL-9, IL-11, IL-12, IL-13, IL-17, IL-18, or to their respective receptors.

The present disclosure includes compositions and therapeutic formulations comprising any of the anti-GITR antibodies described herein in combination with one or more chemotherapeutic agents. Examples of chemotherapeutic agents include alkylating agents such as thiotepa and cyclophosphamide (Cytoxan™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK™; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (Taxol™, Bristol-Myers Squibb Oncology, Princeton, N.J.) and docetaxel (Taxotere™; Aventis Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; and pharmaceutically acceptable salts, acids or derivatives of any of the above.

The anti-GITR antibodies provided herein may also be administered and/or co-formulated in combination with antivirals, antibiotics, analgesics, corticosteroids, steroids, oxygen, antioxidants, COX inhibitors, cardioprotectants, metal chelators, IFN-gamma, and/or NSAIDs.

The additional therapeutically active component(s), e.g., any of the agents listed above or derivatives thereof, may be administered just prior to, concurrent with, or shortly after the administration of an anti-GITR antibody of the present disclosure; (for purposes of the present disclosure, such administration regimens are considered the administration of an anti-GITR antibody "in combination with" an additional therapeutically active component). The present disclosure includes pharmaceutical compositions in which an anti-GITR antibody of the present disclosure is co-formulated with one or more of the additional therapeutically active component(s) as described elsewhere herein.

The additional therapeutically active component(s) may be administered to a subject prior to administration of an anti-GITR antibody of the present disclosure. For example, a first component may be deemed to be administered "prior to" a second component if the first component is administered 1 week before, 72 hours before, 60 hours before, 48 hours before, 36 hours before, 24 hours before, 12 hours before, 6 hours before, 5 hours before, 4 hours before, 3 hours before, 2 hours before, 1 hour before, 30 minutes before, 15 minutes before, 10 minutes before, 5 minutes before, or less than 1 minute before administration of the second component. In other embodiments, the additional therapeutically active component(s) may be administered to a subject after administration of an anti-GITR antibody of the present disclosure. For example, a first component may be deemed to be administered "after" a second component if the first component is administered 1 minute after, 5 minutes after, 10 minutes after, 15 minutes after, 30 minutes after, 1 hour after, 2 hours after, 3 hours after, 4 hours after, 5 hours after, 6 hours after, 12 hours after, 24 hours after, 36 hours after, 48 hours after, 60 hours after, 72 hours after administration of the second component. In yet other embodiments, the additional therapeutically active component(s) may be administered to a subject concurrent with administration of an anti-GITR antibody of the present disclosure. "Concurrent" administration, for purposes of the present disclosure, includes, e.g., administration of an anti-GITR antibody and an additional therapeutically active component to a subject in a single dosage form (e.g., co-formulated), or in separate dosage forms administered to the subject within about 30 minutes or less of each other. If administered in separate dosage forms, each dosage form may be administered via the same route (e.g., both the anti-GITR antibody and the additional therapeutically active component may be administered intravenously, subcutaneously, etc.); alternatively, each dosage form may be administered via a different route (e.g., the anti-GITR antibody may be administered intravenously, and the additional therapeutically active component may be administered subcutaneously). In any event, administering the components in a single dosage from, in separate dosage forms by the same route, or in separate dosage forms by different routes are all considered "concurrent administration," for purposes of the present disclosure. For purposes of the present disclosure, administration of an anti-GITR antibody "prior to", "concurrent with," or "after" (as those terms are defined herein above) administration of an additional therapeutically active component is considered administration of an anti-GITR antibody "in combination with" an additional therapeutically active component).

The present disclosure includes pharmaceutical compositions in which an anti-GITR antibody of the present disclosure is co-formulated with one or more of the additional therapeutically active component(s) as described elsewhere herein using a variety of dosage combinations.

In exemplary embodiments in which an anti-GITR antibody provided herein is administered in combination with a VEGF antagonist (e.g., a VEGF trap such as aflibercept), including administration of co-formulations comprising an anti-GITR antibody and a VEGF antagonist, the individual components may be administered to a subject and/or co-formulated using a variety of dosage combinations. For example, the anti-GITR antibody may be administered to a subject and/or contained in a co-formulation in an amount selected from the group consisting of 0.01 mg, 0.02 mg, 0.03 mg, 0.04 mg, 0.05 mg, 0.1 mg, 0.2 mg, 0.3 mg, 0.4 mg, 0.5 mg, 0.6 mg, 0.7 mg, 0.8 mg, 0.9 mg, 1.0 mg, 1.5 mg, 2.0 mg, 2.5 mg, 3.0 mg, 3.5 mg, 4.0 mg, 4.5 mg, 5.0 mg, 6.0 mg, 7.0 mg, 8.0 mg, 9.0 mg, and 10.0 mg; and the VEGF antagonist (e.g., a VEGF trap such as aflibercept) may be administered to the subject and/or contained in a co-formulation in an amount selected from the group consisting of 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, 2.5 mg, 2.6 mg, 2.7 mg, 2.8 mg, 2.9 mg and 3.0 mg. The combinations/co-formulations may be administered to a subject according to any of the administration regimens disclosed elsewhere herein, including, e.g., twice a week, once every week, once every 2 weeks, once every 3 weeks, once every month, once every 2 months, once every 3 months, once every 4 months, once every 5 months, once every 6 months, etc.

Administration Regimens

According to certain embodiments of the present disclosure, multiple doses of an anti-GITR antibody (or a pharmaceutical composition comprising a combination of an anti-GITR antibody and any of the additional therapeutically active agents mentioned herein) may be administered to a subject over a defined time course. The methods according to this aspect provided herein comprise sequentially administering to a subject multiple doses of an anti-GITR antibody provided herein. As used herein, "sequentially administering" means that each dose of anti-GITR antibody is administered to the subject at a different point in time, e.g., on different days separated by a predetermined interval (e.g., hours, days, weeks or months). The present disclosure includes methods which comprise sequentially administering to the patient a single initial dose of an anti-GITR antibody, followed by one or more secondary doses of the anti-GITR antibody, and optionally followed by one or more tertiary doses of the anti-GITR antibody.

The terms "initial dose," "secondary doses," and "tertiary doses," refer to the temporal sequence of administration of the anti-GITR antibody provided herein. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of anti-GITR antibody, but generally may differ from one another in terms of frequency of administration. In certain embodiments, however, the amount of anti-GITR antibody contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In certain exemplary embodiments of the present disclosure, each secondary and/or tertiary dose is administered 1 to 26 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, 16½, 17, 17½, 18, 18½, 19, 19½, 20, 20½, 21, 21½, 22, 22½, 23, 23½, 24, 24½, 25, 25½, 26, 26½, or more) weeks after the immediately preceding dose. The phrase "the immediately preceding dose," as used herein, means, in a sequence of multiple administrations, the dose of anti-GITR antibody which is administered to a patient prior to the administration of the very next dose in the sequence with no intervening doses.

The methods according to this aspect provided herein may comprise administering to a patient any number of secondary and/or tertiary doses of an anti-GITR antibody. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient. The administration regimen may be carried out indefinitely over the lifetime of a particular subject, or until such treatment is no longer therapeutically needed or advantageous.

In embodiments involving multiple secondary doses, each secondary dose may be administered at the same frequency as the other secondary doses. For example, each secondary dose may be administered to the patient 1 to 2 weeks or 1 to 2 months after the immediately preceding dose. Similarly, in embodiments involving multiple tertiary doses, each tertiary dose may be administered at the same frequency as the other tertiary doses. For example, each tertiary dose may be administered to the patient 2 to 12 weeks after the immediately preceding dose. In certain embodiments provided herein, the frequency at which the secondary and/or tertiary doses are administered to a patient can vary over the course of the treatment regimen. The frequency of administration may also be adjusted during the course of treatment by a physician depending on the needs of the individual patient following clinical examination.

The present disclosure includes administration regimens in which 2 to 6 loading doses are administered to a patient at a first frequency (e.g., once a week, once every two weeks, once every three weeks, once a month, once every two months, etc.), followed by administration of two or more maintenance doses to the patient on a less frequent basis. For example, according to this aspect provided herein, if the loading doses are administered at a frequency of once a month, then the maintenance doses may be administered to the patient once every six weeks, once every two months, once every three months, etc.

Diagnostic Uses of the Antibodies

The anti-GITR antibodies of the present disclosure may also be used to detect and/or measure GITR, or GITR-expressing cells in a sample, e.g., for diagnostic purposes. For example, an anti-GITR antibody, or fragment thereof, may be used to diagnose a condition or disease characterized by aberrant expression (e.g., over-expression, under-expression, lack of expression, etc.) of GITR. Exemplary diagnostic assays for GITR may comprise, e.g., contacting a sample, obtained from a patient, with an anti-GITR antibody provided herein, wherein the anti-GITR antibody is labeled with a detectable label or reporter molecule. Alternatively, an unlabeled anti-GITR antibody can be used in diagnostic applications in combination with a secondary antibody which is itself detectably labeled. The detectable label or reporter molecule can be a radioisotope, such as $^3H$, $^4C$, $^{32}P$, 3S, or $^{125}I$; a fluorescent or chemiluminescent moiety such as fluorescein, or rhodamine; or an enzyme such as alkaline phosphatase, beta-galactosidase, horseradish peroxidase, or luciferase. Specific exemplary assays that can be used to detect or measure GITR in a sample include enzyme-linked immunosorbent assay (ELISA®), radioimmunoassay (RIA), immuno-PET (e.g., $^{89}Zr$, $^{64}Cu$, etc.), and fluorescence-activated cell sorting (FACS).

Samples that can be used in GITR diagnostic assays according to the present disclosure include any tissue or fluid sample obtainable from a patient which contains detectable quantities of GITR protein, or fragments thereof, under normal or pathological conditions. Generally, levels of GITR in a particular sample obtained from a healthy patient (e.g., a patient not afflicted with a disease or condition associated with abnormal GITR levels or activity) will be measured to initially establish a baseline, or standard, level of GITR. This baseline level of GITR can then be compared against the levels of GITR measured in samples obtained from individuals suspected of having a GITR related disease or condition.

EXAMPLES

The following examples are put forth so as to provide those of ordinary skill in the art with a complete disclosure and description of how to make and use the methods and compositions provided herein, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1. Generation of Anti-GITR Antibodies

Anti-GITR antibodies were obtained by immunizing a VELOCIMMUNE® mouse (i.e., an engineered mouse comprising DNA encoding human immunoglobulin heavy and kappa light chain variable regions) with an immunogen comprising a soluble dimeric ecto domain of human GITR. The antibody immune response was monitored by a GITR-specific immunoassay. Several fully human anti-GITR antibodies were isolated directly from antigen-positive B cells without fusion to myeloma cells, as described in U.S. 2007/0280945A1.

Table 1 sets forth the amino acid sequence identifiers of the heavy and light chain variable regions and CDRs of a selected anti-GITR antibody, the CompAb1 antibody, as previously disclosed in U.S. 2017/0355774A1. The corresponding nucleic acid sequence identifiers are set forth in Table 2. Table 3 provides the full length heavy and light chain sequences for the CompAb1 antibody.

TABLE 1

Amino Acid Sequence Identifiers

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| CompAb1 | 2 | 4 | 6 | 8 | 10 | 12 | 14 | 16 |

TABLE 2

Nucleic Acid Sequence Identifiers

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| CompAb1 | 1 | 3 | 5 | 7 | 9 | 11 | 13 | 15 |

TABLE 3

Full Length Heavy and Light Chain Sequences

| | SEQ ID NOS: | | | |
|---|---|---|---|---|
| | Full length Heavy Chain | | Full length Light Chain | |
| Antibody Designation | Nucleic Acid | Amino Acid | Nucleic Acid | Amino Acid |
| CompAb1 | 17 | 19 | 19 | 20 |

Example 2. Assessment and Quantification of Truncation in an Anti-GITR Antibody, CompAb1

Characterization of the CompAb1 antibody observed that a portion was cleaved during protein expression. The following analysis was performed to identify the point where truncation was occurring, and to determine the amount of antibody undergoing truncation.

Samples of CompAb1 antibody were analyzed by intact mass analysis using reverse phase liquid chromatography with a UV detector and an inline Waters Vion IMS QT of mass spectrometer to determine the molecular weight of the antibody and its variants. Each antibody sample was injected onto a Waters ACQUITY UPLC BEH300 C4 column (1.7 μm, 2.1 mm×50 mm) equilibrated with 99% of mobile phase A (0.1% formic acid in MILLI-Q® water) and 1% of mobile phase B (0.1% formic acid in acetonitrile) prior to sample injection. The column temperature was maintained at 80° C. Proteins were eluted using a Waters ACQUITY UPLC system using a flow rate of 0.25 mL/min. Upon sample injection, the overall mobile phase gradient was held at 1% mobile phase B for the first 3 minutes, followed by a linear increase from 1% to 20% mobile phase B over the course of 2 minutes, a second linear increase from 20% to 35% mobile phase B over the course of 15 minutes, and then a third linear increase from 35% to 70% mobile phase B over 5 minutes with a final increase to 90% mobile phase B over the next 2 minutes. The elution profile of the eluted protein was monitored at 215 nm using a photodiode array detector and the mass of the eluted protein was measured using a Waters Vion IMS QT of Mass Spectrometer.

Using this process, a truncated variant of the full length GITR antibody CompAb1 was identified. The truncated form of the antibody eluted earlier than the full-length antibody in the UV chromatogram. The mass of the truncated form corresponded to a cleavage between residues $N^{101}$ and $P^{102}$ in the CDR3 region of CompAb1 heavy chain. The abundance of the truncated form was estimated to be around 5% of the total antibody based on the UV chromatogram peak area from multiple lots of CompAb1. The location of these cleavages was verified by reduced peptide mapping analysis where CompAb1 was digested to peptides ending in lysine or arginine using trypsin and analyzed by reversed phase LC separation followed by mass spectrometry on a Q EXACTIVE™ mass spectrometer. Tryptic peptides corresponding to the full length antibody as well as shorter peptides ending at $N^{101}$ and $P^{102}$ corresponding to the truncation site in the CDR3 were identified based on their accurate masses and fragmentation spectra.

Levels of Truncation in CompAb1 Increase Over Time in Serum In Vitro and In Vivo:

CompAb1 was incubated in phosphate buffered saline (PBS) and monkey serum at 37° C. for up to 28 days to study the stability of CompAb1 under physiological conditions in vitro. In addition, mice were dosed with CompAb1 at 10 mg/kg and serum was collected at 1 and 8 days to study the stability of CompAb1 in vivo.

CompAb1 was purified from the serum samples using magnetic beads coated with an anti-human Fc antibody. Purified CompAb1 was eluted from the beads under acidic conditions and then digested using the enzyme Lys-C, which cut the full-length antibody into peptides ending in lysine. The samples were separated using a reversed phase LC gradient and analyzed by a Q EXACTIVE™ HF mass spectrometer. Lys-C generated peptides corresponding to the full-length antibody and the antibody truncated at $N^{101}/P^{102}$ were identified in all the samples based on their accurate mass and fragmentation spectra. The extracted ion chromatogram peak areas corresponding to the masses of the intact and truncated antibody were used to calculate the percent truncation in each sample.

Figure 2:
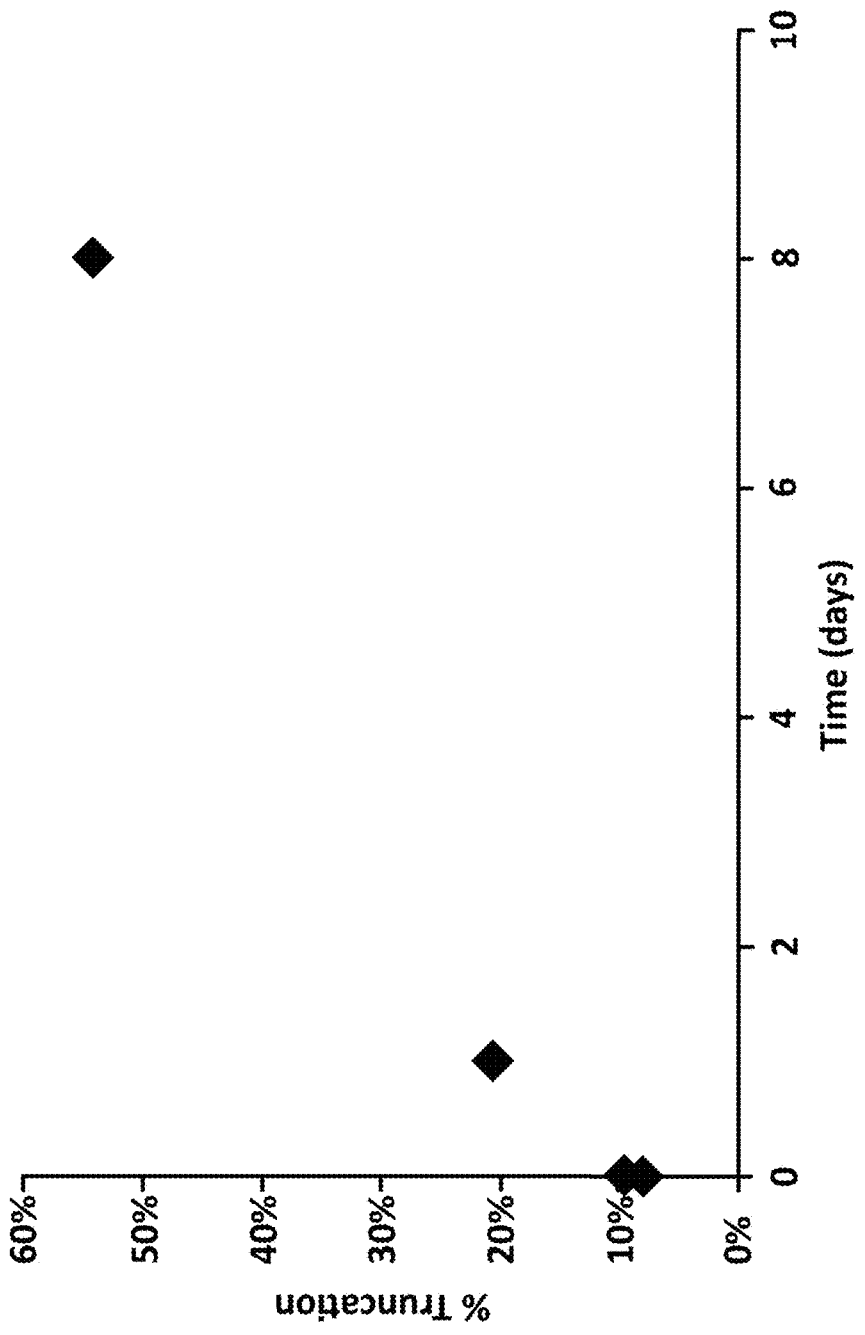
FIG. 2 depicts increase in truncation observed in CompAb1 when dosed at 10 mg/kg in mice. CompAb1 was spiked into mouse serum and PBS prior to pull down (affinity purification) as a 0 day control.

The results showed that incubation in PBS resulted in an increase of CompAb1 truncation from 10.3% to 24.5% over 28 days, and incubation in monkey serum resulted in an increase of the same CompAb1 truncation from 7.4% to 48.7% over 28 days (FIG. 1). The level of truncation in CompAb1 in serum from dosed mice increased from a starting level of 7.7% to 54% after 8 days (FIG. 2).

Example 3. Generation of Heavy Chain Variants of Anti-GITR Antibody CompAb1 that Retain Binding to GITR A screen was performed to identify variants of the CompAb1 heavy chain (HC) that prevent truncation at amino acids $^{101}NP^{102}$ or $^{102}PS^{103}$ in CDR3 while retaining anti-GITR functionality. Double-stranded DNA fragments representing variants of the CompAb1 heavy chain (HC) variable domain were ordered and synthesized by IDT (GBLOCKS® Gene Fragments), and subsequently cloned into an expression vector containing the human IgG1 heavy chain constant region. A total of 36 variants were created by replacing N101 or S103 of the CompAb1 HC with all amino acids except for cysteine. See Table 4.

Antibodies were produced after transient expression of each HC variant and the CompAb1 light chain (1-39 germline universal light chain) in CHO cells.

TABLE 4

CompAb1 Heavy Chain Variants

| Sample Number | HC variant | Light chain (1-39 germline ULC) |
|---|---|---|
| 1 | WT | WT |
| 2 | N101A | WT |
| 3 | N101D | WT |
| 4 | N101E | WT |
| 5 | N101F | WT |
| 6 | N101G | WT |
| 7 | N101H | WT |
| 8 | N101I | WT |
| 9 | N101K | WT |
| 10 | N101L | WT |
| 11 | N101M | WT |
| 12 | N101P | WT |
| 13 | N101Q | WT |
| 14 | N101R | WT |
| 15 | N101S | WT |
| 16 | N101T | WT |
| 17 | N101V | WT |
| 18 | N101W | WT |
| 19 | N101Y | WT |
| 20 | S103A | WT |

TABLE 4-continued

CompAb1 Heavy Chain Variants

| Sample Number | HC variant | Light chain (1-39 germline ULC) |
|---|---|---|
| 21 | S103D | WT |
| 22 | S103E | WT |
| 23 | S103F | WT |
| 24 | S103G | WT |
| 25 | S103H | WT |
| 26 | S103I | WT |
| 27 | S103K | WT |
| 28 | S103L | WT |
| 29 | S103M | WT |
| 30 | S103N | WT |
| 31 | S103P | WT |
| 32 | S103Q | WT |
| 33 | S103R | WT |
| 34 | S103T | WT |
| 35 | S103V | WT |
| 36 | S103W | WT |
| 37 | S103Y | WT |

Antibody-containing supernatants were collected and sent for screening by BIACORE® to measure GITR binding.

Binding affinities and kinetic constants of the human anti-GITR antibodies were determined by surface plasmon resonance.

BIACORE® experiments for antibodies secreted in conditioned culture medium were performed as follows. Using a BIACORE® 2000 instrument at 25° C., antibodies were captured for 80 seconds at a flow rate of 8 uL/min on a CM5 anti-humanFc-coupled surface. Approximately 1000-2000 RU of each antibody were captured. 100 nM hGITR.mmH (soluble monomeric hGITR, SEQ ID NO: 45) or 50 nM hGITR.mFc (dimeric Macaca fasicularis GITR, SEQ ID NO: 46) were injected over this surface for 2 minutes at a flow rate of 50 uL/min. Dissociation was measured for 2 minutes. The $K_D$ and $t_{1/2}$ were calculated by fitting the double-referenced sensorgrams to a 1:1 binding model.

TABLE 5

BIACORE® Binding Affinities: CHOt Supernatants

| | | hGITR.mmH | | hGITR.mFc | |
|---|---|---|---|---|---|
| Sample Number | HC variant | $K_D$ (M) | $t_{1/2}$ (min) | $K_D$ (M) | $t_{1/2}$ (min) |
| 1 | WT | 2.49E−08 | 4.56 | 2.01E−10 | 194.05 |
| 2 | N101A | NB | NB | 4.24E−08 | 0.47 |
| 3 | N101D | 1.48E−08 | 7.52 | 8.13E−11 | 344.98 |
| 4 | N101E | 1.09E−07 | 0.99 | 1.27E−09 | 34.90 |
| 5 | N101F | NB | NB | NB | NB |
| 6 | N101G | IC | IC | IC | IC |
| 7 | N101H | NB | NB | NB | NB |
| 8 | N101I | 3.29E−07 | 1.32 | 2.75E−08 | 0.72 |
| 9 | N101K | 1.70E−08 | 4.91 | 2.69E−08 | 0.99 |
| 10 | N101L | NB | NB | 5.75E−08 | 0.45 |
| 11 | N101M | 1.52E−07 | 1.93 | 2.40E−08 | 0.82 |
| 12 | N101P | NB | NB | NB | NB |
| 13 | N101Q | 3.41E−09 | 16.70 | 9.98E−09 | 3.86 |
| 14 | N101R | IC | IC | 2.94E−08 | 0.86 |
| 15 | N101S | 8.19E−08 | 0.92 | 9.08E−10 | 37.73 |
| 16 | N101T | 6.13E−08 | 1.52 | 2.84E−08 | 109.58 |
| 17 | N101V | 2.91E−08 | 3.46 | 2.39E−08 | 0.98 |
| 18 | N101W | NB | NB | NB | NB |
| 19 | N101Y | NB | NB | NB | NB |
| 20 | S103A | 1.08E−07 | 0.83 | 5.29E−10 | 50.28 |
| 21 | S103D | 7.71E−08 | 1.01 | 5.95E−10 | 65.00 |
| 22 | S103E | 1.19E−07 | 0.76 | 7.42E−10 | 42.43 |
| 23 | S103F | 7.35E−09 | 13.61 | 2.33E−09 | 12.84 |
| 24 | S103G | IC | IC | 5.56E−09 | 7.40 |
| 25 | S103H | 1.26E−08 | 16.45 | 6.68E−09 | 4.63 |
| 26 | S103I | 1.01E−08 | 11.49 | 6.51E−09 | 4.41 |
| 27 | S103K | NB | NB | 4.75E−08 | 0.64 |
| 28 | S103L | 8.52E−08 | 4.59 | 1.59E−08 | 1.66 |
| 29 | S103M | 4.62E−09 | 15.21 | 1.04E−09 | 27.30 |
| 30 | S103N | 1.19E−07 | 0.95 | 1.01E−09 | 41.43 |
| 31 | S103P | 2.84E−08 | 11.18 | 7.79E−09 | 2.92 |
| 32 | S103Q | 9.68E−08 | 0.92 | 2.55E−10 | 123.85 |
| 33 | S103R | NB | NB | 4.56E−08 | 0.75 |
| 34 | S103T | 2.96E−08 | 3.88 | 1.27E−10 | 248.92 |
| 35 | S103V | 7.39E−09 | 14.70 | 3.82E−09 | 7.80 |
| 36 | S103W | 1.16E−07 | 0.94 | 1.61E−09 | 27.03 |
| 37 | S103Y | 4.39E−09 | 26.65 | 3.03E−09 | 10.41 |

NB: no binding detected under conditions used
IC: inconclusive data

BIACORE® results of CHOt supernatants suggested that at least four HC variants (N101D, N101E, N101S, and N101T) maintained similar binding to monomeric (hGITR.mmh) and dimeric (hGITR.mFc) GITR compared to CompAb1. See Table 5.

Notably, many variants lost GITR binding relative to GITR binding by the parent antibody. Of the N101 variant candidates that maintained similar binding to GITR as compared to CompAb1, four were selected for further characterization. These variants were produced in a CHO stable (CHOs) cell line and were subsequently purified.

For purified antibodies, BIACORE® experiments were performed as follows. Using a BIACORE® T-200 instrument, antibodies were captured for 30 seconds at a flow rate of 8 uL/min on a CM5 anti-humanFc-coupled surface. Approximately 120 RU of each antibody were captured. 10 nM hGITR.mmH (soluble monomeric hGITR, SEQ ID NO: 45) or 5 nM hGITR.mFc (dimeric Macaca fasicularis GITR, SEQ ID NO: 46) were injected over this surface for 5 minutes at a flow rate of 50 uL/min. Dissociation was measured for 10 min. The $K_D$ and $t_{1/2}$ were calculated by fitting the double-referenced sensorgrams to a 1:1 binding model.

The $K_D$ and $t_{1/2}$ of the four purified N101 variants to monomeric (hGITR.mmh) and dimeric (hGITR.mFc) GITR compared to CompAb1 are shown in Table 6.

TABLE 6

BIACORE® Binding Affinities of Variants Produced by CHO Cells

| | | hGITR.mmH | | hGITR.mFc | |
|---|---|---|---|---|---|
| anti-GITR mAb | Ref # | KD (M) | t1/2 (min) | KD (M) | t1/2 (min) |
| CompAb1 | CompAb1 | 1.51E−09 | 6.75 | 1.37E−10 | 35.57 |
| N101D Variant | mAb1 | 1.18E−09 | 7.58 | 1.04E−10 | 71.74 |
| N101E Variant | mAb2 | 1.13E−08 | 2.80 | 9.02E−10 | 9.55 |
| N101S Variant | mAb3 | 6.05E−09 | 4.65 | 8.82E−10 | 5.56 |
| N101T Variant | mAb4 | 8.00E−09 | 2.25 | 6.63E−10 | 10.03 |

Example 4. Heavy and Light Chain Variable Region Amino Acid and Nucleic Acid Sequences Table 7 sets forth the amino acid sequence identifiers of the heavy and light chain variable regions and CDRs of anti-GITR antibody variants of the CompAb1 antibody. The corresponding nucleic acid sequence identifiers are set forth in Table 8.

TABLE 7

Amino Acid Sequence Identifiers

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| mAb1 | 22 | 4 | 6 | 24 | 10 | 12 | 14 | 16 |
| mAb2 | 28 | 4 | 6 | 30 | 10 | 12 | 14 | 16 |
| mAb3 | 34 | 4 | 6 | 36 | 10 | 12 | 14 | 16 |
| mAb4 | 40 | 4 | 6 | 42 | 10 | 12 | 14 | 16 |

TABLE 8

Nucleic Acid Sequence Identifiers

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| mAb1 | 21 | 3 | 5 | 23 | 9 | 11 | 13 | 15 |
| mAb2 | 27 | 3 | 5 | 29 | 9 | 11 | 13 | 15 |
| mAb3 | 33 | 3 | 5 | 35 | 9 | 11 | 13 | 15 |
| mAb4 | 39 | 3 | 5 | 41 | 9 | 11 | 13 | 15 |

As will be appreciated by a person of ordinary skill in the art, an antibody having a particular Fc isotype can be converted to an antibody with a different Fc isotype, but in any event, the variable domains (including the CDRs) —which are indicated by the numerical identifiers shown in Tables 7 and 8—will remain the same, and the binding properties are expected to be identical or substantially similar regardless of the nature of the Fc domain.

Table 9 provides exemplary full length heavy chain (HC) and light chain (LC) nucleic acid and amino acid sequence identifiers for selected anti-GITR antibodies.

TABLE 9

Sequence Identifiers for full length heavy and light chain sequences for exemplary anti-GITR antibodies

| Antibody Designation | SEQ ID NOS: | | | |
|---|---|---|---|---|
| | Full length Heavy Chain | | Full length Light Chain | |
| | Nucleic Acid | Amino Acid | Nucleic Acid | Amino Acid |
| mAb1 | 25 | 26 | 19 | 20 |
| mAb2 | 31 | 32 | 19 | 20 |
| mAb3 | 37 | 38 | 19 | 20 |
| mAb4 | 43 | 44 | 19 | 20 |

Example 5. Assessment and Quantification of Truncation in Variants of Anti-GITR Antibody CompAb1

As described above, a truncated variant of full length anti-GITR antibody CompAb1 was identified. The mass of the truncated form corresponded to a cleavage between residues $N^{101}$ and $P^{102}$ in the CDR3 region of CompAb1 heavy chain. New antibody variants with a single amino acid substitution at the $N^{101}$ position of the $N^{101}/P^{102}$ truncation site in CompAb1 were subsequently created. These new antibody variants were analyzed to confirm their identities and to determine whether the new variants displayed truncation.

Denaturing SEC (which runs at a low temperature and mild pH) was employed to analyze variant truncation. CompAb1 and mAb1 were diluted to 1 mg/mL and 5 μg of each sample was injected onto a Waters ACQUITY UPLC BEH200 SEC column (1.7 μm, 4.6 mm×300 mm). The column was equilibrated with 100% of mobile phase A (30% acetonitrile, 0.1% formic acid, 0.1% trifluoroacetic acid in MILLI-Q® water) prior to sample injection. The column temperature was off. Proteins were eluted isocratically using a Waters ACQUITY UPLC system at 100% of mobile phase A using a flow rate of 0.10 mL/min over 5 minutes.

Analysis of the intact antibody by denaturing SEC-MS with no column heating showed no truncation in mAb1 and mAb2 (Table 10). These results were confirmed when variants were analyzed by reduced peptide mapping and LC-MS (data not shown).

TABLE 10

Percent truncation measured in CompAb1 and $N^{101}$ variants.

| Sample Name | Variant | Percent Truncation (%) by SEC-MS |
|---|---|---|
| CompAb1 | N/A | 3.7 |
| mAb1 | N101D | 0 |
| mAb2 | N101E | 0 |
| mAb3 | N101S | NA |
| mAb4 | N101T | NA |

NA: Not analyzed

Example 6: No Truncation Observed in N101D and N101E Variants of CompAb1 in Serum Stability Analysis CompAb1 and the variant candidates that were most like the original candidate in terms of binding to human GITR protein via BIACORE®, mAb1 (N101D) and mAb2

Figure 3:
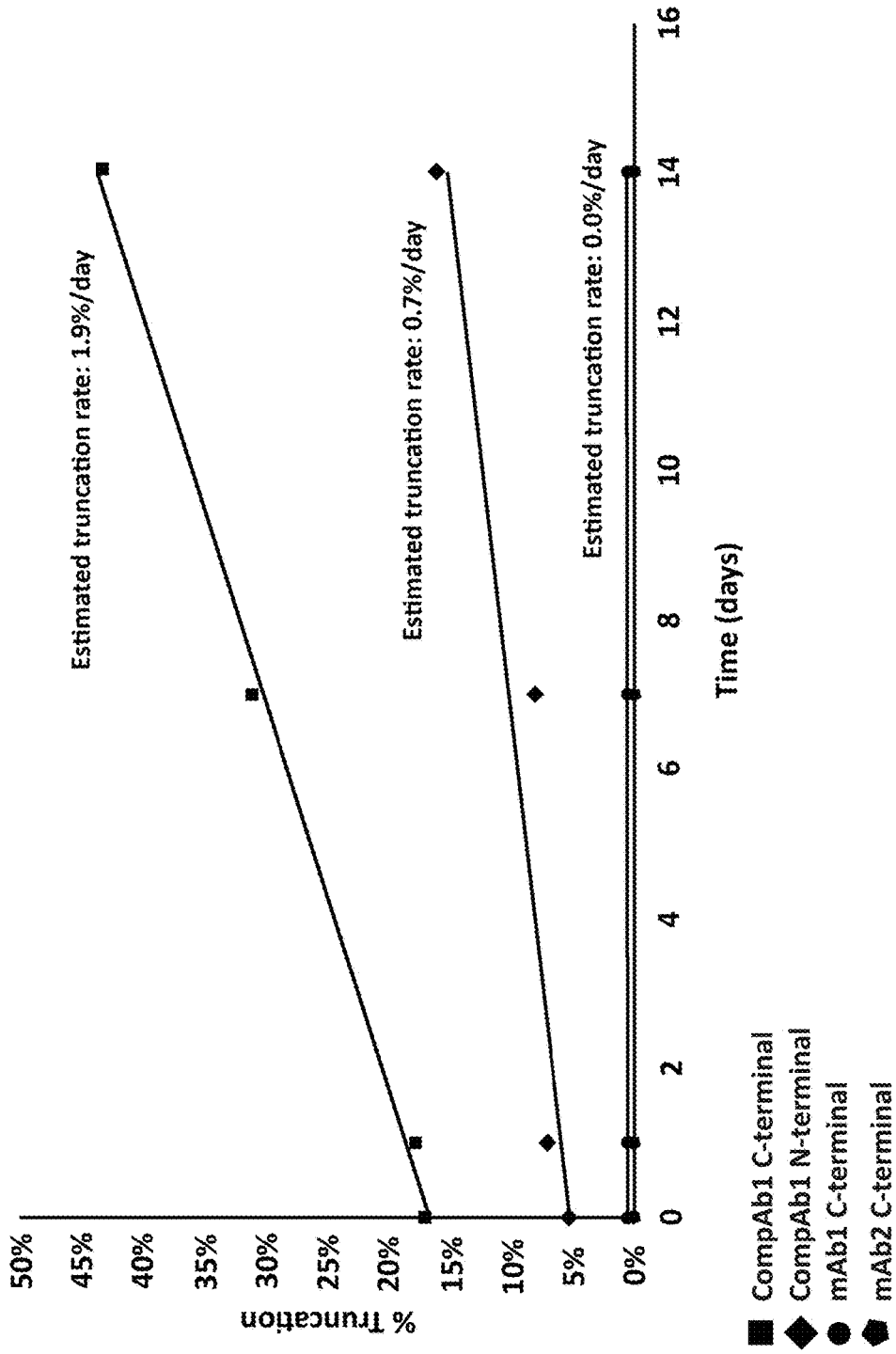
FIG. 3 depicts the increase in truncation observed in the CompAb1 antibody and none in variants mAb1 or mAb2 after incubation in IgG-depleted human serum. The CompAb1 antibody exhibited truncation rates of 1.9%/day at the C-terminal and 0.7%/day at the N-terminal.
Figure 4:
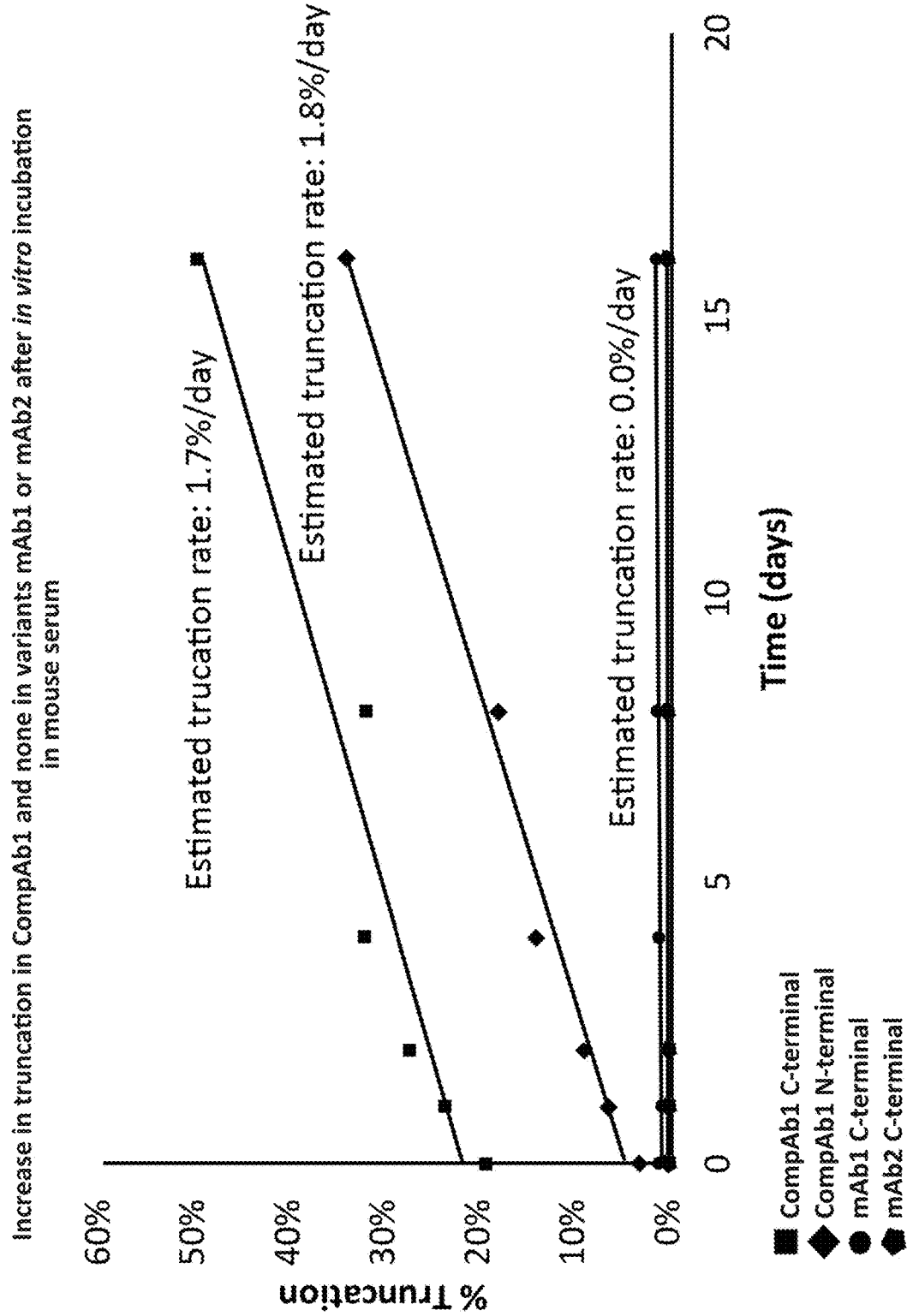
FIG. 4 depicts the increase in truncation observed in the CompAb1 (also referred to as CompAb1) antibody and none in variants mAb1 or mAb2 after in vitro incubation in mouse serum. In mouse serum, the estimated truncation rate for the CompAb1 antibody was at least 1.7%/day.

(N101E) (see previous example), were incubated in IgG-depleted human serum and mouse serum and HEPES buffer at 37° C. to test their stability under physiological conditions. In addition, CompAb1, mAb1 and mAb2 were dosed in mice (10 mg/kg) and serum was collected after 4 hours, 1, 2, 4, and 8 days. The antibodies were affinity purified by anti-Fc pull down and digested using Lys-C. The Lys-C digest and LC-MS method only used low temperatures for antibody denaturation and low column temperatures to prevent artificial truncation of the N101D variant. The levels of truncation increased in the CompAb1 molecule after serum incubation, but no truncation was detected in mAb1 or mAb2 across the entire time course (FIG. 3 and FIG. 4). Similarly, truncation was detected at variable levels in CompAb1 dosed in mice, but not in variants mAb1 or mAb2. See Table 11.

Fixable Green Dead Cell Stain according to the manufacturer's instructions. Cells were fixed with BD Cytofix and filtered through an ACROPREP™ Advance Filter Plate prior to acquisition on the Intellicyt iQue Screener PLUS flow cytometer. Data were analyzed with FLOWJO® software. For $EC_{50}$ (effective concentration at 50% activity) determinations, measured geometric MFI values were analyzed using a 4-parameter logistic equation over a 9-point response curve with GRAPHPAD PRISM®. The fold binding was determined by taking the ratio of the highest MFI on the curve to the MFI of the wells containing secondary antibody only.

TABLE 11

In vitro and in vivo stability of mAb1 and mAb2

| Antibody Stability Assay | | CompAb1 % Truncation | mAb1 (N101D) % Truncation | mAb2 (N101E) % Truncation |
|---|---|---|---|---|
| In Vitro Serum Incubation | Human | N-term fragment: (T = 0): 5.2%; (T = 14): 15.0% Rate: 0.7%/day C-term fragment: (T = 0): 16.7%; (T = 14): 45.0% Rate: 1.9%/day | Not Detected | Not Detected |
| | Mouse | N-term fragment: (T = 0): 5.0%; (T = 16): 33.0% Rate: 1.8%/day C-term fragment: (T = 0): 22.0%; (T = 16): 50% Rate: 1.7%/day | Not Detected | Not Detected |
| In Vivo Stability | Mouse | Variable levels of truncation observed | Not Detected | Not Detected |

Example 7. Anti-GITR Antibody Binding to Cell-Surface GITR

Figures 5A, 5B, 5C:
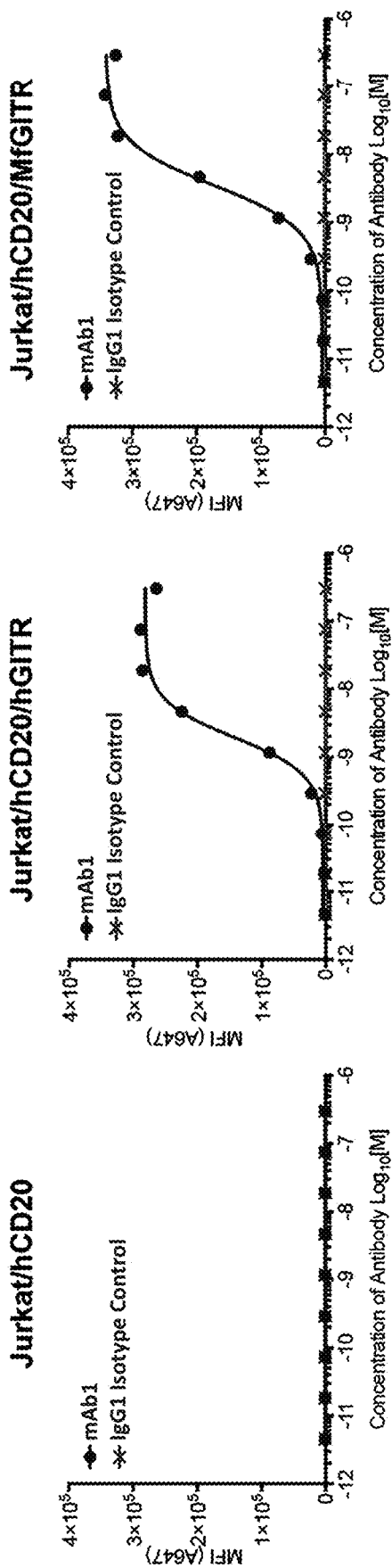
FIG. 5A, FIG. 5B, and FIG. 5C depict cell-surface binding of mAb1 and IgG1 isotype control at a range of concentrations (18 μM to 300 nM) on Jurkat/hCD20 (FIG. 5A), Jurkat/hCD20/hGITR (FIG. 5B), and Jurkat/hCD20/MfGITR (FIG. 5C) cells. Binding was detected using an Alexa647-labeled anti-human IgG by flow cytometry. Fluorescence intensity was plotted as geometric MFI. h, Human; Mf, *Macaca fascicularis* (cynomolgus monkey).

Flow cytometry was used to evaluate mAb1 binding to Jurkat/hCD20/hGITR cells and Jurkat/hCD20/MfGITR cells. Jurkat/hCD20 cells were used as a negative control cell line for GITR binding. Cells were added to a 96-well V-bottom plate ($2 \times 10^5$ to $4 \times 10^5$ cells/well) and incubated in Fc block solution, followed by successive incubation on ice with primary antibody (mAb1 or IgG1 isotype control) at final concentrations ranging from 18 pM to 300 nM and a secondary antibody (AF647-conjugated anti-human IgG) at 5 μg/mL. Cells were then stained with LIVE/DEAD® mAb1 displayed concentration-dependent binding to Jurkat/hCD20 cells engineered to express either hGITR or MfGITR cells with $EC_{50}$ values in the nanomolar range; no binding to Jurkat/hCD20 cells was detected (FIG. 5). The IgG1 isotype control displayed no binding to any of the 3 cell lines tested. $EC_{50}$ values (where applicable), the maximum MFI (highest mean MFI within tested dose range), and the fold binding calculated as the maximum MFI above background (secondary antibody alone) was reported for mAb1 and the IgG1 isotype control. Results are summarized in Table 12.

TABLE 12

Antibody Binding to Jurkat T-cells Engineered to Express Human or Cynomolgus Monkey GITR

| | Jurkat/hCD20 | | | Jurkat/hCD20/hGITR | | | Jurkat/hCD20/MfGITR | | |
|---|---|---|---|---|---|---|---|---|---|
| Antibody | Max MFI [a] | Fold Binding [b] | $EC_{50}$ (M) | Max MFI [a] | Fold Binding [b] | $EC_{50}$ (M) | Max MFI [a] | Fold Binding [b] | $EC_{50}$ (M) |
| mAb1 | 980 | 1.06 | ND | 289003 | 290 | 1.96E−09 | 342865 | 277 | 3.52E−09 |
| IgG1 Isotype Control | 1071 | 1.15 | ND | 1090 | 1.09 | ND | 1361 | 1.10 | ND |

[a] The maximum MFI was the highest mean MFI value within the concentration range tested (18 pM to 300 nM).
[b] Fold binding was calculated as the maximum MFI above background (secondary antibody alone).
h, Human;
Mf, *Macaca fascicularis* (cynomolgus monkey);
ND, Not determined because concentration-dependent binding was not observed In summary, mAb1 displayed concentration-dependent binding to Jurkat/hCD20 target cells expressing human or monkey GITR with similar potency ($EC_{50}$) and fold maximum binding.

Example 8: Anti-GITR Antibody Binding to Activated Human and Cynomolgus Monkey Primary T-cells In this experiment, mAb1 binding to anti-CD3/anti-CD28-stimulated human and cynomolgus monkey primary T-cells was evaluated. CD25 and CD69 were used as surrogate markers for human and cynomolgus monkey primary T-cell activation, respectively.

Peripheral blood mononuclear cells (PBMC) were isolated from human or cynomolgus monkey whole blood (4 donors each) using density centrifugation through FICOLL-PAQUE® PLUS in SEPMATE® tubes (for human PBMC) or 50 mL conical tubes (for cynomolgus monkey PBMC) and transferred to a fresh conical tube for incubation in Red Blood Cell (RBC) Lysis Buffer. PBMC were then washed and transferred to T75 culture flask for T-cell activation and expansion using a T-Cell Activation/Expansion Kit for human or non-human primate. After 4 days, activation beads were removed from the culture using a MACSiMAG™ Separator, and cells were collected and counted.

Figure 6:
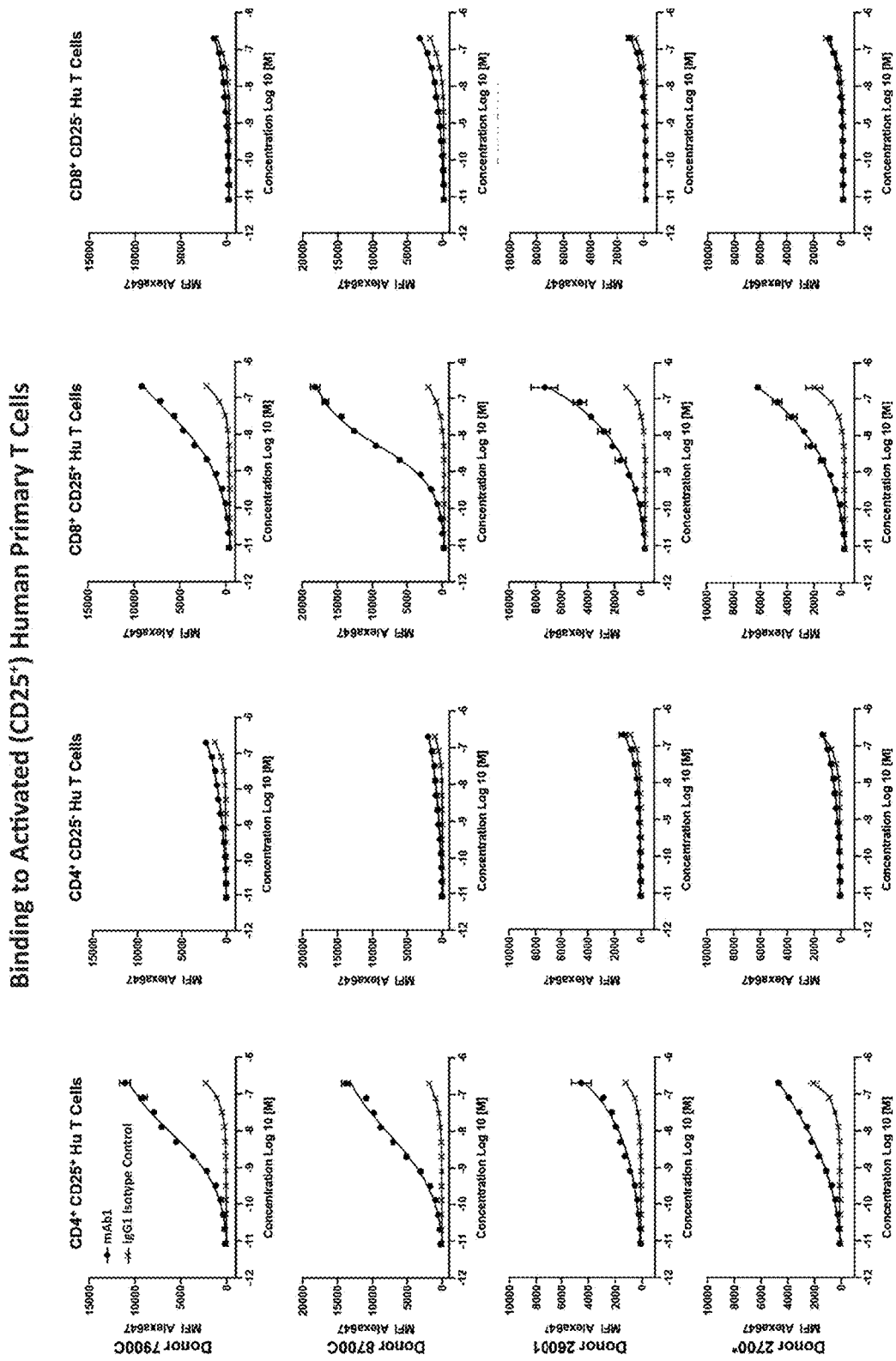
FIG. 6 depicts antibody binding to activated (CD25+) human primary T-cells. Primary human T-cells from 4 separate donors were stimulated in vitro with anti-CD2/anti-CD3/anti-CD28-coated beads. Cell-surface binding of AF647-conjugated mAb1 and AF647-conjugated IgG1 isotype control at a range of concentrations (8 pM to 200 nM) on CD25$^+$ and CD25$^-$ human primary CD4$^+$ and CD8$^+$ T-cells was detected using flow cytometry. Fluorescence intensity was plotted as geometric MFI. Hu, human
Figure 7:
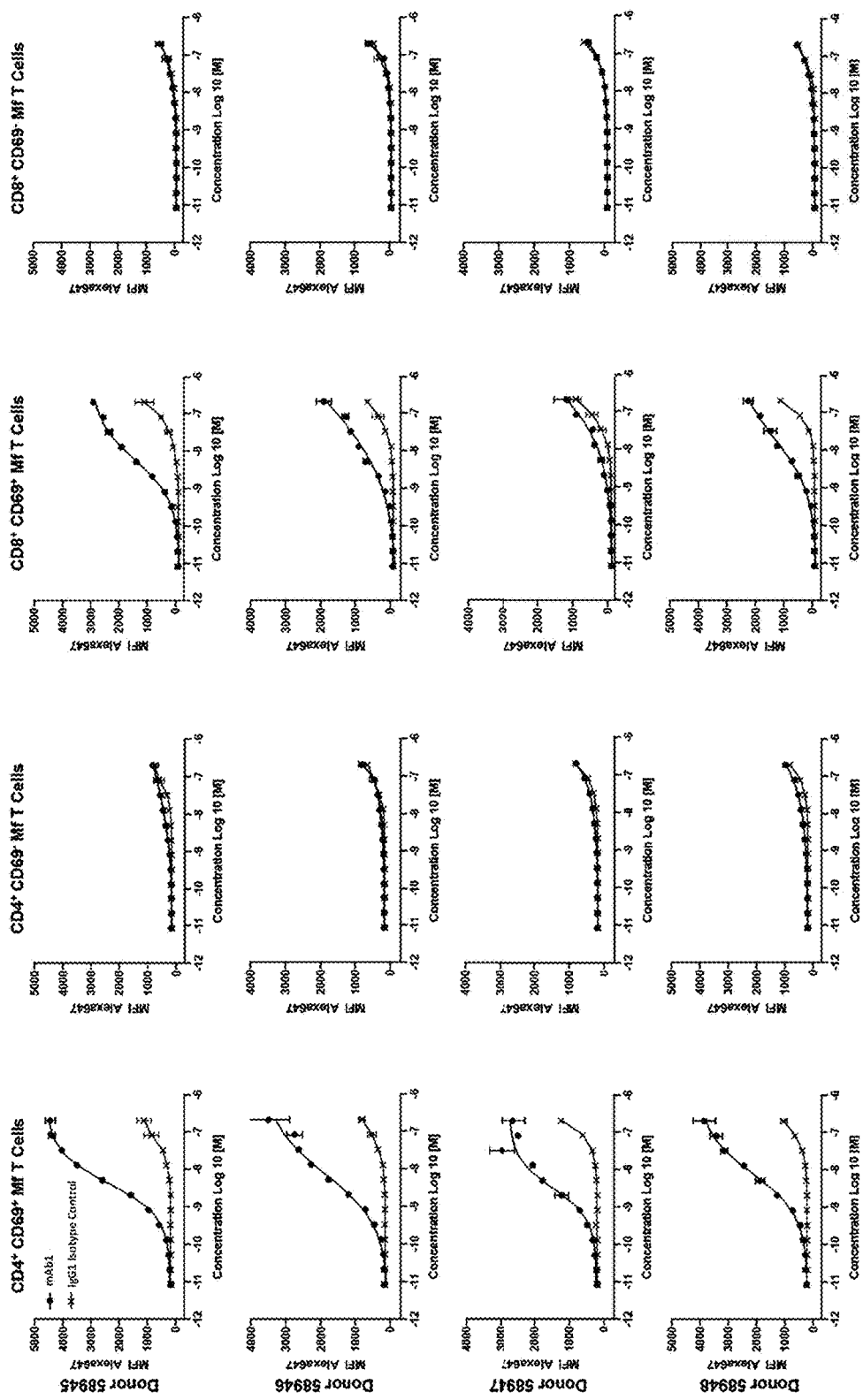
FIG. 7 depicts antibody binding to CD69+ cynomolgus monkey primary T-cells. Primary cynomolgus monkey T-cells from 4 separate donors were stimulated in vitro with anti-CD2/anti-CD3/anti-CD28-coated beads. Cell-surface binding of AF647-conjugated mAb1 and AF647-conjugated IgG1 isotype control at a range of concentrations (8 pM to 200 nM) on CD69$^+$ and CD69$^-$ cynomolgus monkey primary CD4$^+$ and CD8$^+$ T-cells was detected using flow cytometry. Fluorescence intensity was plotted as geometric MFI. Mf, *Macaca fascicularis* (cynomolgus monkey)

Flow cytometry was used to evaluate mAb1 binding to human or cynomolgus monkey T-cells in activated PBMC. Cells were added to a 96-well V-bottom plate ($3\times10^5$ cells/well) and incubated in Fc block/monocyte block solution, followed by incubation on ice with a T-cell phenotyping cocktail of fluorophore-conjugated antibodies (anti-CD3, anti-CD4, anti-CD8, and anti-CD25 [activation marker for human T-cells] or anti-CD69 [activation marker for cynomolgus monkey T-cells]), AF647-conjugated mAb1 or AF647-conjugated IgG1 isotype control (final concentrations ranging from 8 pM to 200 nM), and LIVE/DEAD® Fixable Blue Dead Cell Stain (according to the manufacturer's instructions). Cells were fixed with BD Stabilizing Fixative and filtered through an ACROPREP™ Advance Filter Plate prior to acquisition on a BD LSRFORTESSA® X-20 flow cytometer. Data were analyzed with FLOWJO® software. For $EC_{50}$ determinations, measured geometric MFI values were analyzed using a 4-parameter logistic equation over a 12-point response curve with GRAPHPAD PRISM®.

mAb1 displayed concentration-dependent binding to activated human and cynomolgus monkey primary T-cells. mAb1 displayed minimal binding, comparable to the IgG1 isotype control, to non-activated human and cynomolgus monkey primary T-cells (FIG. 6 and FIG. 7). The maximum MFI values (detected at 200 nM, the highest concentration tested) for mAb1 and the IgG1 isotype control binding are summarized in Tables 13 and 14.

TABLE 13

Anti-GITR Antibody Binding to Activated (CD25$^+$) and Non-Activated (CD25$^-$) Human Primary T-cells

| Human Primary T-Cell Subset | Donor | mAb1 | Max MFI[a] IgG1 Isotype Control |
|---|---|---|---|
| CD4$^+$ CD25$^+$ | 7900C | 11113 | 2283 |
|  | 8700C | 13815 | 1921 |
| CD4$^+$ CD25$^-$ | 26001 | 4537 | 1227 |
|  | 2700* | 4694 | 2085 |
|  | 7900C | 2324 | 1331 |
|  | 8700C | 2085 | 1056 |
| CD8$^+$ CD25$^+$ | 26001 | 1367 | 827 |
|  | 2700* | 1331 | 1406 |
|  | 7900C | 9180 | 2086 |
|  | 8700C | 18177 | 1971 |
| CD8$^+$ CD25$^-$ | 26001 | 7308 | 1102 |
|  | 2700* | 6183 | 1991 |
|  | 7900C | 1375 | 1139 |
|  | 8700C | 3243 | 1778 |
|  | 26001 | 1082 | 644 |
|  | 2700* | 835 | 1126 |

[a]The maximum MFI was determined at a non-saturating concentration of 200 nM (the highest concentration tested).

TABLE 14

Binding to Activated (CD69$^+$) and Non-Activated (CD69$^-$) Cynomolgus Monkey Primary T-cells

| Cynomolgus Monkey Primary T-Cell Subset | Donor | mAb1 | Max MFI[a] IgG1 Isotype Control |
|---|---|---|---|
| CD4$^+$ CD69$^+$ | 58945 | 4454 | 1112 |
|  | 58946 | 3496 | 803 |
|  | 58947 | 2624 | 1229 |
|  | 58948 | 3856 | 1027 |
| CD4$^+$ CD69$^-$ | 58945 | 818 | 730 |
|  | 58946 | 798 | 650 |
|  | 58947 | 803 | 825 |
|  | 58948 | 987 | 817 |
| CD8$^+$ CD69$^+$ | 58945 | 2909 | 1093 |
|  | 58946 | 1909 | 650 |
|  | 58947 | 1185 | 921 |
|  | 58948 | 2250 | 1128 |
| CD8$^+$ CD69$^-$ | 58945 | 479 | 565 |
|  | 58946 | 584 | 455 |
|  | 58947 | 458 | 601 |
|  | 58948 | 558 | 512 |

[a]The maximum MFI was determined at a non-saturating concentration of 200 nM (the highest concentration tested).

Example 9. NFAT Activation Via FcγR3a in Engineered Jurkat T-Cells

ADCC reporter bioassays (Parekh et al., mAbs, 4(3): 310-318, 2012) were developed to evaluate the ability of mAb1 to mediate Nuclear Factor of Activated T-cells (NFAT) activation via human or cynomolgus monkey FcγR3a (an Fc-receptor that mediates ADCC and is predominantly expressed on NK cells). Jurkat/NFAT-Luc/hFcγR3a or Jurkat/NFAT-Luc/MfFcγR3a effector cells and Jurkat/hCD20/hGITR or Jurkat/hCD20/MfGITR target cells were employed in these assays. Jurkat/hCD20 cells were evaluated as control target cells.

mAb1 or IgG1 isotype control (final concentrations ranging from 916fM to 60 nM) or an anti-CD20 IgG1 (final concentrations ranging from 45.8fM to 3 nM) were incubated in duplicate with effector cells ($2.5 \times 10^4$ cells/well) in the presence of target cells ($5 \times 10^4$ cells/well) in Jurkat complete media (RPMI supplemented with 10% fetal bovine serum (FBS), 100 U/mL penicillin, 100 µg/mL streptomycin, and 292 µg/mL L-glutamine). Wells containing no antibody were included as a control for background signaling. Plates were incubated at 37° C., 5% $CO_2$ for 5 hours. Plates were then equilibrated to room temperature for 10 minutes, followed by the addition of ONE-GLO™ luciferase substrate to the wells for 3 minutes. The luciferase activity was captured as luminescence signal and expressed as relative light units (RLU) using an ENVISION® plate reader. For $EC_{50}$ determinations, RLU values were analyzed using a 4-parameter logistic equation over a 9-point response curve with GRAPHPAD PRISM®. The fold change in activity was determined by taking the ratio of the highest RLU on the curve to the RLU of the wells containing no antibody.

Results are summarized in Table 15. mAb1 mediated a concentration-dependent increase in NFAT signaling in Jurkat/NFAT-Luc/hFcγR3a and Jurkat/NFAT-Luc/MfFcγR3a in the presence of Jurkat/hCD20/hGITR or Jurkat/hCD20/MfGITR, respectively, with subnanomolar $EC_{50}$ values (FIG. 8). The positive assay control, anti-CD20 IgG1, mediated a concentration-dependent increase in NFAT signaling in Jurkat/NFAT-Luc/hFcγR3a and Jurkat/NFAT-Luc/MfFcγR3a in the presence of Jurkat/hCD20 and either Jurkat/hCD20/hGITR or Jurkat/hCD20/MfGITR, respectively, with subnanomolar $EC_{50}$ values. No increase in baseline NFAT activation was observed with either mAb1 or the anti-CD20 IgG1 in the absence of target cells (i.e., media with no cells in addition to effector cells) or with the IgG1 isotype control in any condition tested.

Example 10: Anti-GITR Antibody Mediation of ADCC Against Jurkat T-cells Engineered to Express Human or Cynomolgus Monkey GITR ADCC assays were performed to assess the ability of mAb1 to induce ADCC against T-cells expressing human or cynomolgus monkey GITR. In the first experiment, target cells included Jurkat/hCD20/hGITR cells or Jurkat/hCD20/MfGITR cells; Jurkat/hCD20 cells were included as a control target cell line. In the second experiment, target cells included stimulated/expanded Tregs (regulatory T-cells) and $CD8^+$ T-cells from human PBMC (from the same 3 donors). Human NK cells isolated from leukocyte-enriched whole blood (from 2 donors for the assays with engineered Jurkat T-cells and from 2 donors for the assays with primary T-cells) were used as effector cells in the ADCC assays. An IgG1 isotype control was evaluated in parallel with mAb1. An anti-CD20 IgG1 or an anti-CD3 IgG1 was used as a positive control for inducing ADCC against engineered Jurkat T-cells and human primary T-cells, respectively, in the presence of NK cells.

mAb1 mediated concentration-dependent ADCC against Jurkat/hCD20/hGITR and Jurkat/hCD20/MfGITR (target cells) in the presence of human primary NK cells (effector cells); $EC_{50}$ values for cytotoxicity were in the subnanomolar range. In contrast, the IgG1 isotype control did not mediate ADCC against any of the target cell lines at concentrations ranging from 9.5fM to 10 nM. The addition of NK cells in the absence of antibody treatment resulted in a low percentage of nonspecific cytotoxicity against the target cell lines.

The NK cells were evaluated for their ability to induce ADCC against the same target cell lines using the positive control anti-CD20 IgG1. The anti-CD20 IgG1 mediated ADCC against Jurkat/hCD20, Jurkat/hCD20/hGITR, and Jurkat/hCD20/MfGITR target cells in a concentration-dependent manner with subnanomolar $EC_{50}$ values for cytotoxicity. Representative data for 2 human NK donors are shown in FIG. 9 and summarized in Table 16.

TABLE 15

Summary of mAb1-Mediated NFAT Activation in Jurkat/NFAT-Luc/hFcγR3a and Jurkat/NFAT-Luc/MfFcγR3a Effector Cells

| | +Jurkat/hCD20 Target Cells | | | +Jurkat/hCD20/hGITR Target Cells | | |
|---|---|---|---|---|---|---|
| Antibody | Max RLU [a] | Fold Change in Activity [b] | $EC_{50}$ (M) | Max RLU [a] | Fold Change in Activity [b] | $EC_{50}$ (M) |
| Jurkat/NFAT-Luc/hFcγR3a Effector Cells | | | | | | |
| mAb1 | 1.16E+04 | 1.01 | ND | 4.30E+05 | 38.0 | 3.20E−11 |
| IgG1 Isotype Control | 1.25E+04 | 1.12 | ND | 1.21E+04 | 1.14 | ND |
| Anti-CD20 IgG1 | 3.27E+05 | 28.1 | 2.10E−12 | 5.14E+05 | 47.0 | 2.01E−12 |
| Jurkat/NFAT-Luc/MfFcγR3a | | | | | | |
| mAb1 | 1.25E+04 | 1.02 | ND | 2.67E+05 | 23.9 | 1.60E−11 |
| IgG1 Isotype Control | 1.31E+04 | 1.05 | ND | 1.20E+04 | 1.09 | ND |
| Anti-CD20 IgG1 | 2.83E+05 | 22.1 | 9.95E−13 | 3.15E+05 | 28.6 | 1.58E−12 |

[a] The maximum RLU was determined as the highest mean RLU value within the concentration range tested (916 fM to 60 nM for mAb1 and the IgG1 isotype control and 45.8 fM to 3 nM for the anti-CD20 IgG1).
[b] Fold change in activity was calculated as the maximum RLU above background (no antibody).
h, Human;
Mf, Macaca fascicularis (cynomolgus monkey);
ND, Not determined because concentration-dependent luciferase activity was not observed

TABLE 16

Antibody-Mediated ADCC Against Engineered Jurkat T-cells

| | Jurkat/hCD20 | | | | Jurkat/hCD20/hGITR | | | | Jurkat/hCD20/MfGITR | | | |
|---|---|---|---|---|---|---|---|---|---|---|---|---|
| | Donor 6700R NK Cells | | Donor 6500V NK Cells | | Donor 6700R NK Cells | | Donor 6500V NK Cells | | Donor 6700R NK Cells | | Donor 6500V NK Cells | |
| Antibody | Max % Cytotoxicity[a] | $EC_{50}$ (M) | Max % Cytotoxicity[a] | $EC_{50}$ (M) | Max % Cytotoxicity[a] | $EC_{50}$ (M) | Max % Cytotoxicity[a] | $EC_{50}$ (M) | Max % Cytotoxicity[a] | $EC_{50}$ (M) | Max % Cytotoxicity[a] | $EC_{50}$ (M) |
| mAb1 | 9 | ND | 5 | ND | 27 | 1.30E−11 | 30 | 1.22E−11 | 26 | 1.21E−11 | 34 | 1.08E−11 |
| IgG1 Isotype Control | 9 | ND | 9 | ND | 8 | ND | 7 | ND | 3 | ND | 6 | ND |
| Anti-CD20 IgG1 | 28 | 2.49E−11 | 37 | 2.58E−11 | 35 | 5.30E−11 | 43 | 3.81E−11 | 34 | 5.18E−11 | 36 | 3.12E−11 |

[a] The maximum % cytotoxicity was determined as the highest mean percent cytotoxicity value within the concentration range tested (9.5 fM to 10 nM).
h, Human;
Mf, *Macaca fascicularis* (cynomolgus monkey);
ND, Not determined because concentration-dependent cytotoxicity was not observed Example 11: Anti-GITR Antibody Mediation on ADCC Against Human Primary T-cells PBMC were isolated from human whole blood (3 donors) via density centrifugation using FICOLL-PAQUE® PLUS density gradient medium and SEPMATE® tubes, following the manufacturer's recommended protocol. Subsequently, Red Blood Cell (RBC) Lysis Buffer was added to isolated PBMC to remove unwanted RBC. PBMC were then washed and CD8+ T-cells were isolated using CD8 Microbeads according to the manufacturer's instructions. The remaining CD8 negative cells were pelleted and CD4+ CD25+ T-cells were isolated using a CD4+ CD25+ Regulatory T-Cell Isolation Kit, according to the manufacturer's protocol.

The isolation of CD8+ and CD4+/CD25+ T-cells (i.e., Tregs) was confirmed using flow cytometry. CD8+ T-cells were seeded into T75 flasks with media supplemented with IL-2 for expansion using CD3/CD28 Dynabeads according to the manufacturer's instructions (1 bead:1 cell). Tregs were seeded into T75 flasks with media supplemented with IL-2 and rapamycin for expansion using CD3/CD28 MACI-BEAD™ particles according to the manufacturer's instructions (4 beads:1 cell). Beads were removed after 5 days of culture, and cells were rested in media without IL-2 or rapamycin for 24 hours before use in the ADCC assay.

Prior to cytotoxicity assay, CD8+ T-cells and Tregs were stained as described in Example 8, and the antibody binding capacity (ABC), defined as the number of antibody molecules bound to the cell surface under saturating conditions, was assessed by flow cytometry. The ABC for a GITR antibody from Miltenyi Biotec was determined using a QUANTUM™ SIMPLY CELLULAR® AF647 MESF (molecules of soluble fluorochrome) bead kit according to manufacturer's instructions.

Target cells ($5 \times 10^3$ cells/well) were added in triplicate to opaque, white 96-well flat-bottom plates, followed by the addition of mAb1, IgG1 isotype control, or an anti-CD20 (for engineered Jurkat T-cells) or anti-CD3 (for human primary T-cells) IgG1 (final concentrations ranging from 9.5fM to 10 nM for engineered Jurkat T-cells from 169fM to 10 nM for human primary T-cells), and then the addition of human NK cells ($2.5 \times 10^4$ cells/well) in assay media (RPMI supplemented with 1% bovine serum albumin (BSA), 100 U/mL penicillin, 100 μg/mL streptomycin, and 292 μg/mL L-glutamine). A control sample that contained all components except the antibody was incorporated into each experiment to determine the background signal of the assay (i.e., nonspecific lysis of target cells in the presence of NK cells). To assess spontaneous lysis, untreated target cells alone (target cells) and effector cells alone (effector cells) were incubated in separate wells.

Plates were incubated at 37° C., 5% $CO_2$ for 3.5 hours. The plates were then equilibrated to room temperature for 10 minutes, followed by the addition of CYTOTOX GLO™ reagent to the wells for 15 minutes while shaking. The luminescence signal was measured as a readout of cytotoxicity using an ENVISION® plate reader.

mAb1 mediated concentration-dependent ADCC against human primary T-cells (target cells) from 3 of 3 donors tested in the presence of human primary NK cells (effector cells) with $EC_{50}$ values for cytotoxicity in the subnanomolar range. Of the 6 test conditions (2 effector cell donors×3 target cell donors), mAb1-mediated cytotoxicity was significantly greater against Tregs compared with CD8+ T-cells in 4 of the conditions. See FIG. 10 and Table 17.

In contrast, the IgG1 isotype control did not mediate ADCC against any of the primary T-cell donors. The addition of NK cells in the absence of antibody treatment resulted in a low percentage of nonspecific cytotoxicity against primary T-cells.

Figure 10A:
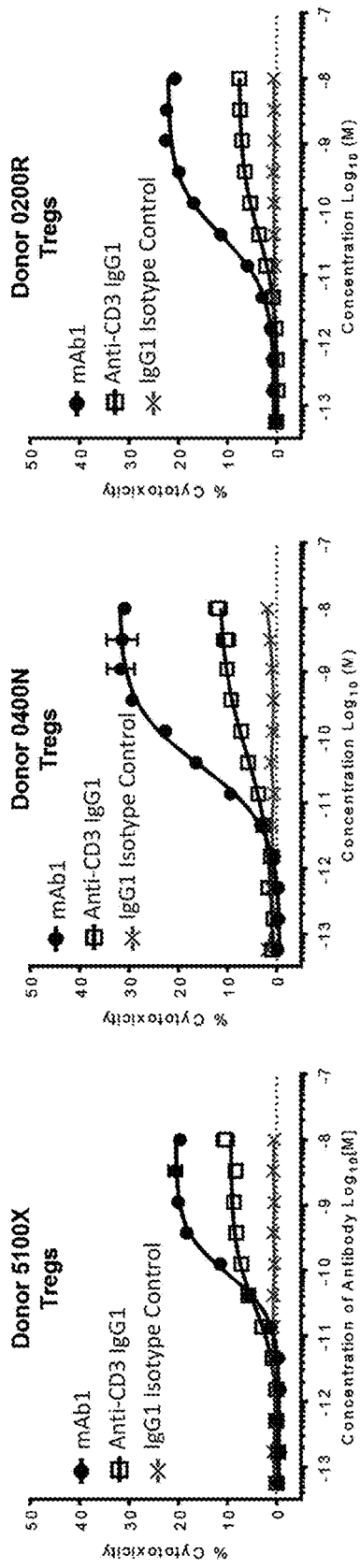
Figure 10B:
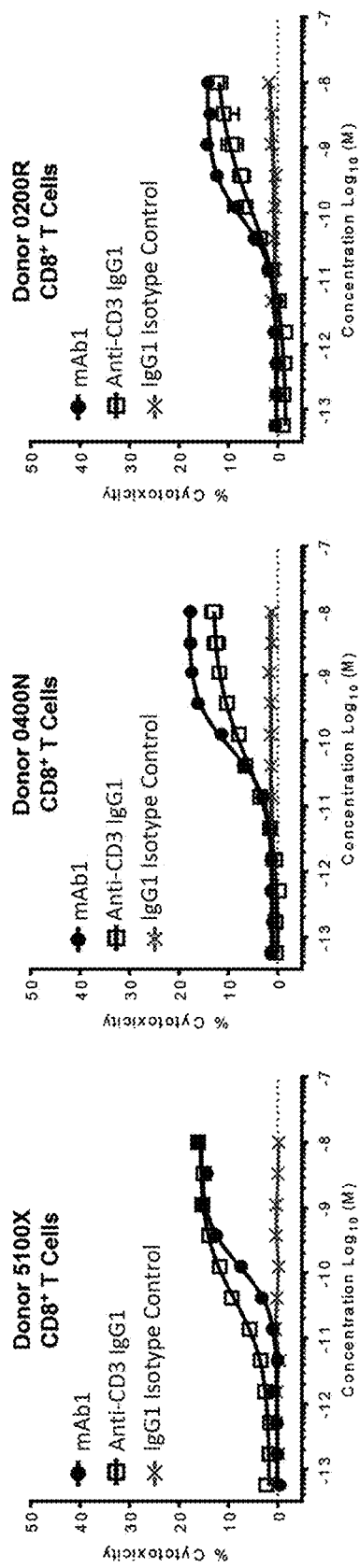

The NK cells were also evaluated for their ability to induce ADCC in assays using the same NK and T-cell donors with the positive control anti-CD3 IgG1. The anti-CD3 IgG1 mediated ADCC against primary T-cells in a concentration-dependent manner with subnanomolar $EC_{50}$ values for cytotoxicity. Representative data for 2 human primary NK donors tested with 3 human primary T-cell donors are shown in FIG. 10 and summarized in Table 17.

TABLE 17

Antibody-Mediated ADCC Against Human Primary T-cells

| | Tregs | | | | | | CD8+ T-cells | | | | | |
|---|---|---|---|---|---|---|---|---|---|---|---|---|
| | Donor 5100X GITR ABC: 57,069 | | Donor 0400N GITR ABC: 58,810 | | Donor 0200R GITR ABC: 57,243 | | Donor 5100X GITR ABC: 38,152 | | Donor 0400N GITR ABC: 12,712 | | Donor 0200R GITR ABC: 21,987 | |
| Antibody | Max % Cytotoxicity [a] | EC$_{50}$ (M) | Max % Cytotoxicity [a] | EC$_{50}$ (M) | Max % Cytotoxicity [a] | EC$_{50}$ (M) | Max % Cytotoxicity [a] | EC$_{50}$ (M) | Max % Cytotoxicity [a] | EC$_{50}$ (M) | Max % Cytotoxicity [a] | EC$_{50}$ (M) |
| | Donor 04003 NK Cells in the Presence of | | | | | | | | | | | |
| mAb1 [b] | 21 | 8.88E−11 | 32 | 3.72E−11 | 23 | 3.99E−11 | 16 | 1.28E−10 | 18 | 7.64E−11 | 14 | 8.41−11 |
| IgG1 Isotype Control | 0.8 | ND | 2 | ND | 0.7 | ND | 0.5 | ND | 2 | ND | 2 | ND |
| Anti-CD3 IgG1 [c] | 25 | 7.56E−11 | 29 | 4.54E−11 | 20 | 2.80E−11 | 27 | 6.48E−11 | 30 | 4.49E−11 | 26 | 1.15E−10 |
| | Donor 05001 NK Cells in the Presence of | | | | | | | | | | | |
| mAb1 [d] | 11 | 8.34E−11 | 17 | 4.49E−11 | 7 | 6.47E−11 | 11 | 9.51E−11 | 7 | 1.16E−10 | 9 | 1.39E−10 |
| IgG1 Isotype Control | 1 | ND | 3 | ND | 0.4 | ND | 2 | ND | 0.5 | ND | 1 | ND |
| Anti-CD3 IgG1 [c] | 11 | 2.88E−11 | 12 | 6.30E−11 | 8 | 4.35E−11 | 16 | 3.89E−11 | 13 | 5.54E−11 | 12 | 1.20E−10 |

[a] The maximum % cytotoxicity was determined as the highest mean percent cytotoxicity value within the concentration range tested (169 fM to 10 nM).
[b] mAb1 mediated significantly greater ADCC against Tregs compared to CD8$^+$ T-cells from Donor 0400N ($p < 0.0001$) and significantly greater ADCC against CD8$^+$ T-cells compared to Tregs from Donor 0200R ($p < 0.0001$).
[c] Anti-CD3 IgG1 mediated significantly greater ADCC against CD8$^+$ T-cells compared to Tregs from Donor 5100X ($p < 0.0001$).
[d] mAb1 mediated significantly greater ADCC against Tregs compared to CD8$^+$ T-cells from all 3 donors ($p < 0.0001$). Statistical significance of ADCC across all test conditions for each NK cell donor was determined by two-way ANOVA with Tukey's multiple comparisons post hoc test ($\alpha = 0.05$).
ABC, antibody binding capacity (bound antibodies per cell, calculated based on fluorescence intensity measured by flow cytometry);
ND, Not determined because concentration-dependent cytotoxicity was not observed Example 12: Anti-GITR Antibody Mediation of ADCP Against Jurkat T-Cells Engineered to Express Human or Cynomolgus Monkey GITR An ADCP (Antibody Dependent Cellular Phagocytosis) assay was performed to assess the ability of mAb1 to induce ADCP of T-cells expressing human or cynomolgus monkey GITR. Target cells included Jurkat/hCD20/hGITR cells or Jurkat/hCD20/MfGITR cells; Jurkat/hCD20 cells were included as a control target cell line. Phagocytes differentiated from CD14$^+$ monocytes in the presence of granulocyte-macrophage colony-stimulating factor (GM-CSF) were used as effector cells in the ADCP assay. An IgG1 isotype control was evaluated in parallel with mAb1. An anti-CD20 IgG1 was used as a positive control for inducing ADCP of engineered Jurkat T-cells.

Frozen CD14$^+$ cells obtained from Lonza were thawed, resuspended in cell culture media (RPMI supplemented with 10% FBS, 100 U/mL penicillin, 100 μg/mL streptomycin, and 292 μg/mL L-glutamine, 1% human AB serum, NaPyr (sodium pyruvate), HEPES, NEAA (non-essential amino acids), and 0.01 mM beta-mercaptoethanol) supplemented with 50 ng/mL GM-CSF, and plated at 5×10$^4$ cells/well into clear-bottom, collagen-coated 96-well black plates for differentiation into phagocytes over 13 days, with fresh GM-CSF (50 ng/ml) added on day 6 and day 12.

Target cells and monocyte-derived phagocytes were incubated with either CELLTRACE® CFSE (carboxyfluorescein succinimidyl ester) dye or CELLTRACE® Far Red dye, respectively, for 15 minutes at 37° C., 5% CO$_2$ for labeling prior to ADCP assay.

Target cells (5×10$^5$ cells/well) were added in duplicate to 96-well U-bottom plates, followed by the addition of mAb1, IgG1 isotype control, or an anti-CD20 IgG1 (final concentrations ranging from 381fM to 100 nM) in assay media (RPMI supplemented with 10% FBS, 100 U/mL penicillin, 100 μg/mL streptomycin, and 292 μg/mL L-glutamine) on ice for at least 15 minutes. Target cells without antibody were included as a control for background phagocytosis. The mixture of target cells, with or without titrated antibody, were then transferred to plates containing adhered, Far Red-labelled, phagocytes, and plates were incubated at 37° C., 5% CO$_2$ for 1 to 2 hours.

After incubation, media containing unattached cells were removed from the wells, and the wells were rinsed with PBS. A solution of 3.7% formaldehyde in PBS was added to the wells to fix the cells for 20 minutes. Wells were washed with PBS, and the plates were stored at 4° C. until analysis.

Phagocytosis was analyzed by fluorescence imaging on an OPERA PHOENIX® High-Content Screening System using Harmony software to acquire images in both the 488 nm (CFSE-labelled target cells) and 647 nm (Far Red-labelled phagocytes) emission channels. Image analysis was performed in Columbus software, and phagocytosis was quantified by performing image segmentation in the 647 nm emission channel to select the phagocyte population and calculating the 488 nm fluorescence intensity (from CFSE-labeled target cells) inside each phagocytic cell as relative fluorescence units (RFU). For EC$_{50}$ determinations, RFU values were analyzed using a 4-parameter logistic equation over a 10- or 9-point point response curve with GRAPHPAD PRISM® for assays with engineered Jurkat T-cells or human primary T-cells, respectively. The fold change in activity was determined by taking the ratio of the highest RFU on the curve to the RFU of the wells containing no antibody.

mAb1 mediated concentration-dependent ADCP of Jurkat/hCD20/hGITR and Jurkat/hCD20/MfGITR (target cells) in the presence of human primary monocyte-derived phagocytes (effector cells). An $EC_{50}$ value for phagocytosis of Jurkat/hCD20/hGITR could not be calculated because a 4-parameter logistic regression did not converge on a single value; the $EC_{50}$ value for phagocytosis of Jurkat/hCD20/MfGITR was in the subnanomolar range. Maximum levels of mAb1-mediated phagocytosis of Jurkat/hCD20/hGITR and Jurkat/hCD20/MfGITR cells were comparable, with 5.92 and 6.98-fold change in activity above background (no antibody), respectively. In contrast, the IgG1 isotype control did not mediate ADCP of any of the target cell lines. Data for 1 human primary monocyte-derived phagocytic cell donor is shown in FIG. 11 and summarized in Table 18.

The human primary monocyte-derived phagocytes were evaluated for their ability to induce ADCP of the same target cell lines using the positive control anti-CD20 IgG1. The anti-CD20 IgG1 mediated ADCP of Jurkat/hCD20, Jurkat/hCD20/hGITR, and Jurkat/hCD20/MfGITR target cells in a concentration-dependent manner with subnanomolar $EC_{50}$ values for phagocytosis.

On the day of the assay, the plated HEK293/FcγR2b cells were pre-incubated with 1.2 μg/mL OKT3 for 20 min at room temperature followed by the addition of the 5×10$^5$ naïve CD4$^+$ T-cells/well and either mAb1 or the IgG1 isotype control at final concentrations ranging from 32fM to 133 nM.

Plates were incubated for 4 days at 37° C., 5% $CO_2$, and 0.5 uCi tritiated thymidine was added to cells and the plates were incubated for another 16 hours. Thymidine, and therefore tritium, will be incorporated at higher amounts into dividing cells.

After the incubation, cells were harvested onto 96-well UNIFILTER® plates and 35 μL of scintillation fluid was added to each well. Tritium incorporation was measured as counts per minute (CPM) using the Microplate Scintillation & Luminescence Counter TopCount NXT instrument. All serial dilutions were tested in duplicates.

The $EC_{50}$ values of the antibodies were determined from a 4-parameter logistic equation over a 12-point dose-response curve using GRAPHPAD PRISM® software. Maximum proliferation was determined as the mean maximum CPM detected within the tested concentration range. The fold change in activity was determined by taking the ratio of the highest CPM on the curve to the CPM of the wells containing no antibody.

TABLE 18

Antibody-Mediated ADCP of Engineered Jurkat T-cells

| Antibody | Jurkat/hCD20 | | | Jurkat/hCD20/hGITR | | | Jurkat/hCD20/MfGITR | | |
|---|---|---|---|---|---|---|---|---|---|
| | Max RFU [a] | Fold Change in Activity [b] | $EC_{50}$ (M) | Max RFU [a] | Fold Change in Activity [b] | $EC_{50}$ (M) | Max RFU [a] | Fold Change in Activity [b] | $EC_{50}$ (M) |
| mAb1 | 3.29E+06 | 1.10 | ND | 1.76E+07 | 5.92 | NC | 2.03E+07 | 6.98 | 5.10E−10 |
| IgG1 Isotype Control | 3.25E+06 | 1.09 | ND | 3.18E+06 | 1.07 | ND | 2.95E+06 | 1.02 | ND |
| Anti-CD20 IgG1 | 1.05E+07 | 3.73 | 4.24E−10 | 1.11E+07 | 3.60 | 3.84E−10 | 1.45E+07 | 4.57 | 9.03E−10 |

[a] The maximum RFU was determined as the highest mean RFU value within the concentration range tested (381 fM to 100 nM).
[b] Fold change in activity was calculated as the maximum RFU above background (no antibody).
h, Human;
Mf, *Macaca fascicularis* (cynomolgus monkey);
NC, Not calculated because a unique fit could not be found for the data set;
ND, Not determined because concentration-dependent phagocytosis was not observed

Example 13: Effect of Anti-GITR Antibody on Anti-CD3-Mediated Primary CD4+ T-Cell Proliferation The effect of mAb1 on primary CD4+ T-cell proliferation mediated by a stimulatory CD3 antibody was evaluated in the presence of HEK293/FcγR2b accessory cells. Human primary CD4+ T-cells from 6 donors were evaluated.

HEK293/FcγR2b cells were incubated in 50 μg/mL mitomycin C for 30 min at 37° C., 5% $CO_2$ and seeded into a 96-well flat-bottom tissue culture plate at 1×10$^5$ cells/well overnight at 37° C., 5% $CO_2$.

CD4$^+$ T-cells were isolated from PBMC from 6 donors using density gradient centrifugation using a FICOLL-PAQUE® PLUS gradient followed by depletion of memory T-cells using human CD45RO microbeads following the manufacturer's protocol; naïve CD4$^+$ T-cells were resuspended in assay media (RPMI supplemented with 5% human AB serum, 100 U/mL penicillin, 100 μg/mL streptomycin, and 292 μg/mL L-glutamine).

mAb1 enhanced anti-CD3-mediated T-cell proliferation in a concentration-dependent manner with subnanomolar $EC_{50}$ values (FIG. 12) and was associated with 2.3- to 3.1-fold increases in maximum T-cell proliferation (measured as CPM from tritium decay) above background. In contrast, the IgG1 isotype control did not promote concentration-dependent enhancement of T-cell proliferation. Results are summarized in Table 19.

TABLE 19

Anti-GITR Antibody Effect on Anti-CD3-Mediated Primary CD4$^+$ T-Cell Proliferation

| | mAb1 | | | IgG1 Isotype Control | | |
|---|---|---|---|---|---|---|
| Donor | Max CPM [a] | Fold Change in Activity [b] | $EC_{50}$ (M) | Max CPM [a] | Fold Change in Activity [b] | $EC_{50}$ (M) |
| 1900G | 4875 | 3.14 | 4.30E−10 | 2620 | 1.69 | ND |
| 41003 | 5774 | 2.54 | NC | 2610 | 1.15 | ND |

TABLE 19-continued

Anti-GITR Antibody Effect on Anti-CD3-Mediated
Primary CD4⁺ T-Cell Proliferation

| | mAb1 | | | IgG1 Isotype Control | | |
|---|---|---|---|---|---|---|
| Donor | Max CPM[a] | Fold Change in Activity[b] | $EC_{50}$ (M) | Max CPM[a] | Fold Change in Activity[b] | $EC_{50}$ (M) |
| 3600Y | 2707 | 2.30 | 1.72E−08 | 1720 | 1.46 | ND |
| 34001 | 1401 | 2.62 | 1.93E−10 | 841 | 1.57 | ND |
| 2000U | 10722 | 2.45 | 3.91E−11 | 5631 | 1.29 | ND |
| 3800U | 1505 | 2.45 | 1.07E−10 | 1064 | 1.73 | ND |

[a] The maximum CPM was determined as the highest mean CPM value within the concentration range tested (32 fM to 133 nM).
[b] Fold change in activity was calculated as the maximum CPM above background (no antibody).
NC, Not calculated because a 4-parameter logistic regression did not converge on a single value;
ND, Not determined because concentration-dependent proliferation was not observed

Example 14: Effect of Anti-GITR Antibody on GITR Binding to GITR-L in a Blocking ELISA®

The binding of recombinant hGITR to its ligand, hGITR-L, was determined using an enzyme-linked immunosorbent assay (ELISA®)-based binding assay. Recombinant hGITR-L at a concentration of 2 µg/mL diluted in PBS was passively adsorbed to microtiter plate and incubated overnight at 4° C. followed by blocking with PBS with 0.5% BSA. Monomeric recombinant human GITR ectodomain protein, hGITR.mmH, at a range of concentrations (3.4 pM to 200 nM) was then added in duplicate to the plates. Plates were incubated for 1 hour at room temperature, followed by 4 washes with PBS containing 0.05% TWEEN®-20 (PBST). Plate-bound hGITR.mmH was detected with horseradish peroxidase (HRP) conjugated goat anti-cMyc antibody at 0.33 µg/ml and visualized using the colorimetric HRP substrate 3-3', 5-5'-tetramethylbenzidine (TMB) according to the manufacturer's recommended procedures. Absorbance data at 450 nm ($OD_{450}$) were plotted as a function of the concentration of recombinant hGITR.mmH. A buffer alone sample was included to determine background signal; however, its $OD_{450}$ was not plotted in the response curve. Binding data were analyzed using a 4-parameter logistic equation over an 11-point response curve with GRAPHPAD PRISM® software, and $EC_{50}$ values were calculated. $EC_{50}$ values are defined as the concentration of hGITR.mmH at which 50% of maximal binding was observed. A concentration near the $EC_{50}$ value (within the linear range) was selected as the fixed hGITR.mmH concentration for the blocking assay.

An ELISA®-based blocking assay was developed to determine the ability of mAb1 to block binding of recombinant human GITR (hGITR.mmH) to hGITR-L. A fixed concentration of recombinant hGITR.mmH (1.5 nM) was pre-incubated with mAb1 or IgG1 isotype control, (51pM to 3 µM) for 1 hour. The pre-incubated solutions were transferred to duplicate wells of microtiter plates that were previously coated with GITR-L as described above. Plates were incubated at room temperature for 1 hour, followed by 4 washes with PBST, and plate-bound hGITR.mmH was detected as described above. Absorbance data at $OD_{450}$ were plotted as a function of antibody concentrations. Binding data were analyzed using a 4-parameter logistic equation over an 11-point response curve with GRAPHPAD PRISM® software, and $IC_{50}$ values were calculated. $IC_{50}$ values are defined as the concentration of antibody required to block 50% of hGITR.mmH binding to plate-coated hGITR-L.

Figure 13:
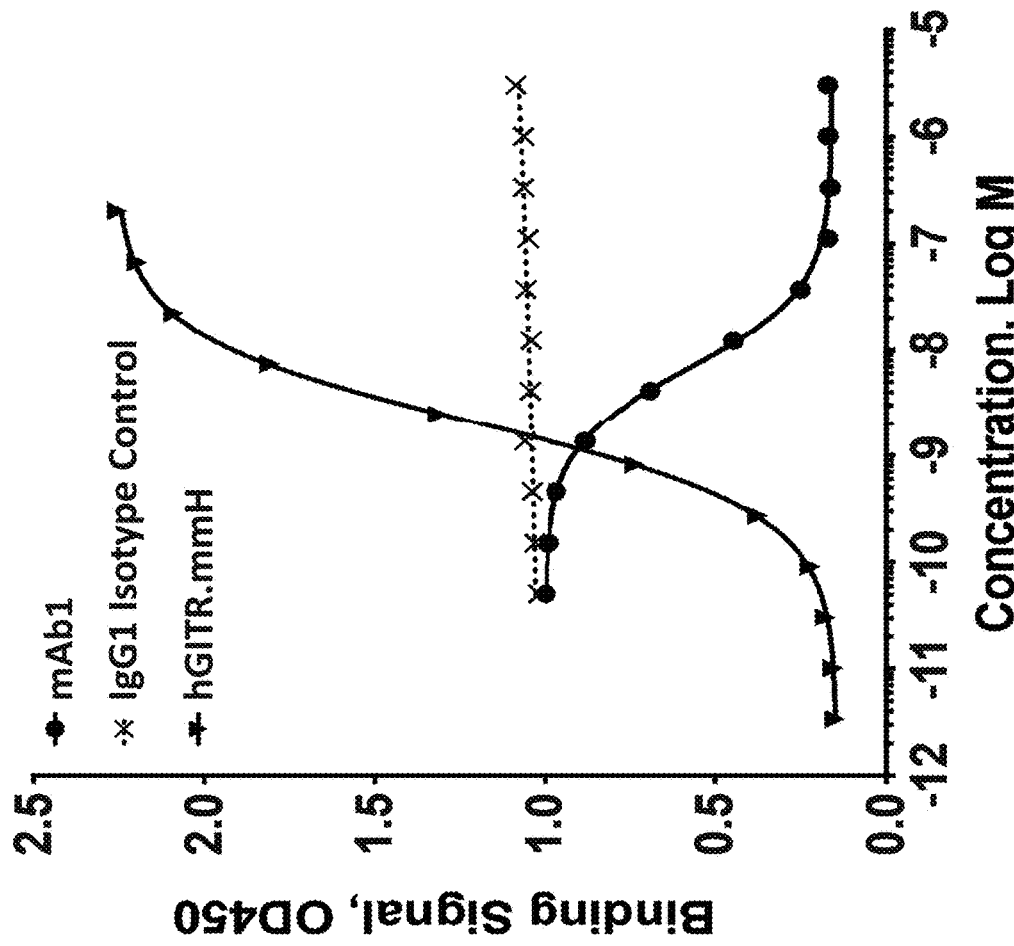
FIG. 13 depicts effects of anti-GITR antibody on human GITR binding to human GITR-L. Binding of human GITR protein, hGITR.mmH, at a range of concentrations (3.4 pM to 200 nM) to immobilized human GITR-L was evaluated by ELISA® and $EC_{50}$ values for binding were determined. A fixed concentration of recombinant hGITR.mmH (1.5 nM), based on the $EC_{50}$ values calculated for binding to hGITR-L, was pre-incubated with mAb1, or an IgG1 isotype control at a range of concentrations (51 pM to 3 pM) and added to wells containing immobilized human GITR-L to determine the ability of the antibodies to block hGITR.mmH binding to immobilized human GITR-L. Binding of hGITR.mmH was detected with an HRP-conjugated cMyc antibody using TMB substrate, and the $OD_{450}$ was measured by spectrophotometry.

The effect of mAb1 or an IgG1 isotype control on monomeric recombinant human GITR ectodomain protein (hGITR.mmH) binding to immobilized human GITR-L (6His.GCN4.G4S×3.hGITR-L) is shown in FIG. 13. The $IC_{50}$ values and maximum percent inhibition for the antibodies are summarized in Table 20.

TABLE 20

Blocking of hGITR.mmH Binding to Immobilized Human GITR-L

| Antibody | $IC_{50}$ (M) | % Max Inhibition |
|---|---|---|
| mAb1 | 6.66E−09 | 98 |
| IgG1 Isotype Control | ND | −6 |

% Maximum Blocking = Percent blockade at maximum concentration of the antibody
ND, Not determined because concentration-dependent inhibition of binding was not observed Recombinant hGITR.mmH bound immobilized human GITR-L in a concentration-dependent manner with an $EC_{50}$ value of 2.05 nM. A concentration of 1.5 nM, near the $EC_{50}$ value (within the linear range), was selected as the fixed recombinant hGITR.mmH concentration for the blocking assay.

mAb1 blocked hGITR.mmH binding to hGITR-L in a concentration-dependent manner with 98% maximum inhibition and an $IC_{50}$ value of 6.66 nM. The IgG1 isotype control did not inhibit hGITR.mmH binding to human GITR-L at any of the concentrations tested.

Example 15: Effect of Anti-GITR Antibody on CDC

The ability of mAb1 to mediate CDC against engineered Jurkat T cells expressing human or cynomolgus monkey GITR in the presence of serum complement was evaluated in a cytotoxicity assay. The maximum percent cytotoxicity and $EC_{50}$ values were reported.

CDC assays were performed to assess the ability of mAb1 to induce CDC against T cells expressing human or cynomolgus monkey GITR. Target cells included Jurkat/hCD20/hGITR cells or Jurkat/hCD20/MfGITR cells; Jurkat/hCD20 cells were included as a control target cell line. An IgG1 isotype control was evaluated in parallel with mAb1. An anti-CD20 IgG1 was used as a positive control for inducing CDC against engineered Jurkat T cells in the presence of serum complement factors.

Target cells (5×103 cells/well) were added in triplicate to opaque, white 96-well flat-bottom plates, followed by the addition of mAb1, IgG1 isotype control, or an anti-CD20 IgG1 (final concentrations ranging from 477fM to 500 nM), and then the addition of serum (5% final volume) in assay media (RPMI supplemented with 1% BSA, 100 U/mL penicillin, 100 µg/mL streptomycin, and 292 µg/mL L-glutamine); assay media alone was added in parallel to assess lysis in the absence of complement factors. A buffer control sample that contained all components except the antibody was incorporated into each experiment to determine the background signal of the assay (i.e., nonspecific lysis of target cells).

Plates were incubated at 37° C., 5% CO2 for 3.5 hours. The plates were then equilibrated to room temperature for 30 minutes, followed by the addition of CYTOTOX-GLO™ reagent to the wells for 15 minutes while shaking. The luminescence signal was measured as a readout of cytotoxicity using an ENVISION® plate reader.

The cytotoxic response was calculated as follows:

$$\text{Cytotoxicity (\%)} = \frac{\text{Experimental Signal} - SBS^a_{(target\,cells)}}{\text{Max Signal}_{(target\,cells\,w/digitonin)} - SBS^a_{(target\,cells)}} SBS,$$

spontaneous background signal

Figure 14:
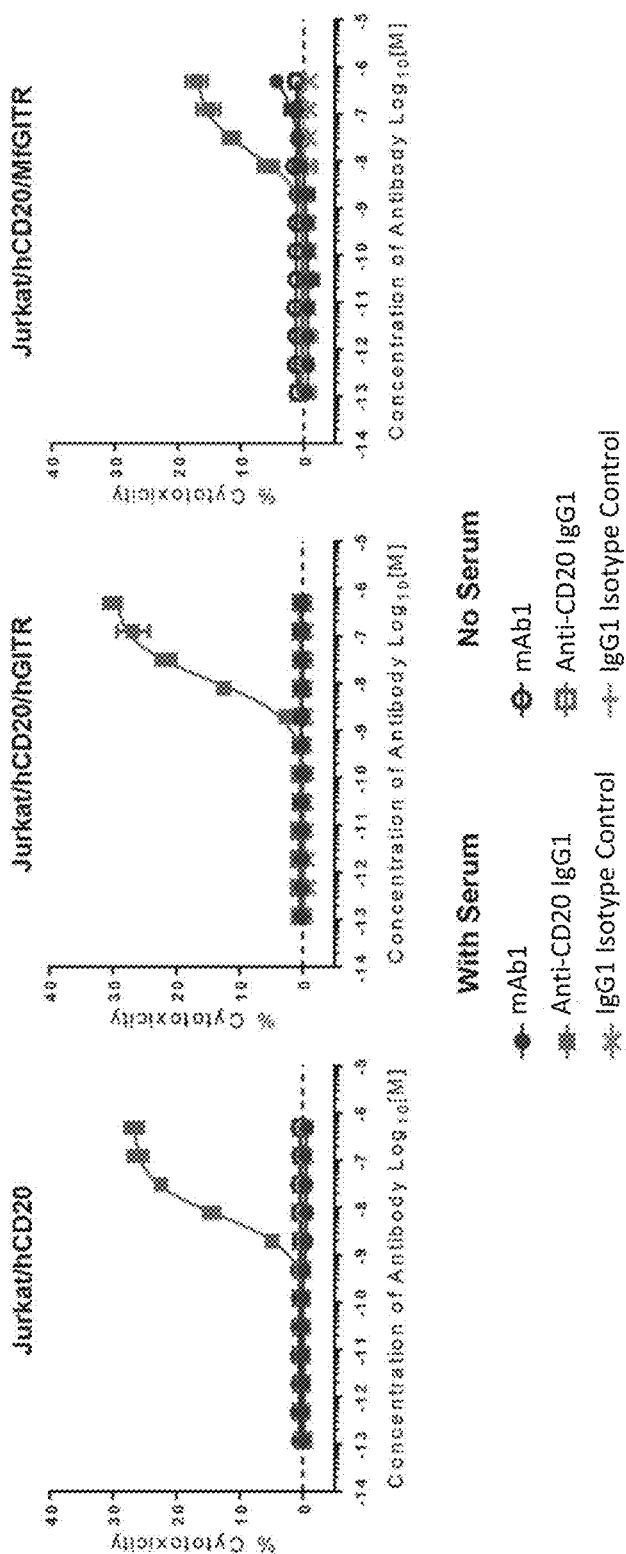
FIG. 14 demonstrates effects of anti-GITR antibody on ADC. Jurkat/hCD20, Jurkat/hCD20/hGITR, or Jurkat/hCD20/MfGITR target cells were incubated with or without 5% NHS and mAb1, an IgG1 isotype control, and an anti-CD20 IgG1 at concentrations ranging from 477fM to 500 nM, including a no antibody control set at 119fM, for 3.5 hours. Cytotoxicity was determined using the commercially available CYTOTOX-GLO™ assay, which is a luminescent cytotoxicity assay that measures the relative number of dead cells in cell populations. The dotted line in each graph denotes the level of nonspecific cytotoxicity observed upon addition of 5% NHS in the absence of antibody. Data from an assay performed in triplicate wells are plotted as mean±SD.

For EC50 determinations, percent cytotoxicity was analyzed using a 4-parameter logistic equation over a 12-point response curve with GRAPHPAD PRISM®.

mAb1 did not mediate CDC against Jurkat/hCD20, Jurkat/hCD20/hGITR, or Jurkat/hCD20/MfGITR target cells at concentrations ranging from 477fM to 500 nM in the presence of 5% NHS. Likewise, CDC was not observed for target cells incubated with the IgG1 isotype control antibody (FIG. 14).

NHS used in the assay was evaluated in the same target cell lines for the ability to induce CDC using the positive control, an anti-CD20 IgG1. In the presence of NHS, the anti-CD20 IgG1 mediated CDC against all 3 target cell lines in a concentration-dependent manner. In the absence of NHS, the anti-CD20 IgG1 did not mediate lysis against any of the tested target cell lines.

Example 16: Ability of Anti-GITR Antibody to Form Immune Complexes Capable of Binding C1q The ability of mAb1 to form immune complexes capable of binding C1q was evaluated using recombinant soluble GITR ectodomain protein in monomeric (hGITR.mmH) or dimeric (hGITR.mFc) form and the MICROVUE™ CIC-C1q EIA kit. As a positive control, binding of heat-aggregated gamma globulin (HAGG) to C1q was also evaluated.

mAb1 or an IgG1 isotype control at 30 nM was incubated with either hGITR.mmH or hGITR.mFc at a 1:1 molar ratio. Controls containing 30 nM mAb1, IgG1 isotype control, hGITR.mmH, or hGITR.mFc alone were also evaluated. Samples were incubated for 30 minutes at 37° C. in 0.1% (w/v) bovine serum albumin (BSA) in DPBS (pH 7.4). Each sample was evaluated in triplicate.

To examine binding of the complexes to C1q, the samples were diluted 50-fold into the kit assay buffer in an ELISA® plate coated with C1q protein and incubated for 60 minutes at room temperature. The wells were washed to remove unbound protein and horseradish peroxidase (HRP)-conjugated goat anti-human IgG (MICROVUE™ CIC-C1q EIA kit) was added to each well to detect C1q-bound immune complexes. After washing away unbound HRP-conjugate, bound complexes were detected by addition of enzyme substrate. Absorbance was read at 405 nm using a PERKINELMER VICTOR™ X5 Multilabel Plate Reader.

A CIC-C1q assay standard, HAGG, was used to generate a linear reference curve based on the absorbance values for 0, 15, and 38 HAGG µg equivalents per mL (µg Eq/mL). The µg Eq/mL concentration for each test sample was determined by reference to this standard curve. High and low HAGG positive controls were also performed. The high HAGG control is expected to result in a range of 11 to 26 µg Eq/mL in the assay, and the low HAGG control is expected to be less than 4 µg Eq/mL. The kit manufacturer defines values less than 4 µg Eq/mL as negative for significant levels of C1q-bound CIC.

Figure 15A:
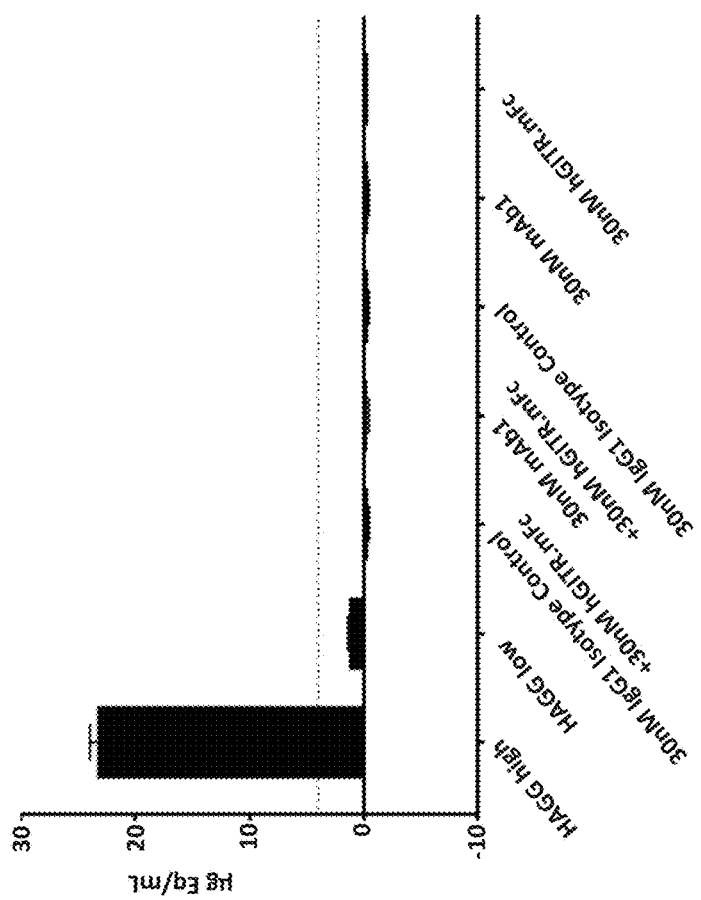
FIG. 15A and FIG. 15B demonstrate that the anti-GITR antibody fails to form immune complexes capable of binding C1q when incubated with soluble GITR. GITR mAb1 or an IgG1 isotype control at 30 nM was incubated with recombinant human GITR ectodomain protein monomer, hGITR.mmH (FIG. 15A), or dimer, hGITR.mFc (FIG. 15B), at a molar ratio of 1:1. Control wells containing antibody, hGITR.mmH, or hGITR.mFc alone were also evaluated. All samples were diluted 50-fold into the kit assay solution prior to analysis. High (38 μg Eq/mL) and low (15 μg Eq/mL) HAGG positive controls were analyzed in parallel and C1q binding of each control sample was observed within the expected range of 11 to 26 μg Eq/mL and less than 4 μg Eq/mL, respectively. The dotted line denotes 4 μg Eq/mL. Data from samples tested in triplicate are plotted as mean±SD.
Figure 15B:
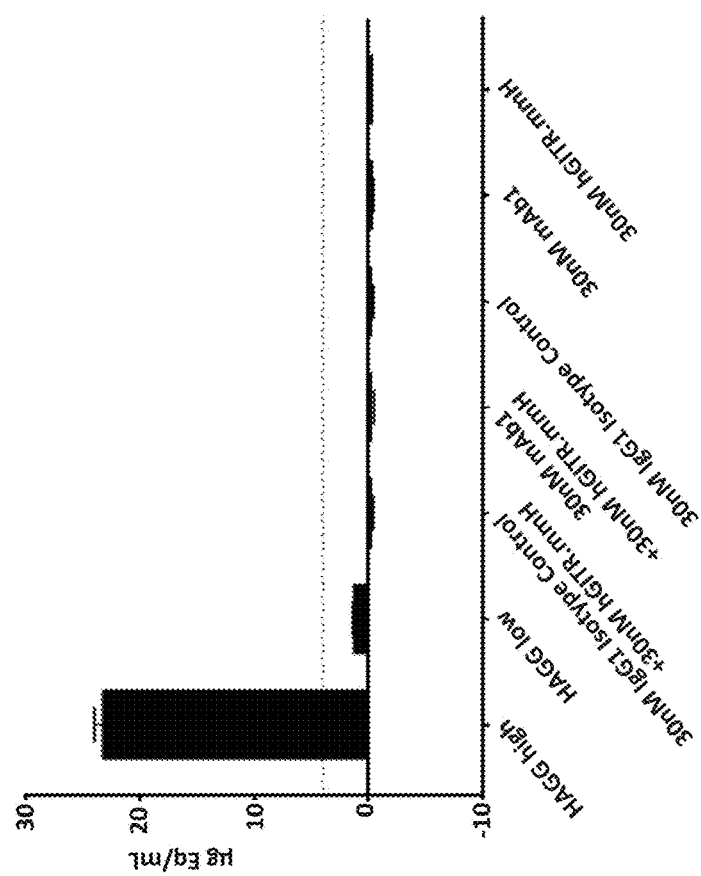

C1q binding was not observed in samples containing mAb1 and either hGITR.mmH or hGITR.mFc (FIG. 15). Likewise, C1q binding was not observed in samples containing the IgG1 isotype control and either hGITR.mmH or hGITR.mFc. No C1q binding was observed in samples containing mAb1, IgG1 isotype control, hGITR.mmH, or hGITR.mFc alone. High and low HAGG positive controls were analyzed in parallel and C1q binding of each sample was observed within the expected respective range.

Example 17: Effect of Anti-GITR Antibody in Combination with Cemiplimab on IL-2 Release from Human Primary T-cells Stimulated with Engineered RBL-2H3 Cells This example examined the agonistic effect of mAb1 on anti-CD3-stimulated IL-2 release from human primary $CD3^+$ T cells from 2 donors. $CD3^+$ T cells were isolated from PBMC from 2 donors. For one donor, PBMC were isolated from peripheral blood using density gradient centrifugation using a FICOLL-PAQUE® PLUS gradient. For the other donor, PBMC were isolated from peripheral blood from a healthy donor using EASYSEP® Direct Human PBMC Isolation Kit from Stem Cell Technologies and following the manufacturer's protocol. Isolated PBMC from both donors were frozen separately in FBS containing 10% DMSO.

For $CD3^+$ T-cell isolation, frozen vials of PBMC were thawed in a 37° C. water bath and diluted in stimulation media (X-VIVO 15 cell culture media supplemented with 10% FBS, HEPES, NaPyr, NEAA, and 0.01 mM BME) containing 50 U/ml benzonase nuclease. Cells were centrifuged at 1200 rpm for 10 minutes, resuspended in EASYSEP® buffer and isolated using StemCell Technologies EASYSEP® T-Cell Isolation kit, following the manufacturer's protocol.

$CD3^+$ T cells were resuspended in stimulation media and plated into 96-well round bottom plates at a concentration of $1\times10^5$ cells/well. RBL-2H3/aCD3 or RBL-2H3/aCD3/hPD-L1 cells were treated with 10 µg/mL of mitomycin C in primary stimulation media at a concentration of $10\times10^6$ cells/mL. After incubation for 1 hour at 37° C., 5% $CO_2$, mitomycin C-treated cells were washed 3 times with D-PBS containing 2% FBS and added to the wells containing T cells at a final concentration of $5\times10^4$ cells/well. Subsequently, antibody combinations of mAb1 or an IgG1 isotype control at final concentrations ranging from 3 pM to 200 nM and cemiplimab or $IgG4^P$ isotype control at a fixed concentration of 20 nM were added to the wells. The final point of the 10-point dilution contained no titrated antibody. Plates were incubated for 3 days at 37° C. with 5% $CO_2$ and subsequently centrifuged to pellet the cells. For IL-2 release, 5 µL of the supernatants were tested using the Human IL-2 Kit from PERKINELMER® according to the manufacturer's protocol. The IL-2 measurements were acquired on PERKINELMER®'s multilabel plate reader ENVISION®. All serial dilutions were tested in triplicate.

The $EC_{50}$ values of the antibodies were determined from a 4-parameter logistic equation over a 10-point dose-response curve using GRAPHPAD PRISM® software. Maximum IL-2 release was determined as the mean maximum response detected within the tested concentration range.

In the absence of PD-L1 on RBL-2H3/aCD3 target cells, mAb1 increased IL-2 release in a dose-dependent manner independent of a fixed concentration of cemiplimab. Both T cell donors exhibited similar $EC_{50}$ and maximum IL-2 values independent of cemiplimab (FIG. 16).

In the presence of PD-L1 on RBL-2H3/aCD3 cells, baseline IL-2 levels were decreased compared to target cells lacking PD-L1 for both T cell donors. However, addition of a fixed concentration of cemiplimab increased baseline IL-2 values. mAb1, independent of cemiplimab led to a dose dependent increase of IL-2 and the addition of cemiplimab further enhanced maximum IL-2 levels, for both T cell donors (FIG. 16).

Results are summarized in Table 21.

TABLE 21

Summary of Effect of mAb1 in Combination with Cemiplimab on IL-2 Release from Anti-CD3-Stimulated Primary T Cells

| | | Donor 555105 CD3+ T Cells | | | | Donor 555130 CD3+ T Cells | | | |
|---|---|---|---|---|---|---|---|---|---|
| | | RBL-2H3/ αCD3 | | RBL-2H3/ αCD3/hPD-L1 | | RBL-2H3/ αCD3 | | RBL-2H3/ αCD3/hPD-L1 | |
| Antibody Combination [a] | | Max IL-2 [b] (pg/ml) | $EC_{50}$ (M) | Max IL-2 [b] (pg/ml) | $EC_{50}$ (M) | Max IL-2 [b] (pg/ml) | $EC_{50}$ (M) | Max IL-2 [b] (pg/ml) | $EC_{50}$ (M) |
| mAb1 | cemiplimab | 33.3 | 1.95E−10 | 36.0 | 1.49E−10 | 170 | 7.30E−11 | 146 | 1.09E−10 |
| | IgG4[P] Isotype Control | 38.2 | 1.19E−10 | 15.5 | 2.00E−10 | 173 | 8.92E−11 | 42.3 | NC |
| IgG1 Isotype Control | cemiplimab | 15.7 | ND | 21.7 | ND | 55.8 | ND | 37.3 | ND |
| | IgG4[P] Isotype Control | 17.4 | ND | 4.62 | ND | 63.8 | ND | 8.85 | ND |

[a] The maximum IL-2 concentration is the highest mean IL-2 concentration value recorded within the tested antibody concentration range (76 fM to 200 nM).
[b] Cemiplimab or the IgG4[P] isotype control were tested at a fixed concentration of 20 nM.
NC, Not calculated because a 4-parameter logistic regression did not converge on a single value;
ND, Not determined because concentration-dependent IL-2 release was not observed Summary The examples above demonstrated that mAb1 is capable of binding to human and cynomolgus monkey GITR expressed on the cell surface of T cells and enhancing Fcγ receptor-mediated NFAT activation in surrogate ADCC reporter assays. Accordingly, mAb1 induced ADCP of engineered T cells and mediated preferential ADCC against Tregs versus CD8+ T cells. On the other hand, mAb1 was not capable of mediating CDC of engineered GITR-expressing T cells or forming immune complexes capable of binding C1q. mAb1 also blocked binding of human GITR to human GITR-L. mAb1, independent of cemiplimab, led to a dose dependent increase of IL-2, and the addition of cemiplimab further enhanced maximum IL-2 levels.

Example 18: Anti-GITR Antibodies Deplete Intratumoral T Regulatory Cells and Increase the CD8+ T-Cell/T-Regulatory Cell Ratio In this experiment, the ability of the parental anti-GITR antibody, CompAb1, and associated variants, mAb1 and mAb2, to deplete T-regulatory cells intratumorally was assessed. Twelve week old female GITR/GITR-L humanized mice were challenged subcutaneously with MC38 mouse colon tumor cells ($3.0 \times 10^5$ cells/mouse). CompAb1, mAb1, or mAb2 were administered on Day 6 via intraperitoneal (i.p.) injection. Mice were euthanized on Day 11 and tumor tissues were collected for FACS analysis. FACS samples were acquired by BD FORTESSA™ X20 and analyzed by FLOWJO® software.

Figure 17:
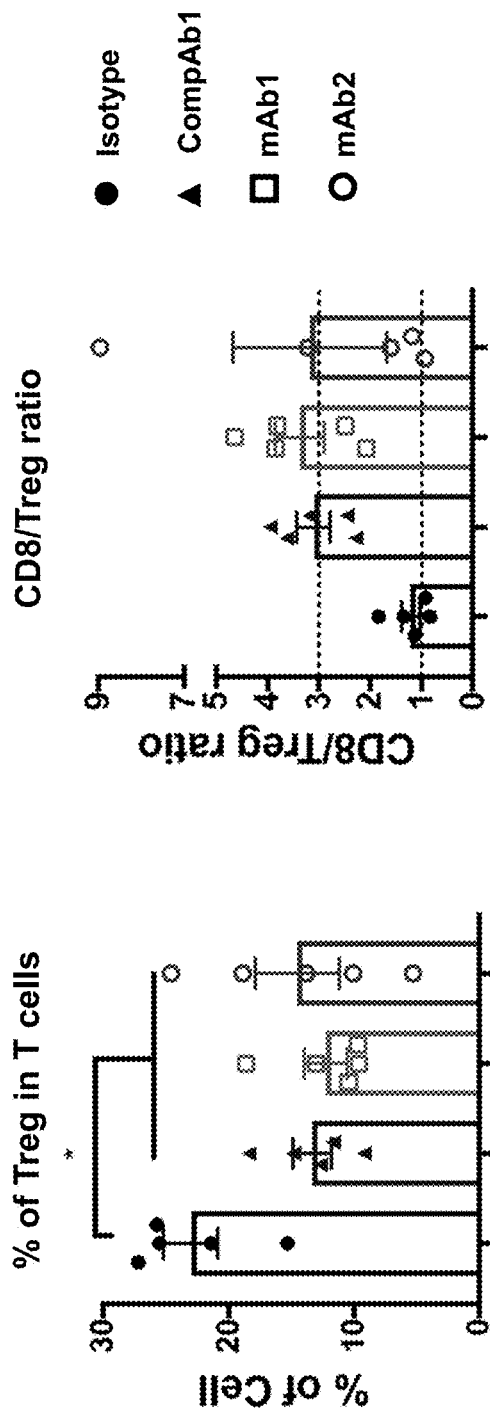
FIG. 17 depicts depletion of intratumoral T regulatory cells and increased CD8+ T-cell/T-regulatory cell ratio by anti-GITR antibodies in GITR/GITR-L humanized mice challenged subcutaneously with MC38 mouse colon tumor cells.

Data are shown in FIG. 17. Overall, single dose antibody treatment with anti-GITR antibodies mediated significant depletion of intratumoral Treg cells and increased the CD8+ T cell/T-reg ratio. CompAb1 and the N101D variant, mAb1, more consistently depleted T-regs and increased the CD8/Treg ratio compared to the N101E variant, mAb2.

Example 19: Anti-Tumor Efficacy of mAb1 in Combination with Cemiplimab in GITR/GITR-L/PD-1-Humanized Mice Bearing Mouse Colorectal Carcinoma Tumors Female GITR/GITR-L/PD-1-humanized mice 9- to 14-weeks old were subcutaneously implanted with MC38 colorectal carcinoma cells ($3 \times 10^5$ cells in 100 μL PBS) in the right flank on day 0. Six days post implantation (on day 6), when the tumors were on average 43 mm³, mice were randomized into 5 groups and administered the first dose of 10 mg/kg IgG1 isotype control+1 mg/kg IgG4P isotype control (n=7), 10 mg/kg IgG1 isotype control+1 mg/kg cemiplimab (n=7), 10 mg/kg mAb1+1 mg/kg cemiplimab (n=7), 1 mg/kg mAb1+1 mg/kg cemiplimab (n=6), or 0.1 mg/kg mAb1+1 mg/kg cemiplimab (n=7). All mice received additional doses on day 13, for a total of 2 doses. Mice were bled on days 7, 12, 14, and 20 to monitor antibody concentrations in serum. Tumor growth was monitored by caliper measurements of tumor volume on days 5, 10, 13, 17, 20, 26, 28, 31, 34, 38, 41, 45, 48, 52, 60, 68, and 75. All mice were monitored until day 75 unless euthanized earlier due to tumor burden.

Figure 18:
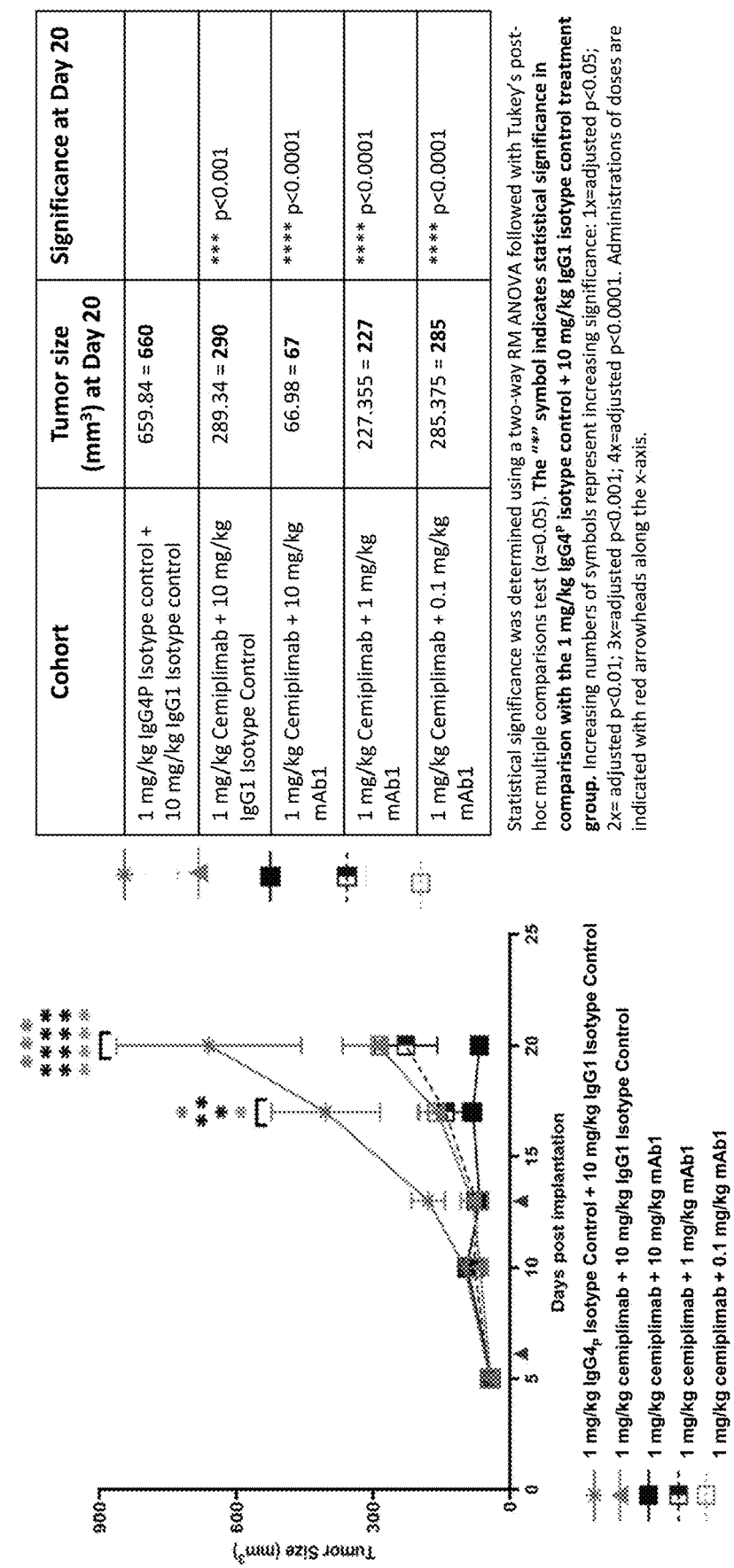
FIG. 18 demonstrates that 1 mg/kg cemiplimab in combination with 10 mg/kg mAb1 results in greater reduction in MC38 tumor growth compared with cemiplimab alone in GITR/GITR-L-PD-1 humanized mice.

A statistically significant reduction in tumor growth was observed for mice dosed with 1 mg/kg cemiplimab in combination with either 0.1, 1, or 10 mg/kg mAb1 compared with mice dosed with the isotype control antibodies (1 mg/kg IgG4[P] isotype control in combination with 10 mg/kg IgG1 isotype control) (FIG. 18). A numerically greater reduction in tumor growth was observed for mice dosed with 1 mg/kg cemiplimab in combination with 10 mg/kg mAb1 (but not 0.1 or 1 mg/kg mAb1) compared with mice dosed with cemiplimab alone (1 mg/kg cemiplimab in combination with 10 mg/kg IgG1 isotype control); however, the difference did not reach statistical significance (adjusted p=0.0525).

Doses of 1 mg/kg cemiplimab alone resulted in tumor clearance in 2 of 7 mice (FIG. 19B). Doses with the addition of mAb1 to cemiplimab resulted in an increased frequency of tumor clearance at the highest tested dose of 10 mg/kg mAb1 (5 of 7 mice; FIG. 19C) but not at the lower doses of 1 and 0.1 mg/kg mAb1 (2 of 6 and 2 of 7 mice, respectively; FIGS. 19 D and E). All mice with tumor clearance remained tumor-free until the end of the study (day 75, approximately 9 weeks after the last dose). As expected, no tumor clearance was observed for mice dosed with isotype control antibodies (FIG. 19A).

Figure 20:
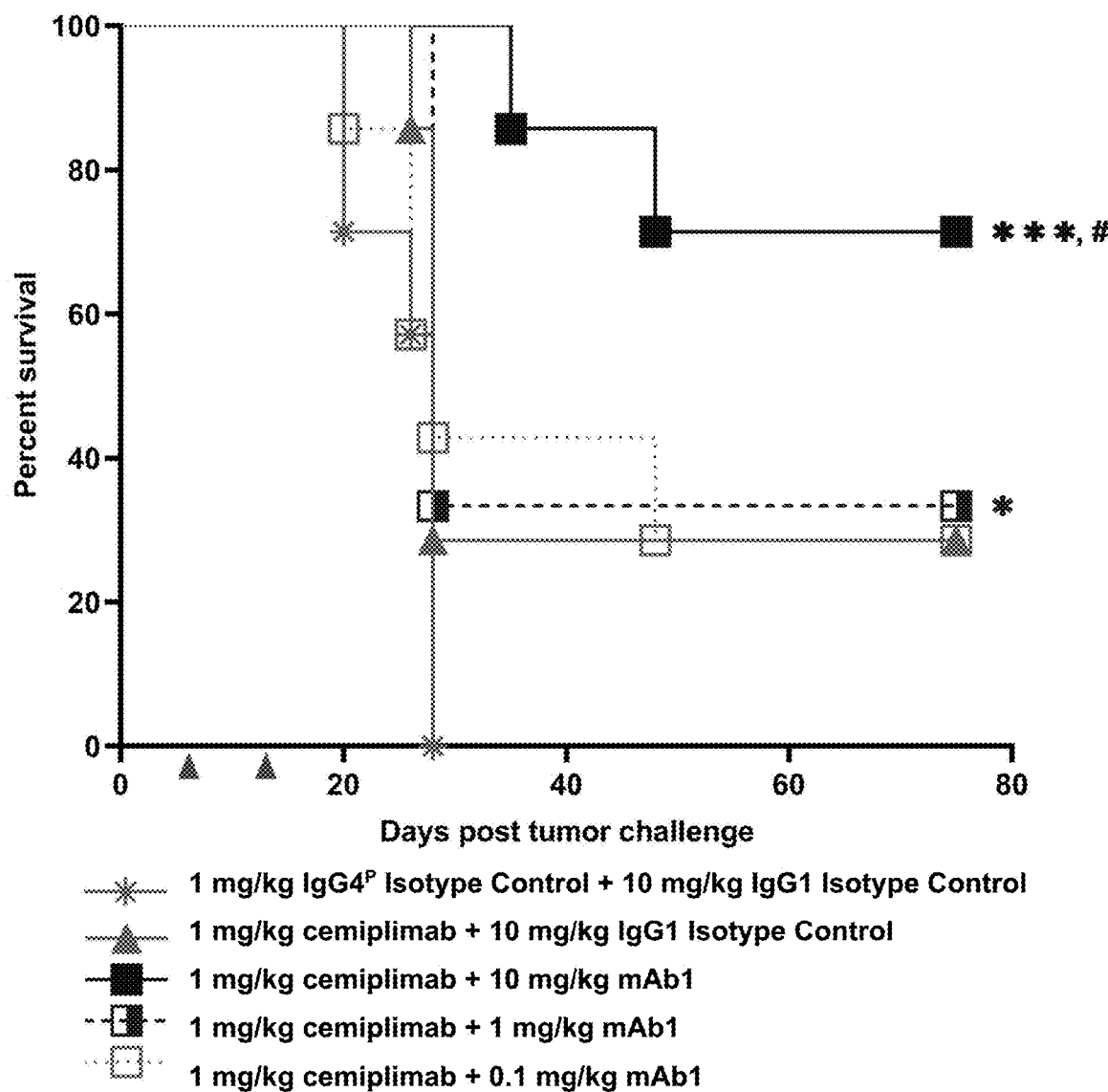
FIG. 20 depicts greater survival in MC38 tumor bearing mice treated with 1 mg/kg cemiplimab in combination with 10 mg/kg mAb1 compared to cemiplimab alone.

Statistically significant differences in survival across groups were detected using an omnibus Gehan-Breslow-Wilcoxon test (p=0.0105); additional Gehan-Breslow-Wilcoxon tests were performed for group-wise comparisons. A significant increase in survival was observed for mice dosed with 1 mg/kg cemiplimab in combination with either 1 or 10 mg/kg mAb1 (33% and 71% survival, respectively) compared with mice dosed with the isotype control antibodies (no survival) (FIG. 20). Furthermore, a significant increase in survival was observed for mice dosed with 1 mg/kg cemiplimab in combination with 10 mg/kg mAb1 (but not 0.1 or 1 mg/kg mAb1) compared with mice dosed with cemiplimab alone (29% survival).

The present disclosure is not to be limited in scope by the specific embodiments described herein. Indeed, various modifications provided herein in addition to those described herein will become apparent to those skilled in the art from the foregoing description and the accompanying figures. Such modifications are intended to fall within the scope of the appended claims.

TABLE 22

Informal Sequence Listing

| SEQ. ID NO. | SEQUENCE | DESCRIPTION |
| --- | --- | --- |
| 1. | caggtgcagc tgcaggagtc gggcccagga ctggtgaagc cttcggagac cctgtccctc acctgcattg tctctggtgg ctccatcagt ggttacttct ggaactggat ccggcagccc ccagggaagg gacttgaatg gattggttat atctattaca gtgggaccac catctacaac ccctccctca agagtcgatt caccatatca ctagacacgt ccaagaacca gttctcccta aagctgacct ctgtgaccgc tgcggacacg gccgtatatt actgtgcgag agagtcgtat aatccctcgc cgcgatattt tgaccactgg ggccagggaa ccctggtcac cgtctcctca | DNA nucleotide sequence |
| 2. | QVQLQESGPG LVKPSETLSL TCIVSGGSIS GYFWNWIRQP PGKGLEWIGY IYYSGTTIYN PSLKSRFTIS LDTSKNQFSL KLTSVTAADT AVYYCARESY NPSPRYFDHW GQGTLVTVSS | AA amino acid sequence |
| 3. | ggtggctcca tcagtggtta cttc | DNA nucleotide sequence |
| 4. | GGSISGYF | AA amino acid sequence |
| 5. | atctattaca gtgggaccac c | DNA nucleotide sequence |
| 6. | IYYSGTT | AA amino acid sequence |
| 7. | gcgagagagt cgtataatcc ctcgccgcga tattttgacc ac | DNA nucleotide sequence |
| 8. | ARESYNPSPR YFDH | AA amino acid sequence |
| 9. | gacatccaga tgacccagtc tccatcctcc ctgtctgcat ctgtaggaga cagagtcacc atcacttgcc gggcaagtca gagcattagc agctatttaa attggtatca gcagaaacca gggaaagccc ctaagctcct gatctatgct gcatccagtt tgcaaagtgg ggtcccgtca aggttcagtg gcagtggatc tgggacagat ttcactctca ccatcagcag tctgcaacct gaagattttg caacttacta ctgtcaacag agttacagta cccctccgat caccttcggc caagggacac gactggagat taaacga | DNA nucleotide sequence |
| 10. | DIQMTQSPSS LSASVGDRVT ITCRASQSIS SYLNWYQQKP GKAPKLLIYA ASSLQSGVPS RFSGSGSGTD FTLTISSLQP EDFATYYCQQ SYSTPPITFG QGTRLEIKR | AA amino acid sequence |
| 11. | cagagcatta gcagctat | DNA nucleotide sequence |
| 12. | QSISSY | AA amino acid sequence |

TABLE 22-continued

Informal Sequence Listing

| SEQ. ID NO. | SEQUENCE | DESCRIPTION |
|---|---|---|
| 13. | gctgcatcc | DNA nucleotide sequence |
| 14. | AAS | AA amino acid sequence |
| 15. | caacagagtt acagtacccc tccgatcacc | DNA nucleotide sequence |
| 16. | QQSYSTPPIT | AA amino acid sequence |
| 17. | caggtgcagctgcaggagtcgggcccaggactggtgaagccttcggagaccctgtccctcacctgcattg tctctggtggctccatcagtggttacttctggaactggatccggcagcccccagggaagggacttgaatg gattggttatatctattacagtgggaccaccatctacaaccctccctcaagagtcgattcaccatatca ctagacacgtccaagaaccagttctccctaaagctgacctctgtgaccgctgcggacacggccgtatatt actgtgcgagagagtcgtataatccctcgccgcgatattttgaccactggggccagggaaccctggtcac cgtctcctcagcctccaccaagggcccatcggtcttccccctggcaccctcctccaagagcacctctggg ggcacagcggccctgggctgcctggtcaaggactacttccccgaaccggtgacggtgtcgtggaactcag gcgccctgaccagcggcgtgcacaccttcccggctgtcctacagtcctcaggactctactccctcagcag cgtggtgaccgtgccctccagcagcttgggcacccagacctacatctgcaacgtgaatcacaagcccagc aacaccaaggtggacaagaaagttgagcccaaatcttgtgacaaaactcacacatgcccaccgtgcccag cacctgaactcctggggggaccgtcagtcttcctcttccccccaaaacccaaggacaccctcatgatctc ccggacccctgaggtcacatgcgtggtggtggacgtgagccacgaagaccctgaggtcaagttcaactgg tacgtggacggcgtggaggtgcataatgccaagacaaagccgcgggaggagcagtacaacagcacgtacc gtgtggtcagcgtcctcaccgtcctgcaccaggactggctgaatggcaaggagtacaagtgcaaggtctc caacaaagccctcccagcccccatcgagaaaaccatctccaaagccaaagggcagccccgagaaccacag gtgtacaccctgcccccatcccgggatgagctgaccaagaaccaggtcagcctgacctgcctggtcaaag gcttctatcccagcgacatcgccgtggagtgggagagcaatgggcagccggagaacaactacaagaccac gcctcccgtgctggactccgacggctccttcttcctctacagcaagctcaccgtggacaagagcaggtgg cagcaggggaacgtcttctcatgctccgtgatgcatgaggctctgcacaaccactacacgcagaagtccc tctccctgtctccgggtaaatga | DNA nucleotide sequence |
| 18. | QVQLQESGPG LVKPSETLSL TCIVSGGSIS GYFWNWIRQP PGKGLEWIGY IYYSGTTIYN PSLKSRFTIS LDTSKNQFSL KLTSVTAADT AVYYCARESY NPSPRYFDHW GQGTLVTVSS ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPELLGG PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSRDE LTKNQVSLTC LVKGFYPSDI AVEWESNGQP ENNYKTTPPV LDSDGSFFLY SKLTVDKSRW QQGNVFSCSV MHEALHNHYT QKSLSLSPGK | AA amino acid sequence |
| 19. | gacatccaga tgacccagtc tccatcctcc ctgtctgcat ctgtaggaga cagagtcacc atcacttgcc gggcaagtca gagcattage agctatttaa attggtatca gcagaaacca gggaaagccc ctaagctcct gatctatgct gcatccagtt tgcaaagtgg ggtcccgtca aggttcagtg gcagtggatc tgggacagat tcactctcac ccatcagcag tctgcaacct gaagattttg caacttacta ctgtcaacag agttacagta ccccteccgat cacettcggc caagggacac gactggagat taaacgaact gtggctgcac catctgtctt catcttccca ccatctgatg agcagttgaa atctggaact gcctctgttg tgtgcctgct gaataacttc tatcccagag aggccaaagt acagtggaag gtggataacg cccteccaatc gggtaactcc caggagagtg tcacagagca ggacagcaag gacagcacct acagcctcag cagcaccctg acgctgagca aagcagacta cgagaaacac aaagtctacg cctgcgaagt cacccatcag ggcctgagct cgcccgtcac aaagagcttc aacaggggag agtgttag | DNA nucleotide sequence |
| 20. | DIQMTQSPSS LSASVGDRVT ITCRASQSIS SYLNWYQQKP GKAPKLLIYA ASSLQSGVPS RFSGSGSGTD FTLTISSLQP EDFATYYCQQ SYSTPPITFG QGTRLEIKRT VAAPSVFIFP PSDEQLKSGT ASVVCLLNNF YPREAKVQWK VDNALQSGNS QESVTEQDSK DSTYSLSSTL TLSKADYEKH KVYACEVTHQ GLSSPVTKSF NRGEC | AA amino acid sequence |
| 21. | caggtgcagc tgcaggagtc gggcccagga ctggtgaagc cttcggagac cctgtccctc acctgcattg tctctggtgg ctccatcagt ggttacttct ggaactggat ccggcagccc ccagggaagg gacttgaatg gattggttat atctattaca gtgggaccac catctacaac cctccctca agagtcgatt caccatatca ctagacacgt ccaagaacca gttctcccta aagctgacct ctgtgaccgc tgcggacacg gccgtatatt actgtgcgag agagtcgtat gacccctccc cgcgatattt tgaccactgg ggccagggaa ccctggtcac cgtctcctca | DNA nucleotide sequence |
| 22. | QVQLQESGPG LVKPSETLSL TCIVSGGSIS GYFWNWIRQP PGKGLEWIGY IYYSGTTIYN PSLKSRFTIS LDTSKNQFSL KLTSVTAADT AVYYCARESY DPSPRYFDHW GQGTLVTVSS | AA amino acid sequence |
| 23. | gcgagagagt cgtatgaccc ctccccgcga tattttgacc ac | DNA nucleotide sequence |

TABLE 22-continued

Informal Sequence Listing

| SEQ. ID NO. | SEQUENCE | DESCRIPTION |
|---|---|---|
| 24. | ARESYDPSPR YFDH | AA amino acid sequence |
| 25. | caggtgcagctgcaggagtcgggcccaggactggtgaagccttcggagaccctgtccctcacctgcattg<br>tctctggtggctccatcagtggttacttctggaactggatccggcagccccagggaagggacttgaatg<br>gattggttatatctattacagtgggaccaccatctacaaccctccctcaagagtcgattcaccatatca<br>ctagacacgtccaagaaccagttctccctaaagctgacctctgtgaccgctgcggacacggccgtatatt<br>actgtgcgagagagtcgtatgaccccctccccgcgatattttgaccactggggccagggaaccctggtcac<br>cgtctcctcagcctccaccaagggcccatcggtcttccccctggcaccctcctccaagagcacctctggg<br>ggcacagcggccctgggctgcctggtcaaggactacttccccgaaccggtgacggtgtcgtggaactcag<br>gcgccctgaccagcggcgtgcacaccttcccggctgtcctacagtcctcaggactctactccctcagcag<br>cgtggtgaccgtgccctccagcagcttgggcacccagacctacatctgcaacgtgaatcacaagcccagc<br>aacaccaaggtggacaagaaagttgagcccaaatcttgtgacaaaactcacacatgcccaccgtgcccag<br>cacctgaactcctggggggaccgtcagtcttcctcttccccccaaaacccaaggacaccctcatgatctc<br>ccggacccctgaggtcacatgcgtggtggtggacgtgagccacgaagaccctgaggtcaagttcaactgg<br>tacgtggacggcgtggaggtgcataatgccaagacaaagccgcgggaggagcagtacaacagcacgtacc<br>gtgtggtcagcgtcctcaccgtcctgcaccaggactggctgaatggcaaggagtacaagtgcaaggtctc<br>caacaaagccctcccagcccccatcgagaaaaccatctccaaagccaaagggcagccccgagaaccacag<br>gtgtacaccctgcccccatcccgggatgagctgaccaagaaccaggtcagcctgacctgcctggtcaaag<br>gcttctatcccagcgacatcgccgtggagtgggagagcaatgggcagccggagaacaactacaagaccac<br>gcctcccgtgctggactccgacggctccttcttcctctacagcaagctcaccgtggacaagagcaggtgg<br>cagcaggggaacgtcttctcatgctccgtgatgcatgaggctctgcacaaccactacacgcagaagtccc<br>tctccctgtctccgggtaaatga | DNA nucleotide sequence |
| 26. | QVQLQESGPG LVKPSETLSL TCIVSGGSIS GYFWNWIRQP PGKGLEWIGY IYYSGTTIYN<br>PSLKSRFTIS LDTSKNQFSL KLTSVTAADT AVYYCARESY DPSPRYFDHW GQGTLVTVSS<br>ASTKGPSVFP LAPSSKSTSG GTAALGCLVK DYFPEPVTVS WNSGALTSGV HTFPAVLQSS<br>GLYSLSSVVT VPSSSLGTQT YICNVNHKPS NTKVDKKVEP KSCDKTHTCP PCPAPELLGG<br>PSVFLFPPKP KDTLMISRTP EVTCVVVDVS HEDPEVKFNW YVDGVEVHNA KTKPREEQYN<br>STYRVVSVLT VLHQDWLNGK EYKCKVSNKA LPAPIEKTIS KAKGQPREPQ VYTLPPSRDE<br>LTKNQVSLTC LVKGFYPSDI AVEWESNGQP ENNYKTTPPV LDSDGSFFLY SKLTVDKSRW<br>QQGNVFSCSV MHEALHNHYT QKSLSLSPGK | AA amino acid sequence |
| 27. | caggtgcagc tgcaggagtc gggcccagga ctggtgaagc cttcggagac cctgtccctc<br>acctgcattg tctctggtgg ctccatcagt ggttacttct ggaactggat ccggcagccc<br>ccagggaagg gacttgaatg gattggttat atctattaca gtgggaccac catctacaac<br>cctccctca agagtcgatt caccatatca ctagacacgt ccaagaacca gttctcccta<br>aagctgacct ctgtgaccgc tgcggacacg gccgtatatt actgtgcgag agagtcgtat<br>gagcccctcc cgcgatattt tgaccactgg ggccaggaa ccctggtcac cgtctcctca | DNA nucleotide sequence |
| 28. | QVQLQESGPG LVKPSETLSL TCIVSGGSIS GYFWNWIRQP PGKGLEWIGY IYYSGTTIYN<br>PSLKSRFTIS LDTSKNQFSL KLTSVTAADT AVYYCARESY EPSPRYFDHW GQGTLVTVSS | AA amino acid sequence |
| 29. | gcgagagagt cgtatgagcc ctccccgcga tattttgacc ac | DNA nucleotide sequence |
| 30. | ARESYEPSPR YFDH | AA amino acid sequence |
| 31. | caggtgcagctgcaggagtcgggcccaggactggtgaagccttcggagaccctgtccctcacctgcattg<br>tctctggtggctccatcagtggttacttctggaactggatccggcagccccagggaagggacttgaatg<br>gattggttatatctattacagtgggaccaccatctacaaccctccctcaagagtcgattcaccatatca<br>ctagacacgtccaagaaccagttctccctaaagctgacctctgtgaccgctgcggacacggccgtatatt<br>actgtgcgagagagtcgtatgagcccctccccgcgatattttgaccactggggccagggaaccctggtcac<br>cgtctcctcagcctccaccaagggcccatcggtcttccccctggcaccctcctccaagagcacctctggg<br>ggcacagcggccctgggctgcctggtcaaggactacttccccgaaccggtgacggtgtcgtggaactcag<br>gcgccctgaccagcggcgtgcacaccttcccggctgtcctacagtcctcaggactctactccctcagcag<br>cgtggtgaccgtgccctccagcagcttgggcacccagacctacatctgcaacgtgaatcacaagcccagc<br>aacaccaaggtggacaagaaagttgagcccaaatcttgtgacaaaactcacacatgcccaccgtgcccag<br>cacctgaactcctggggggaccgtcagtcttcctcttccccccaaaacccaaggacaccctcatgatctc<br>ccggacccctgaggtcacatgcgtggtggtggacgtgagccacgaagaccctgaggtcaagttcaactgg<br>tacgtggacggcgtggaggtgcataatgccaagacaaagccgcgggaggagcagtacaacagcacgtacc<br>gtgtggtcagcgtcctcaccgtcctgcaccaggactggctgaatggcaaggagtacaagtgcaaggtctc<br>caacaaagccctcccagcccccatcgagaaaaccatctccaaagccaaagggcagccccgagaaccacag<br>gtgtacaccctgcccccatcccgggatgagctgaccaagaaccaggtcagcctgacctgcctggtcaaag<br>gcttctatcccagcgacatcgccgtggagtgggagagcaatgggcagccggagaacaactacaagaccac<br>gcctcccgtgctggactccgacggctccttcttcctctacagcaagctcaccgtggacaagagcaggtgg<br>cagcaggggaacgtcttctcatgctccgtgatgcatgaggctctgcacaaccactacacgcagaagtccc<br>tctccctgtctccgggtaaatga | DNA nucleotide sequence |
| 32. | QVQLQESGPG LVKPSETLSL TCIVSGGSIS GYFWNWIRQP PGKGLEWIGY IYYSGTTIYN<br>PSLKSRFTIS LDTSKNQFSL KLTSVTAADT AVYYCARESY EPSPRYFDHW GQGTLVTVSS<br>ASTKGPSVFP LAPSSKSTSG GTAALGCLVK DYFPEPVTVS WNSGALTSGV HTFPAVLQSS<br>GLYSLSSVVT VPSSSLGTQT YICNVNHKPS NTKVDKKVEP KSCDKTHTCP PCPAPELLGG | AA amino acid sequence |

TABLE 22-continued

Informal Sequence Listing

| SEQ. ID NO. | SEQUENCE | DESCRIPTION |
|---|---|---|
| | PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSRDE LTKNQVSLTC LVKGFYPSDI AVEWESNGQP ENNYKTTPPV LDSDGSFFLY SKLTVDKSRW QQGNVFSCSV MHEALHNHYT QKSLSLSPGK | |
| 33. | caggtgcagc tgcaggagtc gggcccagga ctggtgaagc cttcggagac cctgtccctc acctgcattg tctctggtgg ctccatcagt ggttacttct ggaactggat ccggcagccc ccagggaagg gacttgaatg gattggttat atctattaca gtgggaccac catctacaac ccctccctca agagtcgatt caccatatca ctagacacgt ccaagaacca gttctcccta aagctgacct ctgtgaccgc tgcggacacg gccgtatatt actgtgcgag agagtcgtat tcccccctccc cgcgatattt tgaccactgg ggcagggaa ccctggtcac cgtctcctca | DNA nucleotide sequence |
| 34. | QVQLQESGPG LVKPSETLSL TCIVSGGSIS GYFWNWIRQP PGKGLEWIGY IYYSGTTIYN PSLKSRFTIS LDTSKNQFSL KLTSVTAADT AVYYCARESY SPSPRYFDHW GQGTLVTVSS | AA amino acid sequence |
| 35. | gcgagagagt cgtattcccc ctccccgcga tattttgacc ac | DNA nucleotide sequence |
| 36. | ARESYSPSPR YFDH | AA amino acid sequence |
| 37. | caggtgcagctgcaggagtcgggcccaggactggtgaagccttcggagaccctgtccctcacctgcattg tctctggtggctccatcagtggttacttctggaactggatccggcagcccccagggaagggacttgaatg gattggttatatctattacagtgggaccaccatctacaaccctccctcaagagtcgattcaccatatca ctagacacgtccaagaaccagttctcccctaaagctgacctctgtgaccgctgcggacacggccgtatatt actgtgcgagagagtcgtattccccctccccgcgatattttgaccactggggccagggaaccctggtcac cgtctcctcagcctccaccaagggcccatcggtcttccccctggcaccctcctccaagagcacctctggg ggcacagcggccctgggctgcctggtcaaggactacttccccgaaccggtgacggtgtcgtggaactcag gcgccctgaccagcggcgtgcacaccttcccggctgtcctacagtcctcaggactctactccctcagcag cgtggtgaccgtgccctcagcagcttgggcacccagacctacatctgcaacgtgaatcacaagcccagc aacaccaaggtggacaagaaagttgagcccaaatcttgtgacaaaactcacacatgcccaccgtgccag cacctgaactcctggggggaccgtcagtcttcctcttccccccaaaacccaaggacaccctcatgatctc ccggacccctgaggtcacatgcgtggtggtggacgtgagccacgaagaccctgaggtcaagttcaactgg tacgtggacggcgtggaggtgcataatgccaagacaaaaccgcgggaggagcagtacaacagcacgtacc gtgtggtcagcgtcctcaccgtcctgcaccaggactggctgaatggcaaggagtacaagtgcaaggtctc caacaaagccctcccagcccccatcgagaaaaccatctccaaagccaaagggcagccccgagaaccacag gtgtacaccctgcccccatcccgggatgagctgaccaagaaccaggtcagcctgacctgcctggtcaaag gcttctatcccagcgacatcgccgtggagtgggagagcaatgggcagccggagaacaactacaagaccac gcctcccgtgctggactccgacggctccttcttcctctacagcaagctcaccgtggacaagagcaggtgg cagcaggggaacgtcttctcatgctccgtgatgcatgaggctctgcacaaccactacacgcagaagtccc tctccctgtctccgggtaaatga | DNA nucleotide sequence |
| 38. | QVQLQESGPG LVKPSETLSL TCIVSGGSIS GYFWNWIRQP PGKGLEWIGY IYYSGTTIYN PSLKSRFTIS LDTSKNQFSL KLTSVTAADT AVYYCARESY SPSPRYFDHW GQGTLVTVSS ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPELLGG PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSRDE LTKNQVSLTC LVKGFYPSDI AVEWESNGQP ENNYKTTPPV LDSDGSFFLY SKLTVDKSRW QQGNVFSCSV MHEALHNHYT QKSLSLSPGK | AA amino acid sequence |
| 39. | caggtgcagc tgcaggagtc gggcccagga ctggtgaagc cttcggagac cctgtccctc acctgcattg tctctggtgg ctccatcagt ggttacttct ggaactggat ccggcagccc ccagggaagg gacttgaatg gattggttat atctattaca gtgggaccac catctacaac ccctccctca agagtcgatt caccatatca ctagacacgt ccaagaacca gttctcccta aagctgacct ctgtgaccgc tgcggacacg gccgtatatt actgtgcgag agagtcgtat accccctccc cgcgatattt tgaccactgg ggcagggaa ccctggtcac cgtctcctca | DNA nucleotide sequence |
| 40. | QVQLQESGPG LVKPSETLSL TCIVSGGSIS GYFWNWIRQP PGKGLEWIGY IYYSGTTIYN PSLKSRFTIS LDTSKNQFSL KLTSVTAADT AVYYCARESY TPSPRYFDHW GQGTLVTVSS | AA amino acid sequence |
| 41. | gcgagagagt cgtataccc ctccccgcga tattttgacc ac | DNA nucleotide sequence |
| 42. | ARESYTPSPR YFDH | AA amino acid sequence |
| 43. | caggtgcagctgcaggagtcgggcccaggactggtgaagccttcggagaccctgtccctcacctgcattg tctctggtggctccatcagtggttacttctggaactggatccggcagcccccagggaagggacttgaatg gattggttatatctattacagtgggaccaccatctacaaccctccctcaagagtcgattcaccatatca ctagacacgtccaagaaccagttctcccctaaagctgacctctgtgaccgctgcggacacggccgtatatt actgtgcgagagagtcgtataccccctccccgcgatattttgaccactggggccagggaaccctggtcac cgtctcctcagcctccaccaagggcccatcggtcttccccctggcaccctcctccaagagcacctctggg | DNA nucleotide sequence |

TABLE 22-continued

Informal Sequence Listing

| SEQ. ID NO. | SEQUENCE | DESCRIPTION |
|---|---|---|
|  | ggcacagcggccctgggctgcctggtcaaggactacttccccgaaccggtgacggtgtcgtggaactcag<br>gcgccctgaccagcggcgtgcacaccttcccggctgtcctacagtcctcaggactctactccctcagcag<br>cgtggtgaccgtgccctccagcagcttgggcacccagacctacatctgcaacgtgaatcacaagcccagc<br>aacaccaaggtggacaagaaagttgagcccaaatcttgtgacaaaactcacacatgcccaccgtgccccag<br>cacctgaactcctgggggaccgtcagtcttcctcttccccccaaaacccaaggacaccctcatgatctc<br>ccggacccctgaggtcacatgcgtggtggtggacgtgagccacgaagaccctgaggtcaagttcaactgg<br>tacgtggacggcgtggaggtgcataatgccaagacaaagccgcgggaggagcagtacaacagcacgtacc<br>gtgtggtcagcgtcctcaccgtcctgcaccaggactggctgaatggcaaggagtacaagtgcaaggtctc<br>caacaaagccctcccagcccccatcgagaaaaccatctccaaagccaaagggcagccccgagaaccacag<br>gtgtacaccctgccccatcccgggatgagctgaccaagaaccaggtcagcctgacctgcctggtcaaag<br>gcttctatcccagcgacatcgccgtggagtgggagagcaatgggcagccggagaacaactacaagaccac<br>gcctcccgtgctggactccgacggctccttcttcctctacagcaagctcaccgtggacaagagcaggtgg<br>cagcaggggaacgtcttctcatgctccgtgatgcatgaggctctgcacaaccactacacgcagaagtccc<br>tctccctgtctccgggtaaatga |  |
| 44. | QVQLQESGPG LVKPSETLSL TCIVSGGSIS GYFWNWIRQP PKKGLEWIGY IYYSGTTIYN<br>PSLKSRFTIS LDTSKNQFSL KLTSVTAADT AVYYCARESY TPSPRYFDHW GQGTLVTVSS<br>ASTKGPSVFP LAPSSKSTSG GTAALGCLVK DYFPEPVTVS WNSGALTSGV HTFPAVLQSS<br>GLYSLSSVVT VPSSSLGTQT YICNVNHKPS NTKVDKKVEP KSCDKTHTCP PCPAPELLGG<br>PSVFLFPPKP KDTLMISRTP EVTCVVVDVS HEDPEVKFNW YVDGVEVHNA KTKPREEQYN<br>STYRVVSVLT VLHQDWLNGK EYKCKVSNKA LPAPIEKTIS KAKGQPREPQ VYTLPPSRDE<br>LTKNQVSLTC LVKGFYPSDI AVEWESNGQP ENNYKTTPPV LDSDGSFFLY SKLTVDKSRW<br>QQGNVFSCSV MHEALHNHYT QKSLSLSPGK | AA amino acid sequence |
| 45. | MHRPRRRGTR PPPLALLAAL LLAARGADAQ RPTGGPGCGP GRLLLGTGTD ARCCRVHTTR<br>CCRDYPGEEC CSEWDCMCVQ PEFHCGDPCC TTCRHHPCPP GQGVQSQGKF AFGFQCIDCA<br>SGTFSGGHEG HCKPWTDCTQ FGFLTVFPGN KTHNAVCVPG SPPAEPEQKL ISEEDLGGEQ<br>KLISEEDLHH HHHH | AA amino acid sequence |
| 46. | MHRPRRRGTR PPPLALLAAL LLAARGADAQ RPTGGPGCGP GRLLLGTGTD ARCCRVHTTR<br>CCRDYPGEEC CSEWDCMCVQ PEFHCGDPCC TTCRHHPCPP GQGVQSQGKF SFGFQCIDCA<br>SGTFSGGHEG HCKPWTDCTQ FGFLTVFPGN KTHNAVCVPG SPPAEPEPRG PTIKPCPPPCK<br>CPAPNLLGGP SVFIFPPKIK SVLMISLSPI VTCVVVDVSE DDPDVQISWF VNNVEVHTAQ<br>TQTHREDYNS TLRVVSALPI QHQDWNSGKE FKCKVNNKDL PAPIERTISK PKGSVRAPQV<br>YVLPPPEEEM TKKQVTLTCM VTDFMPEDIY VEWTNNGKTE LNYKNTEPVL DSDGSYFMYS<br>KLRVEKKNWV ERNSYSCSVV HEGLHNHHTT KSFSRTPGK | AA amino acid sequence |
| 47. | MHRPRRRGTR PPPLALLAAL LLAARGADAQ RPTGGPGCGP GRLLLGTGTD ARCCRVHTTR<br>CCRDYPGEEC CSEWDCMCVQ PEFHCGDPCC TTCRHHPCPP GQGVQSQGKF SFGFQCIDCA<br>SGTFSGGHEG HCKPWTDCTQ FGFLTVFPGN KTHVANCVPG SPPAEPDKTH TCPPCPAPEL<br>LGGPSVFVFP PKPKDTLMIS RTPEVTCVVV DVSHEDPEVK FNWYVDGVEV HNAKTKRPEE<br>QYNSTYRVVS VLTVLHQDWL NGKEYKCKVS NKALPAPIEK TISKAKGQPR EPQVYTLPPS<br>RDELTKNQVS LTCLVKGFYP SDIAVEWESN GQPENNYKTT PPVLDSDGSF FLYSKLTVDK<br>SRWQQGNVFS CSVMHEALHN HYTQKSLSLS PGK | AA amino acid sequence |
| 48. | MHRPRRRGTR PPPLALLAAL LLAARGADAQ RPTGGPGCGP GRLLLGTGKD ARCCRVHPTR<br>CCRDYQGEEC CSEWDCVCVQ PEFHCGNPCC TTCQHHPCPS GQGVQPQGKF SFGFRCVDCA<br>LGTFSRGHDG HCKPWTDCTQ FGFLTVFPGN KTHNAVCVPG SPPAEPEQKL ISEEDLGGEQ<br>KLISEEDLHH HHHH | AA amino acid sequence |
| 49. | MAQHGAMGAF RALCGLALLC ALSLGQRPTG GPGCGPGRLL LGTGTDARCC RVHTTRCCRD<br>YPGEECCSEW DCMCVQPEFH CGDPCCTTCR HHPCPPGQGV QSQGKFSFGF QCIDCASGTF<br>SGGHEGHCKP WTDCTQFGFL TVFPGNKTHN AVCVPGSPPA EPLGWLTVVL LAVAACVLLL<br>TSAQLGLHIS QLRSQCMWPR ETQLLLEVPP STEDARSCQF PEEERGERSA EEKGRLGDLW<br>V | AA amino acid sequence |

SEQUENCE LISTING

```
Sequence total quantity: 49
SEQ ID NO: 1           moltype = DNA  length = 360
FEATURE                Location/Qualifiers
misc_feature           1..360
                       note = Synthetic
source                 1..360
                       mol_type = other DNA
                       organism = synthetic construct
SEQUENCE: 1
caggtgcagc tgcaggagtc gggcccagga ctggtgaagc cttcggagac cctgtccctc    60
acctgcattg tctctggtgg ctccatcagt ggttacttct ggaactggat ccggcagccc   120
```

```
ccagggaagg gacttgaatg gattggttat atctattaca gtgggaccac catctacaac    180
ccctccctca agagtcgatt caccatatca ctagacacgt ccaagaacca gttctcccta    240
aagctgacct ctgtgaccgc tgcggacacg gccgtatatt actgtgcgag agagtcgtat    300
aatccctcgc cgcgatattt tgaccactgg ggccagggaa ccctggtcac cgtctcctca    360

SEQ ID NO: 2               moltype = AA   length = 120
FEATURE                    Location/Qualifiers
REGION                     1..120
                           note = Synthetic
source                     1..120
                           mol_type = protein
                           organism = synthetic construct
SEQUENCE: 2
QVQLQESGPG LVKPSETLSL TCIVSGGSIS GYFWNWIRQP PGKGLEWIGY IYYSGTTIYN     60
PSLKSRFTIS LDTSKNQFSL KLTSVTAADT AVYYCARESY NPSPRYFDHW GQGTLVTVSS    120

SEQ ID NO: 3               moltype = DNA   length = 24
FEATURE                    Location/Qualifiers
misc_feature               1..24
                           note = Synthetic
source                     1..24
                           mol_type = other DNA
                           organism = synthetic construct
SEQUENCE: 3
ggtggctcca tcagtggtta cttc                                            24

SEQ ID NO: 4               moltype = AA   length = 8
FEATURE                    Location/Qualifiers
REGION                     1..8
                           note = Synthetic
source                     1..8
                           mol_type = protein
                           organism = synthetic construct
SEQUENCE: 4
GGSISGYF                                                               8

SEQ ID NO: 5               moltype = DNA   length = 21
FEATURE                    Location/Qualifiers
misc_feature               1..21
                           note = Synthetic
source                     1..21
                           mol_type = other DNA
                           organism = synthetic construct
SEQUENCE: 5
atctattaca gtgggaccac c                                               21

SEQ ID NO: 6               moltype = AA   length = 7
FEATURE                    Location/Qualifiers
REGION                     1..7
                           note = Synthetic
source                     1..7
                           mol_type = protein
                           organism = synthetic construct
SEQUENCE: 6
IYYSGTT                                                                7

SEQ ID NO: 7               moltype = DNA   length = 42
FEATURE                    Location/Qualifiers
misc_feature               1..42
                           note = Synthetic
source                     1..42
                           mol_type = other DNA
                           organism = synthetic construct
SEQUENCE: 7
gcgagagagt cgtataatcc ctcgccgcga tattttgacc ac                        42

SEQ ID NO: 8               moltype = AA   length = 14
FEATURE                    Location/Qualifiers
REGION                     1..14
                           note = Synthetic
source                     1..14
                           mol_type = protein
                           organism = synthetic construct
SEQUENCE: 8
ARESYNPSPR YFDH                                                       14

SEQ ID NO: 9               moltype = DNA   length = 327
FEATURE                    Location/Qualifiers
misc_feature               1..327
```

```
                        note = Synthetic
source                  1..327
                        mol_type = other DNA
                        organism = synthetic construct
SEQUENCE: 9
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccgtca   180
aggttcagtg gcagtggatc tgggacagat ttcactctca ccatcagcag tctgcaacct   240
gaagattttg caacttacta ctgtcaacag agttacagta ccccctccgat caccttcggc   300
caagggacac gactggagat taaacga                                       327

SEQ ID NO: 10           moltype = AA  length = 109
FEATURE                 Location/Qualifiers
REGION                  1..109
                        note = Synthetic
source                  1..109
                        mol_type = protein
                        organism = synthetic construct
SEQUENCE: 10
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SYSTPPITFG QGTRLEIKR               109

SEQ ID NO: 11           moltype = DNA  length = 18
FEATURE                 Location/Qualifiers
misc_feature            1..18
                        note = Synthetic
source                  1..18
                        mol_type = other DNA
                        organism = synthetic construct
SEQUENCE: 11
cagagcatta gcagctat                                                  18

SEQ ID NO: 12           moltype = AA  length = 6
FEATURE                 Location/Qualifiers
REGION                  1..6
                        note = Synthetic
source                  1..6
                        mol_type = protein
                        organism = synthetic construct
SEQUENCE: 12
QSISSY                                                                6

SEQ ID NO: 13           moltype =   length =
SEQUENCE: 13
000

SEQ ID NO: 14           moltype =   length =
SEQUENCE: 14
000

SEQ ID NO: 15           moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 15
caacagagtt acagtacccc tccgatcacc                                     30

SEQ ID NO: 16           moltype = AA  length = 10
FEATURE                 Location/Qualifiers
REGION                  1..10
                        note = Synthetic
source                  1..10
                        mol_type = protein
                        organism = synthetic construct
SEQUENCE: 16
QQSYSTPPIT                                                           10

SEQ ID NO: 17           moltype = DNA  length = 1353
FEATURE                 Location/Qualifiers
misc_feature            1..1353
                        note = Synthetic
source                  1..1353
                        mol_type = other DNA
                        organism = synthetic construct
SEQUENCE: 17
```

-continued

```
caggtgcagc tgcaggagtc gggcccagga ctggtgaagc cttcggagac cctgtccctc    60
acctgcattg tctctggtgg ctccatcagt ggttacttct ggaactggat ccggcagccc   120
ccagggaagg gacttgaatg gattggttat atctattaca gtgggaccac catctacaac   180
ccctccctca agagtcgatt caccatatca ctagacacgt ccaagaacca gttctcccta   240
aagctgacct ctgtgaccgc tgcggacacg gcctatatt actgtgcgag agagtcgtat   300
aatcccctcgc cgcgatatt tgaccactgg ggccagggaa ccctggtcac cgtctcctca   360
gcctccacca agggcccatc ggtcttcccc ctggcaccct cctccaagag cacctctggg   420
ggcacagcgg ccctgggctg cctggtcaag gactacttcc ccgaaccggt gacggtgtcg   480
tggaactcag gcgccctgac cagcggcgtg cacaccttcc cggctgtcct acagtcctca   540
ggactctact ccctcagcag cgtggtgacc gtgccctcca gcagcttggg cacccagacc   600
tacatctgca acgtgaatca caagcccagc aacaccaagg tggacaagaa agttgagccc   660
aaatcttgtg acaaaactca cacatgccca ccgtgcccag cacctgaact cctggggggga  720
ccgtcagtct tcctcttccc cccaaaaccc aaggacaccc tcatgatctc ccggacccct   780
gaggtcacat gcgtggtggt ggacgtgagc cacgaagacc ctgaggtcaa gttcaactgg   840
tacgtggacg gcgtggaggt gcataatgcc aagacaaagc cgcgggagga gcagtacaac   900
agcacgtacc gtgtggtcag cgtcctcacc gtcctgcacc aggactggct gaatggcaag   960
gagtacaagt gcaaggtctc caacaaagcc ctcccagccc ccatcgagaa aaccatctc  1020
aaagccaaag ggcagccccg agaaccacag gtgtacaccc tgcccccatc ccgggatgag  1080
ctgaccaaga accaggtcag cctgacctgc ctggtcaaag gcttctatcc cagcgacatc  1140
gccgtggagt gggagagcaa tgggcagccg gagaacaact acaagaccac gcctcccgtg  1200
ctggactccg acggctcctt cttcctctac agcaagctca ccgtggacaa gagcaggtgg  1260
cagcagggga acgtcttctc atgctccgtg atgcatgagg ctctgcacaa ccactacacg  1320
cagaagtccc tctccctgtc tccgggtaaa tga                                1353

SEQ ID NO: 18           moltype = AA  length = 450
FEATURE                 Location/Qualifiers
REGION                  1..450
                        note = Synthetic
source                  1..450
                        mol_type = protein
                        organism = synthetic construct
SEQUENCE: 18
QVQLQESGPG LVKPSETLSL TCIVSGGSIS GYFWNWIRQP PGKGLEWIGY IYYSGTTIYN    60
PSLKSRFTIS LDTSKNQFSL KLTSVTAADT AVYYCARESY NPSPRYFDHW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCDKTHTCP PCPAPELLGG   240
PSVFLFPPKP KDTLMISRTP EVTCVVVDVS HEDPEVKFNW YVDGVEVHNA KTKPREEQYN   300
STYRVVSVLT VLHQDWLNGK EYKCKVSNKA LPAPIEKTIS KAKGQPREPQ VYTLPPSRDE   360
LTKNQVSLTC LVKGFYPSDI AVEWESNGQP ENNYKTTPPV LDSDGSFFLY SKLTVDKSRW   420
QQGNVFSCSV MHEALHNHYT QKSLSLSPGK                                    450

SEQ ID NO: 19           moltype = DNA  length = 648
FEATURE                 Location/Qualifiers
misc_feature            1..648
                        note = Synthetic
source                  1..648
                        mol_type = other DNA
                        organism = synthetic construct
SEQUENCE: 19
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccgtca   180
aggttcagtg gcagtggatc tgggacagat ttcactctca ccatcagcag tctgcaacct   240
gaagattttg caacttacta ctgtcaacag agttacagta cccctccgat caccttcggc   300
caagggacac gactggagat taaacgaact gtggctgcac catctgtctt catcttcccg   360
ccatctgatg agcagttgaa atctggaact gcctctgttg tgtgcctgct gaataacttc   420
tatcccagag aggccaaagt acagtggaag gtggataacg ccctccaatc gggtaactcc   480
caggagagtg tcacagagca ggacagcaag gacagcacct acagcctcag cagcaccctg   540
acgctgagca aagcagacta cgagaaacac aaagtctacg cctgcgaagt cacccatcag   600
ggcctgagct cgcccgtcac aaagagcttc aacagggag agtgttag                 648

SEQ ID NO: 20           moltype = AA  length = 215
FEATURE                 Location/Qualifiers
REGION                  1..215
                        note = Synthetic
source                  1..215
                        mol_type = protein
                        organism = synthetic construct
SEQUENCE: 20
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SYSTPPITFG QGTRLEIKRT VAAPSVFIFP   120
PSDEQLKSGT ASVVCLLNNF YPREAKVQWK VDNALQSGNS QESVTEQDSK DSTYSLSSTL   180
TLSKADYEKH KVYACEVTHQ GLSSPVTKSF NRGEC                               215

SEQ ID NO: 21           moltype = DNA  length = 360
FEATURE                 Location/Qualifiers
misc_feature            1..360
                        note = Synthetic
source                  1..360
```

```
                        mol_type = other DNA
                        organism = synthetic construct
SEQUENCE: 21
caggtgcagc tgcaggagtc gggcccagga ctggtgaagc cttcggagac cctgtccctc    60
acctgcattg tctctggtgg ctccatcagt ggttacttct ggaactggat ccggcagccc   120
ccagggaagg gacttgaatg gattggttat atctattaca gtgggaccac catctacaac   180
ccctcsccctca agagtcgatt caccatatca ctagacacgt ccaagaacca gttctcccta   240
aagctgacct ctgtgaccgc tgcggacacg gccgtatatt actgtgcgag agagtcgtat   300
gacccctccc cgcgatattt tgaccactgg ggccagggaa ccctggtcac cgtctcctca   360

SEQ ID NO: 22           moltype = AA  length = 120
FEATURE                 Location/Qualifiers
REGION                  1..120
                        note = Synthetic
source                  1..120
                        mol_type = protein
                        organism = synthetic construct
SEQUENCE: 22
QVQLQESGPG LVKPSETLSL TCIVSGGSIS GYFWNWIRQP PGKGLEWIGY IYYSGTTIYN    60
PSLKSRFTIS LDTSKNQFSL KLTSVTAADT AVYYCARESY DPSPRYFDHW GQGTLVTVSS   120

SEQ ID NO: 23           moltype = DNA  length = 42
FEATURE                 Location/Qualifiers
misc_feature            1..42
                        note = Synthetic
source                  1..42
                        mol_type = other DNA
                        organism = synthetic construct
SEQUENCE: 23
gcgagagagt cgtatgaccc ctccccgcga tattttgacc ac                        42

SEQ ID NO: 24           moltype = AA  length = 14
FEATURE                 Location/Qualifiers
REGION                  1..14
                        note = Synthetic
source                  1..14
                        mol_type = protein
                        organism = synthetic construct
SEQUENCE: 24
ARESYDPSPR YFDH                                                       14

SEQ ID NO: 25           moltype = DNA  length = 1353
FEATURE                 Location/Qualifiers
misc_feature            1..1353
                        note = Synthetic
source                  1..1353
                        mol_type = other DNA
                        organism = synthetic construct
SEQUENCE: 25
caggtgcagc tgcaggagtc gggcccagga ctggtgaagc cttcggagac cctgtccctc    60
acctgcattg tctctggtgg ctccatcagt ggttacttct ggaactggat ccggcagccc   120
ccagggaagg gacttgaatg gattggttat atctattaca gtgggaccac catctacaac   180
ccctcsccctca agagtcgatt caccatatca ctagacacgt ccaagaacca gttctcccta   240
aagctgacct ctgtgaccgc tgcggacacg gccgtatatt actgtgcgag agagtcgtat   300
gacccctccc cgcgatattt tgaccactgg ggccagggaa ccctggtcac cgtctcctca   360
gcctccacca agggcccatc ggtcttcccc ctggcaccct cctccaagag cacctctggg   420
ggcacagcgg ccctgggctg cctggtcaag gactacttcc ccgaaccggt gacggtgtcg   480
tggaactcag gcgccctgac cagcggcgtg cacaccttcc cggctgtcct acagtcctca   540
ggactctact ccctcagcag cgtggtgacc gtgccctcca gcagcttggg cacccagacc   600
tacatctgca acgtgaatca caagcccagc aacaccaagg tggacaagaa agttgagccc   660
aaatcttgtg acaaaactca cacatgccca ccgtgcccag cacctgaact cctgggggga   720
ccgtcagtct tcctcttccc cccaaaaccc aaggacaccc tcatgatctc ccggacccct   780
gaggtcacat gcgtggtggt ggacgtgagc cacgaagacc ctgaggtcaa gttcaactgg   840
tacgtggacg gcgtggaggt gcataatgcc aagacaaagc cgcgggagga gcagtacaac   900
agcacgtacc gtgtggtcag cgtcctcacc gtcctgcacc aggactggct gaatggcaag   960
gagtacaagt gcaaggtctc caacaaagcc ctcccagccc ccatcgagaa aaccatctcc  1020
aaagccaaag gcagccccg agaaccacag gtgtacaccc tgcccccatc ccgggatgag  1080
ctgaccaaga accaggtcag cctgacctgc ctggtcaaag gcttctatcc cagcgacatc  1140
gccgtggagt gggagagcaa tgggcagccg gagaacaact acaagaccac gcctcccgtg  1200
ctggactccg acggctcctt cttcctctac agcaagctca ccgtggacaa gagcaggtgg  1260
cagcagggga acgtcttctc atgctccgtg atgcatgagg ctctgcacaa ccactacacg  1320
cagaagtccc tctccctgtc tccgggtaaa tga                                1353

SEQ ID NO: 26           moltype = AA  length = 450
FEATURE                 Location/Qualifiers
REGION                  1..450
                        note = Synthetic
source                  1..450
                        mol_type = protein
```

```
                             organism = synthetic construct
SEQUENCE: 26
QVQLQESGPG LVKPSETLSL TCIVSGGSIS GYFWNWIRQP PGKGLEWIGY IYYSGTTIYN    60
PSLKSRFTIS LDTSKNQFSL KLTSVTAADT AVYYCARESY DPSPRYFDHW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCDKTHTCP PCPAPELLGG   240
PSVFLFPPKP KDTLMISRTP EVTCVVVDVS HEDPEVKFNW YVDGVEVHNA KTKPREEQYN   300
STYRVVSVLT VLHQDWLNGK EYKCKVSNKA LPAPIEKTIS KAKGQPREPQ VYTLPPSRDE   360
LTKNQVSLTC LVKGFYPSDI AVEWESNGQP ENNYKTTPPV LDSDGSFFLY SKLTVDKSRW   420
QQGNVFSCSV MHEALHNHYT QKSLSLSPGK                                   450

SEQ ID NO: 27              moltype = DNA   length = 360
FEATURE                    Location/Qualifiers
misc_feature               1..360
                           note = Synthetic
source                     1..360
                           mol_type = other DNA
                           organism = synthetic construct
SEQUENCE: 27
caggtgcagc tgcaggagtc gggcccagga ctggtgaagc cttcggagac cctgtccctc    60
acctgcattg tctctggtgg ctccatcagt ggttacttct ggaactggat ccggcagccc   120
ccagggaagg gacttgaatg gattggttat atctattaca gtgggaccac catctacaac   180
ccctccctca agagtcgatt caccatatca ctagacacgt ccaagaacca gttctcccta   240
aagctgacct ctgtgaccgc tgcggacacg gccgtatatt actgtgcgag agagtcgtat   300
gagccctccc cgcgatattt tgaccactgg ggccagggaa ccctggtcac cgtctcctca   360

SEQ ID NO: 28              moltype = AA   length = 120
FEATURE                    Location/Qualifiers
REGION                     1..120
                           note = Synthetic
source                     1..120
                           mol_type = protein
                           organism = synthetic construct
SEQUENCE: 28
QVQLQESGPG LVKPSETLSL TCIVSGGSIS GYFWNWIRQP PGKGLEWIGY IYYSGTTIYN    60
PSLKSRFTIS LDTSKNQFSL KLTSVTAADT AVYYCARESY EPSPRYFDHW GQGTLVTVSS   120

SEQ ID NO: 29              moltype = DNA   length = 42
FEATURE                    Location/Qualifiers
misc_feature               1..42
                           note = Synthetic
source                     1..42
                           mol_type = other DNA
                           organism = synthetic construct
SEQUENCE: 29
gcgagagagt cgtatgagcc ctccccgcga tattttgacc ac                       42

SEQ ID NO: 30              moltype = AA   length = 14
FEATURE                    Location/Qualifiers
REGION                     1..14
                           note = Synthetic
source                     1..14
                           mol_type = protein
                           organism = synthetic construct
SEQUENCE: 30
ARESYEPSPR YFDH                                                      14

SEQ ID NO: 31              moltype = DNA   length = 1353
FEATURE                    Location/Qualifiers
misc_feature               1..1353
                           note = Synthetic
source                     1..1353
                           mol_type = other DNA
                           organism = synthetic construct
SEQUENCE: 31
caggtgcagc tgcaggagtc gggcccagga ctggtgaagc cttcggagac cctgtccctc    60
acctgcattg tctctggtgg ctccatcagt ggttacttct ggaactggat ccggcagccc   120
ccagggaagg gacttgaatg gattggttat atctattaca gtgggaccac catctacaac   180
ccctccctca agagtcgatt caccatatca ctagacacgt ccaagaacca gttctcccta   240
aagctgacct ctgtgaccgc tgcggacacg gccgtatatt actgtgcgag agagtcgtat   300
gagccctccc cgcgatattt tgaccactgg ggccagggaa ccctggtcac cgtctcctca   360
gcctccacca agggcccatc ggtcttcccc ctggcaccct cctccaagag cacctctggg   420
ggcacagcgg ccctgggctg cctggtcaag gactacttcc ccgaaccggt gacggtgtcg   480
tggaactcag gcgccctgac cagcggcgtg cacaccttcc cggctgtcct acagtcctca   540
ggactctact ccctcagcag cgtggtgacc gtgccctcca gcagcttggg cacccagacc   600
tacatctgca acgtgaatca caagcccagc aacaccaagg tggacaagaa agttgagccc   660
aaatcttgtg acaaaactca cacatgccca ccgtgcccag cacctgaact cctggggga   720
ccgtcagtct tcctcttccc cccaaaaccc aaggacaccc tcatgatctc ccggacccct   780
gaggtcacat gcgtggtggt ggacgtgagc cacgaagacc ctgaggtcaa gttcaactgg   840
```

```
tacgtggacg gcgtggaggt gcataatgcc aagacaaagc cgcgggagga gcagtacaac   900
agcacgtacc gtgtggtcag cgtcctcacc gtcctgcacc aggactggct gaatggcaag   960
gagtacaagt gcaaggtctc caacaaagcc ctcccagccc ccatcgagaa aaccatctcc  1020
aaagccaaag ggcagccccg agaaccacag gtgtacaccc tgcccccatc ccgggatgag  1080
ctgaccaaga accaggtcag cctgacctgc ctggtcaaag gcttctatcc cagcgacatc  1140
gccgtggagt gggagagcaa tgggcagccg gagaacaact acaagaccac gcctcccgtg  1200
ctggactccg acggctcctt cttcctctac agcaagctca ccgtggacaa gagcaggtgg  1260
cagcagggga acgtcttctc atgctccgtg atgcatgagg ctctgcacaa ccactacacg  1320
cagaagtccc tctccctgtc tccgggtaaa tga                               1353
```

```
SEQ ID NO: 32          moltype = AA  length = 450
FEATURE                Location/Qualifiers
REGION                 1..450
                       note = Synthetic
source                 1..450
                       mol_type = protein
                       organism = synthetic construct
SEQUENCE: 32
QVQLQESGPG LVKPSETLSL TCIVSGGSIS GYFWNWIRQP PGKGLEWIGY IYYSGTTIYN    60
PSLKSRFTIS LDTSKNQFSL KLTSVTAADT AVYYCARESY EPSPRYFDHW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKTHTC PPCPAPELLGG            240
PSVFLFPPKP KDTLMISRTP EVTCVVVDVS HEDPEVKFNW YVDGVEVHNA KTKPREEQYN   300
STYRVVSVLT VLHQDWLNGK EYKCKVSNKA LPAPIEKTIS KAKGQPREPQ VYTLPPSRDE   360
LTKNQVSLTC LVKGFYPSDI AVEWESNGQP ENNYKTTPPV LDSDGSFFLY SKLTVDKSRW   420
QQGNVFSCSV MHEALHNHYT QKSLSLSPGK                                    450

SEQ ID NO: 33          moltype = DNA  length = 360
FEATURE                Location/Qualifiers
misc_feature           1..360
                       note = Synthetic
source                 1..360
                       mol_type = other DNA
                       organism = synthetic construct
SEQUENCE: 33
caggtgcagc tgcaggagtc gggcccagga ctggtgaagc cttcggagac cctgtccctc    60
acctgcattg tctctggtgg ctccatcagt ggttacttct ggaactggat ccggcagccc   120
ccagggaagg gacttgaatg gattggttat atctattaca gtgggaccac catctacaac   180
ccctccctca agagtcgatt caccatatca ctagacacgt ccaagaacca gttctccctg   240
aagctgacct ctgtgaccgc tgcggacacg gccgtatatt actgtgcgag agagtcgtat   300
tcccccctcc cgcgatattt tgaccactgg ggccagggaa ccctggtcac cgtctcctca   360

SEQ ID NO: 34          moltype = AA  length = 120
FEATURE                Location/Qualifiers
REGION                 1..120
                       note = Synthetic
source                 1..120
                       mol_type = protein
                       organism = synthetic construct
SEQUENCE: 34
QVQLQESGPG LVKPSETLSL TCIVSGGSIS GYFWNWIRQP PGKGLEWIGY IYYSGTTIYN    60
PSLKSRFTIS LDTSKNQFSL KLTSVTAADT AVYYCARESY SPSPRYFDHW GQGTLVTVSS   120

SEQ ID NO: 35          moltype = DNA  length = 42
FEATURE                Location/Qualifiers
misc_feature           1..42
                       note = Synthetic
source                 1..42
                       mol_type = other DNA
                       organism = synthetic construct
SEQUENCE: 35
gcgagagagt cgtattcccc ctccccgcga tattttgacc ac                       42

SEQ ID NO: 36          moltype = AA  length = 14
FEATURE                Location/Qualifiers
REGION                 1..14
                       note = Synthetic
source                 1..14
                       mol_type = protein
                       organism = synthetic construct
SEQUENCE: 36
ARESYSPSPR YFDH                                                      14

SEQ ID NO: 37          moltype = DNA  length = 1353
FEATURE                Location/Qualifiers
misc_feature           1..1353
                       note = Synthetic
source                 1..1353
                       mol_type = other DNA
```

```
                        organism = synthetic construct
SEQUENCE: 37
caggtgcagc tgcaggagtc gggcccagga ctggtgaagc cttcggagac cctgtccctc    60
acctgcattg tctctggtgg ctccatcagt ggttacttct ggaactggat ccggcagccc   120
ccagggaagg gacttgaatg gattggttat atctattaca gtggaccac catctacaac    180
ccctccctca agagtcgatt caccatatca ctagacacgt ccaagaacca gttctcccta   240
aagctgacct ctgtgaccgc tgcggacacg gccgtatatt actgtgcgag agagtcgtat   300
tccccctccc cgcgatattt tgaccactgg ggccagggaa ccctggtcac cgtctcctca   360
gcctccacca agggcccatc ggtcttcccc ctggcaccct cctccaagag cacctctggg   420
ggcacagcgg ccctgggctg cctggtcaag gactacttcc ccgaaccggt gacggtgtcg   480
tggaactcag gcgccctgac cagcggcgtg cacaccttcc cggctgtcct acagtcctca   540
ggactctact ccctcagcag cgtggtgacc gtgccctcca gcagcttggg cacccagacc   600
tacatctgca acgtgaatca caagcccagc aacaccaagg tggacaagaa agttgagccc   660
aaatcttgtg acaaaactca cacatgccca ccgtgcccag cacctgaact cctggggggga  720
ccgtcagtct tcctcttccc cccaaaaccc aaggacaccc tcatgatctc ccggacccct   780
gaggtcacat gcgtggtggt ggacgtgagc cacgaagacc ctgaggtcaa gttcaactgg   840
tacgtggacg gcgtggaggt gcataatgcc aagacaaagc cgcggggagga gcagtacaac  900
agcacgtacc gtgtggtcag cgtcctcacc gtcctgcacc aggactggct gaatggcaag   960
gagtacaagt gcaaggtctc caacaaagcc ctcccagccc ccatcgagaa aaccatctcc  1020
aaagccaaag ggcagccccg agaaccacag gtgtacaccc tgcccccatc ccgggatgag  1080
ctgaccaaga accaggtcag cctgacctgc ctggtcaaag gcttctatcc cagcgacatc  1140
gccgtggagt gggagagcaa tgggcagccg gagaacaact acaagaccac gcctcccgtg  1200
ctggactccg acggctcctt cttcctctac agcaagctca ccgtggacaa gagcaggtgg  1260
cagcagggga acgtcttctc atgctccgtg atgcatgagg ctctgcacaa ccactacacg  1320
cagaagtccc tctccctgtc tccgggtaaa tga                               1353

SEQ ID NO: 38              moltype = AA  length = 450
FEATURE                    Location/Qualifiers
REGION                     1..450
                           note = Synthetic
source                     1..450
                           mol_type = protein
                           organism = synthetic construct
SEQUENCE: 38
QVQLQESGPG LVKPSETLSL TCIVSGGSIS GYFWNWIRQP PGKGLEWIGY IYYSGTTIYN    60
PSLKSRFTIS LDTSKNQFSL KLTSVTAADT AVYYCARESY SPSPRYFDHW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCDKTHTCP PCPAPELLGG   240
PSVFLFPPKP KDTLMISRTP EVTCVVVDVS HEDPEVKFNW YVDGVEVHNA KTKPREEQYN   300
STYRVVSVLT VLHQDWLNGK EYKCKVSNKA LPAPIEKTIS KAKGQPREPQ VYTLPPSRDE   360
LTKNQVSLTC LVKGFYPSDI AVEWESNGQP ENNYKTTPPV LDSDGSFFLY SKLTVDKSRW   420
QQGNVFSCSV MHEALHNHYT QKSLSLSPGK                                   450

SEQ ID NO: 39              moltype = DNA  length = 360
FEATURE                    Location/Qualifiers
misc_feature               1..360
                           note = Synthetic
source                     1..360
                           mol_type = other DNA
                           organism = synthetic construct
SEQUENCE: 39
caggtgcagc tgcaggagtc gggcccagga ctggtgaagc cttcggagac cctgtccctc    60
acctgcattg tctctggtgg ctccatcagt ggttacttct ggaactggat ccggcagccc   120
ccagggaagg gacttgaatg gattggttat atctattaca gtgggaccac catctacaac   180
ccctccctca agagtcgatt caccatatca ctagacacgt ccaagaacca gttctcccta   240
aagctgacct ctgtgaccgc tgcggacacg gccgtatatt actgtgcgag agagtcgtat   300
accccctccc cgcgatattt tgaccactgg ggccagggaa ccctggtcac cgtctcctca   360

SEQ ID NO: 40              moltype = AA  length = 120
FEATURE                    Location/Qualifiers
REGION                     1..120
                           note = Synthetic
source                     1..120
                           mol_type = protein
                           organism = synthetic construct
SEQUENCE: 40
QVQLQESGPG LVKPSETLSL TCIVSGGSIS GYFWNWIRQP PGKGLEWIGY IYYSGTTIYN    60
PSLKSRFTIS LDTSKNQFSL KLTSVTAADT AVYYCARESY TPSPRYFDHW GQGTLVTVSS   120

SEQ ID NO: 41              moltype = DNA  length = 42
FEATURE                    Location/Qualifiers
misc_feature               1..42
                           note = Synthetic
source                     1..42
                           mol_type = other DNA
                           organism = synthetic construct
SEQUENCE: 41
gcgagagagt cgtataccccc ctccccgcga tattttgacc ac                      42
```

```
SEQ ID NO: 42              moltype = AA  length = 14
FEATURE                    Location/Qualifiers
REGION                     1..14
                           note = Synthetic
source                     1..14
                           mol_type = protein
                           organism = synthetic construct
SEQUENCE: 42
ARESYTPSPR YFDH                                                     14

SEQ ID NO: 43              moltype = DNA  length = 1353
FEATURE                    Location/Qualifiers
misc_feature               1..1353
                           note = Synthetic
source                     1..1353
                           mol_type = other DNA
                           organism = synthetic construct
SEQUENCE: 43
caggtgcagc tgcaggagtc gggcccagga ctggtgaagc cttcggagac cctgtccctc      60
acctgcattg tctctggtgg ctccatcagt ggttacttct ggaactggat ccggcagccc     120
ccagggaagg gacttgaatg gattggttat atctattaca gtgggaccac catctacaac     180
ccctccctca gagtcgatt caccatatca ctagacacgt ccaagaacca gttctcccta     240
aagctgacct ctgtgaccgc tgcggacacg gccgtatatt actgtgcgag agagtcgtat     300
accccctccc cgcgatattt tgaccactgg ggccagggaa ccctggtcac cgtctcctca     360
gcctccacca agggcccatc ggtcttcccc ctggcaccct cctccaagag cacctctggg     420
ggcacagcgg ccctgggctg cctggtcaag gactacttcc ccgaaccggt gacggtgtcg     480
tggaactcag cgccctgac cagcggcgtg cacaccttcc cggctgtcct acagtcctca     540
ggactctact ccctcagcag cgtggtgacc gtgccctcca gcagcttggg cacccagacc     600
tacatctgca acgtgaatca caagcccagc aacaccaagg tggacaagaa agttgagccc     660
aaatcttgtg acaaaactca cacatgccca ccgtgcccag cacctgaact cctggggggga    720
ccgtcagtct tcctcttccc cccaaaaccc aaggacaccc tcatgatctc ccggacccct     780
gaggtcacat gcgtggtggt ggacgtgagc cacgaagacc ctgaggtcaa gttcaactgg     840
tacgtggacg gcgtggaggt gcataatgcc aagacaaagc cgcgggagga gcagtacaac     900
agcacgtacc gtgtggtcag cgtcctcacc gtcctgcacc aggactggct gaatggcaag     960
gagtacaagt gcaaggtctc caacaaagcc ctcccagccc ccatcgagaa aaccatctcc    1020
aaagccaaag ggcagccccg agaaccacag gtgtacaccc tgcccccatc ccgggatgag    1080
ctgaccaaga accaggtcag cctgacctgc ctggtcaaag gcttctatcc cagcgacatc    1140
gccgtggagt gggagagcaa tgggcagccg gagaacaact acaagaccac gcctcccgtg    1200
ctggactccg acggctcctt cttcctctac agcaagctca ccgtggacaa gagcaggtgg    1260
cagcagggga acgtcttctc atgctccgtg atgcatgagg ctctgcacaa ccactacacg    1320
cagaagtccc tctccctgtc tccgggtaaa tga                                 1353

SEQ ID NO: 44              moltype = AA  length = 450
FEATURE                    Location/Qualifiers
REGION                     1..450
                           note = Synthetic
source                     1..450
                           mol_type = protein
                           organism = synthetic construct
SEQUENCE: 44
QVQLQESGPG LVKPSETLSL TCIVSGGSIS GYFWNWIRQP PGKGLEWIGY IYYSGTTIYN      60
PSLKSRFTIS LDTSKNQFSL KLTSVTAADT AVYYCARESY TPSPRYFDHW GQGTLVTVSS     120
ASTKGPSVFP LAPSSKSTSG GTAALGCLVK DYFPEPVTVS WNSGALTSGV HTFPAVLQSS     180
GLYSLSSVVT VPSSSLGTQT YICNVNHKPS NTKVDKKVEP KSCDKTHTCP PCPAPELLGG     240
PSVFLFPPKP KDTLMISRTP EVTCVVVDVS HEDPEVKFNW YVDGVEVHNA KTKPREEQYN     300
STYRVVSVLT VLHQDWLNGK EYKCKVSNKA LPAPIEKTIS KAKGQPREPQ VYTLPPSRDE     360
LTKNQVSLTC LVKGFYPSDI AVEWESNGQP ENNYKTTPPV LDSDGSFFLY SKLTVDKSRW     420
QQGNVFSCSV MHEALHNHYT QKSLSLSPGK                                     450

SEQ ID NO: 45              moltype = AA  length = 194
FEATURE                    Location/Qualifiers
REGION                     1..194
                           note = Synthetic
source                     1..194
                           mol_type = protein
                           organism = synthetic construct
SEQUENCE: 45
MHRPRRRGTR PPPLALLAAL LLAARGADAQ RPTGGPGCGP GRLLLGTGTD ARCCRVHTTR      60
CCRDYPGEEC CSEWDCMCVQ PEFHCGDPCC TTCRHHPCPP GQGVQSQGKF SFGFQCIDCA     120
SGTFSGGHEG HCKPWTDCTQ FGFLTVFPGN KTHNAVCVPG SPPAEPEQKL ISEEDLGGEQ     180
KLISEEDLHH HHHH                                                      194

SEQ ID NO: 46              moltype = AA  length = 399
FEATURE                    Location/Qualifiers
REGION                     1..399
                           note = Synthetic
source                     1..399
                           mol_type = protein
                           organism = synthetic construct
```

```
SEQUENCE: 46
MHRPRRRGTR PPPLALLAAL LLAARGADAQ RPTGGPGCGP GRLLLGTGTD ARCCRVHTTR    60
CCRDYPGEEC CSEWDCMCVQ PEFHCGDPCC TTCRHHPCPP GQGVQSQGKF SFGFQCIDCA   120
SGTFSGGHEG HCKPWTDCTQ FGFLTVFPGN KTHNAVCVPG SPPAEPEPRG PTIKPCPPCK   180
CPAPNLLGGP SVFIFPPKIK DVLMISLSPI VTCVVVDVSE DDPDVQISWF VNNVEVHTAQ   240
TQTHREDYNS TLRVVSALPI QHQDWMSGKE FKCKVNNKDL PAPIERTISK PKGSVRAPQV   300
YVLPPPEEEM TKKQVTLTCM VTDFMPEDIY VEWTNNGKTE LNYKNTEPVL DSDGSYFMYS   360
KLRVEKKNWV ERNSYSCSVV HEGLHNHHTT KSFSRTPGK                         399

SEQ ID NO: 47           moltype = AA  length = 393
FEATURE                 Location/Qualifiers
REGION                  1..393
                        note = Synthetic
source                  1..393
                        mol_type = protein
                        organism = synthetic construct
SEQUENCE: 47
MHRPRRRGTR PPPLALLAAL LLAARGADAQ RPTGGPGCGP GRLLLGTGTD ARCCRVHTTR    60
CCRDYPGEEC CSEWDCMCVQ PEFHCGDPCC TTCRHHPCPP GQGVQSQGKF SFGFQCIDCA   120
SGTFSGGHEG HCKPWTDCTQ FGFLTVFPGN KTHNAVCVPG SPPAEPDKTH TCPPCPAPEL   180
LGGPSVFLFP PKPKDTLMIS RTPEVTCVVV DVSHEDPEVK FNWYVDGVEV HNAKTKPREE   240
QYNSTYRVVS VLTVLHQDWL NGKEYKCKVS NKALPAPIEK TISKAKGQPR EPQVYTLPPS   300
RDELTKNQVS LTCLVKGFYP SDIAVEWESN GQPENNYKTT PPVLDSDGSF FLYSKLTVDK   360
SRWQQGNVFS CSVMHEALHN HYTQKSLSLS PGK                               393

SEQ ID NO: 48           moltype = AA  length = 194
FEATURE                 Location/Qualifiers
REGION                  1..194
                        note = Synthetic
source                  1..194
                        mol_type = protein
                        organism = synthetic construct
SEQUENCE: 48
MHRPRRRGTR PPPLALLAAL LLAARGADAQ RPTGGPGCGP GRLLLGTGKD ARCCRVHPTR    60
CCRDYQGEEC CSEWDCVCVQ PEFHCGNPCC TTCQHHPCPS GQGVQPQGKF SFGFRCVDCA   120
LGTFSRGHDG HCKPWTDCTQ FGFLTVFPGN KTHNAVCVPG SPPAEPEQKL ISEEDLGGEQ   180
KLISEEDLHH HHHH                                                    194

SEQ ID NO: 49           moltype = AA  length = 241
FEATURE                 Location/Qualifiers
REGION                  1..241
                        note = Synthetic
source                  1..241
                        mol_type = protein
                        organism = synthetic construct
SEQUENCE: 49
MAQHGAMGAF RALCGLALLC ALSLGQRPTG GPGCGPGRLL LGTGTDARCC RVHTTRCCRD    60
YPGEECCSEW DCMCVQPEFH CGDPCCTTCR HHPCPPGQGV QSQGKFSFGF QCIDCASGTF   120
SGGHEGHCKP WTDCTQFGFL TVFPGNKTHN AVCVPGSPPA EPLGWLTVVL LAVAACVLLL   180
TSAQLGLHIW QLRSQCMWPR ETQLLLEVPP STEDARSCQF PEEERGERSA EEKGRLGDLW   240
V                                                                  241
```

What is claimed is:

1. A method for treating cancer, the method comprising administering to a subject in need thereof a therapeutically effective amount of a pharmaceutical composition comprising an isolated antibody or antigen-binding fragment thereof that binds to glucocorticoid-induced tumor necrosis factor receptor (GITR) and a pharmaceutically acceptable carrier, wherein the antibody or antigen-binding fragment thereof comprises:

(i) three heavy chain complementarity determining regions (HCDR1, HCDR2, and HCDR3), wherein the HCDR1 comprises the amino acid sequence of SEQ ID NO:4, the HCDR2 comprises the amino acid sequence of SEQ ID NO:6, and the HCDR3 comprises the amino acid sequence selected from the group consisting of SEQ ID NO:24, SEQ ID NO:30, SEQ ID NO:36, and SEQ ID NO:42; and (ii) three light chain complementarity determining regions (LCDR1, LCDR2, and LCDR3), wherein the LCDR1 comprises the amino acid sequence of SEQ ID NO:12, the LCDR2 comprises the amino acid sequence of SEQ ID NO:14, and the LCDR3 comprises the amino acid sequence of SEQ ID NO:16.

2. The method of claim 1, wherein the antibody or antigen-binding fragment thereof comprises an HCDR1 comprising the amino acid sequence of SEQ ID NO: 4, an HCDR2 comprising the amino acid sequence of SEQ ID NO: 6, an HCDR3 comprising the amino acid sequence of SEQ ID NO: 24, an LCDR1 comprising the amino acid sequence of SEQ ID NO: 12, an LCDR2 comprising the amino acid sequence of SEQ ID NO: 14, and an LCDR3 comprising the amino acid sequence of SEQ ID NO: 16.

3. The method of claim 2, wherein the antibody or antigen-binding fragment thereof comprises an HCVR having the amino acid sequence of SEQ ID NO: 22.

4. The method of claim 1, wherein the antibody or antigen-binding fragment thereof comprises an HCDR1 comprising the amino acid sequence of SEQ ID NO: 4, an HCDR2 comprising the amino acid sequence of SEQ ID NO: 6, an HCDR3 comprising the amino acid sequence of SEQ ID NO: 30, an LCDR1 comprising the amino acid sequence of SEQ ID NO: 12, an LCDR2 comprising the amino acid sequence of SEQ ID NO: 14, and an LCDR3 comprising the amino acid sequence of SEQ ID NO: 16.

5. The method of claim 4, wherein the antibody or antigen-binding fragment thereof comprises an HCVR having the amino acid sequence of SEQ ID NO: 28.

6. The method of claim 1, wherein the antibody or antigen-binding fragment thereof comprises an HCDR1 comprising the amino acid sequence of SEQ ID NO: 4, an HCDR2 comprising the amino acid sequence of SEQ ID NO: 6, an HCDR3 comprising the amino acid sequence of SEQ ID NO: 36, an LCDR1 comprising the amino acid sequence of SEQ ID NO: 12, an LCDR2 comprising the amino acid sequence of SEQ ID NO: 14, and an LCDR3 comprising the amino acid sequence of SEQ ID NO: 16.

7. The method of claim 6, wherein the antibody or antigen-binding fragment thereof comprises an HCVR having the amino acid sequence of SEQ ID NO: 34.

8. The method of claim 1, wherein the antibody or antigen-binding fragment thereof comprises an HCDR1 comprising the amino acid sequence of SEQ ID NO: 4, an HCDR2 comprising the amino acid sequence of SEQ ID NO: 6, an HCDR3 comprising the amino acid sequence of SEQ ID NO: 42, an LCDR1 comprising the amino acid sequence of SEQ ID NO: 12, an LCDR2 comprising the amino acid sequence of SEQ ID NO: 14, and an LCDR3 comprising the amino acid sequence of SEQ ID NO: 16.

9. The method of claim 8, wherein the antibody or antigen-binding fragment thereof comprises an HCVR having the amino acid sequence of SEQ ID NO: 40.

10. The method of claim 1, wherein the antibody or antigen-binding fragment thereof comprises an LCVR having the amino acid sequence of SEQ ID NO: 10.

11. The method of claim 1, wherein the antibody or antigen-binding fragment thereof comprises an HCVR comprising the amino acid sequence of SEQ ID NO: 22, and an LCVR comprising the amino acid sequence of SEQ ID NO: 10.

12. The method of claim 1, wherein the antibody or antigen-binding fragment thereof comprises an HCVR comprising the amino acid sequence of SEQ ID NO: 28, and an LCVR comprising the amino acid sequence of SEQ ID NO: 10.

13. The method of claim 1, wherein the antibody or antigen-binding fragment thereof comprises an HCVR comprising the amino acid sequence of SEQ ID NO: 34, and an LCVR comprising the amino acid sequence of SEQ ID NO: 10.

14. The method of claim 1, wherein the antibody or antigen-binding fragment thereof comprises an HCVR comprising the amino acid sequence of SEQ ID NO: 40, and an LCVR comprising the amino acid sequence of SEQ ID NO: 10.

15. The method of claim 1, wherein the antibody or antigen-binding fragment thereof is an antibody which comprises a heavy chain and a light chain, wherein the heavy chain comprises the amino acid sequence of SEQ ID NO: 26.

16. The method of claim 1, wherein the antibody or antigen-binding fragment thereof is an antibody which comprises a heavy chain and a light chain, wherein the heavy chain comprises the amino acid sequence of SEQ ID NO: 32.

17. The method of claim 1, wherein the antibody or antigen-binding fragment thereof is an antibody which comprises a heavy chain and a light chain, wherein the heavy chain comprises the amino acid sequence of SEQ ID NO: 38.

18. The method of claim 1, wherein the antibody or antigen-binding fragment thereof is an antibody which comprises a heavy chain and a light chain, wherein the heavy chain comprises the amino acid sequence of SEQ ID NO: 44.

19. The method of claim 1, wherein the antibody or antigen-binding fragment thereof is an antibody which comprises a heavy chain and a light chain, wherein the light chain comprises the amino acid sequence of SEQ ID NO: 20.

20. The method of claim 1, further comprising administering to the subject an agonistic antibody or antigen-binding fragment thereof that binds to a second T-cell activating receptor, wherein the T-cell activating receptor is CD28, OX40, CD137, CD27, or HVEM.

21. The method of claim 1, further comprising administering to the subject a PD-1 inhibitor, CTLA-4 inhibitor, a TIM-3 inhibitor, a BTLA inhibitor, a LAG-3 inhibitor, or a VISTA antagonist.

22. The method of claim 21, wherein the PD-1 inhibitor is cemiplimab.

23. The method of claim 1, further comprising administering radiation therapy to the subject.

24. The method of claim 1, further comprising administering one or more chemotherapeutic agents to the subject.

25. The method of claim 1, wherein the cancer is selected from the group consisting of squamous cell skin cancer, cutaneous squamous cell carcinoma (CSCC), myeloma, lung cancer, including small cell lung cancer and non-small cell lung cancer (NSCLC), melanoma, head and neck squamous cell carcinoma (SCCHN), cervical cancer, including cervical squamous cell carcinoma (cervical SCC), renal cell carcinoma (RCC), adenocarcinoma, colorectal cancer (CRC), pancreatic carcinoma, head and neck cancer, prostate cancer, glioblastoma multiforme, malignant gliomas, osteosarcoma, gastric cancer, malignant mesothelioma, multiple myeloma, ovarian cancer, synovial sarcoma, thyroid cancer, breast cancer, including triple negative breast cancer, testicular cancer, esophageal cancer, uterine cancer, endometrial cancer, liver cancer, immune checkpoint blockade (ICB) naive cancer, and ICB experienced cancer.

26. The method of claim 2, wherein the method further comprises administering to the subject a therapeutically effective amount of
cemiplimab.

27. A method for modulating anti-tumor immune response, the method comprising administering to a subject in need thereof a therapeutically effective amount of an antibody or antigen-binding fragment thereof that binds to glucocorticoid-induced tumor necrosis factor receptor (GITR), wherein the antibody or antigen-binding fragment thereof comprises:
  (i) three heavy chain complementarity determining regions (HCDR1, HCDR2, and HCDR3), wherein the HCDR1 comprises the amino acid sequence of SEQ ID NO:4, the HCDR2 comprises the amino acid sequence of SEQ ID NO:6, and the HCDR3 comprises the amino acid sequence selected from the group consisting of SEQ ID NO:24, SEQ ID NO:30, SEQ ID NO:36, and SEQ ID NO:42; and
  (ii) three light chain complementarity determining regions (LCDR1, LCDR2, and LCDR3), wherein the LCDR1 comprises the amino acid sequence of SEQ ID NO:12, the LCDR2 comprises the amino acid sequence of SEQ ID NO:14, and the LCDR3 comprises the amino acid sequence of SEQ ID NO:16.

28. The method of claim 27, wherein the antibody or antigen-binding fragment thereof comprises an HCDR1 comprising the amino acid sequence of SEQ ID NO: 4, an HCDR2 comprising the amino acid sequence of SEQ ID NO: 6, an HCDR3 comprising the amino acid sequence of SEQ ID NO: 24, an LCDR1 comprising the amino acid sequence of SEQ ID NO: 12, an LCDR2 comprising the amino acid sequence of SEQ ID NO: 14, and an LCDR3 comprising the amino acid sequence of SEQ ID NO: 16.

29. The method of claim 28, wherein the antibody or antigen-binding fragment thereof comprises an HCVR having the amino acid sequence of SEQ ID NO: 22.

30. The method of claim 27, wherein the antibody or antigen-binding fragment thereof comprises an HCDR1 comprising the amino acid sequence of SEQ ID NO: 4, an HCDR2 comprising the amino acid sequence of SEQ ID NO: 6, an HCDR3 comprising the amino acid sequence of SEQ ID NO: 30, an LCDR1 comprising the amino acid sequence of SEQ ID NO: 12, an LCDR2 comprising the amino acid sequence of SEQ ID NO: 14, and an LCDR3 comprising the amino acid sequence of SEQ ID NO: 16.

31. The method of claim 30, wherein the antibody or antigen-binding fragment thereof comprises an HCVR having the amino acid sequence of SEQ ID NO: 28.

32. The method of claim 27, wherein the antibody or antigen-binding fragment thereof comprises an HCDR1 comprising the amino acid sequence of SEQ ID NO: 4, an HCDR2 comprising the amino acid sequence of SEQ ID NO: 6, an HCDR3 comprising the amino acid sequence of SEQ ID NO: 36, an LCDR1 comprising the amino acid sequence of SEQ ID NO: 12, an LCDR2 comprising the amino acid sequence of SEQ ID NO: 14, and an LCDR3 comprising the amino acid sequence of SEQ ID NO: 16.

33. The method of claim 32, wherein the antibody or antigen-binding fragment thereof comprises an HCVR having the amino acid sequence of SEQ ID NO: 34.

34. The method of claim 27, wherein the antibody or antigen-binding fragment thereof comprises an HCDR1 comprising the amino acid sequence of SEQ ID NO: 4, an HCDR2 comprising the amino acid sequence of SEQ ID NO: 6, an HCDR3 comprising the amino acid sequence of SEQ ID NO: 42, an LCDR1 comprising the amino acid sequence of SEQ ID NO: 12, an LCDR2 comprising the amino acid sequence of SEQ ID NO: 14, and an LCDR3 comprising the amino acid sequence of SEQ ID NO: 16.

35. The method of claim 34, wherein the antibody or antigen-binding fragment thereof comprises an HCVR having the amino acid sequence of SEQ ID NO: 40.

36. The method of claim 27, wherein the antibody or antigen-binding fragment thereof comprises an LCVR having the amino acid sequence of SEQ ID NO: 10.

37. The method of claim 27, wherein the antibody or antigen-binding fragment thereof comprises an HCVR comprising the amino acid sequence of SEQ ID NO: 22, and an LCVR comprising the amino acid sequence of SEQ ID NO: 10.

38. The method of claim 27, wherein the antibody or antigen-binding fragment thereof comprises an HCVR comprising the amino acid sequence of SEQ ID NO: 28, and an LCVR comprising the amino acid sequence of SEQ ID NO: 10.

39. The method of claim 27, wherein the antibody or antigen-binding fragment thereof comprises an HCVR comprising the amino acid sequence of SEQ ID NO: 34, and an LCVR comprising the amino acid sequence of SEQ ID NO: 10.

40. The method of claim 27, wherein the antibody or antigen-binding fragment thereof comprises an HCVR comprising the amino acid sequence of SEQ ID NO: 40, and an LCVR comprising the amino acid sequence of SEQ ID NO: 10.

41. The method of claim 27, wherein the antibody or antigen-binding fragment thereof is an antibody which comprises a heavy chain and a light chain, wherein the heavy chain comprises the amino acid sequence of SEQ ID NO: 26.

42. The method of claim 27, wherein the antibody or antigen-binding fragment thereof is an antibody which comprises a heavy chain and a light chain, wherein the heavy chain comprises the amino acid sequence of SEQ ID NO: 32.

43. The method of claim 27, wherein the antibody or antigen-binding fragment thereof is an antibody which comprises a heavy chain and a light chain, wherein the heavy chain comprises the amino acid sequence of SEQ ID NO: 38.

44. The method of claim 27, wherein the antibody or antigen-binding fragment thereof is an antibody which comprises a heavy chain and a light chain, wherein the heavy chain comprises the amino acid sequence of SEQ ID NO: 44.

45. The method of claim 27, wherein the antibody or antigen-binding fragment thereof is an antibody which comprises a heavy chain and a light chain, wherein the light chain comprises the amino acid sequence of SEQ ID NO: 20.

46. The method of claim 27, further comprising administering to the subject an agonistic antibody or antigen-binding fragment thereof that binds to a second T-cell activating receptor, wherein the T-cell activating receptor is CD28, OX40, CD137, CD27, or HVEM.

47. The method of claim 27, further comprising administering to the subject a PD-1 inhibitor, CLTA-4 inhibitor, a TIM-3 inhibitor, a BTLA inhibitor, a LAG-3 inhibitor, or a VISTA antagonist.

48. The method of claim 47, wherein the PD-1 inhibitor is cemiplimab.

49. The method of claim 27, further comprising administering radiation therapy to the subject.

50. The method of claim 27, further comprising administering one or more chemotherapeutic agents to the subject.

51. The method of claim 27, wherein the cancer is selected from the group consisting of squamous cell skin cancer, cutaneous squamous cell carcinoma (CSCC), myeloma, lung cancer, including small cell lung cancer and non-small cell lung cancer (NSCLC), melanoma, head and neck squamous cell carcinoma (SCCHN), cervical cancer, including cervical squamous cell carcinoma (cervical SCC), renal cell carcinoma (RCC), adenocarcinoma, colorectal cancer (CRC), pancreatic carcinoma, head and neck cancer, prostate cancer, glioblastoma multiforme, malignant gliomas, osteosarcoma, gastric cancer, malignant mesothelioma, multiple myeloma, ovarian cancer, synovial sarcoma, thyroid cancer, breast cancer, including triple negative breast cancer, testicular cancer, esophageal cancer, uterine cancer, endometrial cancer, liver cancer, immune checkpoint blockade (ICB) naive cancer, and ICB experienced cancer.

52. The method of claim 28, wherein the method further comprises administering to the subject a therapeutically effective amount of cemiplimab.

53. A method for treating a cancer or modulating anti-tumor immune response in a subject in need thereof, the method comprising administering to the subject a therapeutically effective amount of each of (i) an antibody or antigen-binding fragment thereof that specifically binds to GITR, and (ii) cemiplimab;
 wherein the antibody or antigen-binding fragment thereof that specifically binds to GITR comprises an HCVR having the amino acid sequence of SEQ ID NO: 22 and an LCVR having the amino acid sequence of SEQ ID NO: 10.

54. The method of claim 53, wherein the subject has a solid tumor.

55. The method of claim 53, wherein the subject has head and neck squamous cell carcinoma.

* * * * *